(12) United States Patent
De Kock et al.

(10) Patent No.: US 11,207,537 B2
(45) Date of Patent: Dec. 28, 2021

(54) ELECTRODE DESIGNS IN IMPLANTABLE DEFIBRILLATOR SYSTEMS

(71) Applicant: CARDIAC PACEMAKERS, INC., St. Paul, MN (US)

(72) Inventors: Andrew L. De Kock, Ham Lake, MN (US); G. Shantanu Reddy, Minneapolis, MN (US); Robert D. Brock, II, St. Paul, MN (US); Stephen J. Hahn, Shoreview, MN (US); Brendan E. Koop, Ham Lake, MN (US); Moira B. Sweeney, St. Paul, MN (US); Wyatt K. Stahl, Little Canada, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 16 days.

(21) Appl. No.: 16/508,837

(22) Filed: Jul. 11, 2019

(65) Prior Publication Data
US 2019/0329060 A1    Oct. 31, 2019

Related U.S. Application Data

(63) Continuation of application No. 15/587,020, filed on May 4, 2017, now Pat. No. 10,391,325.
(Continued)

(51) Int. Cl.
*A61N 1/39* (2006.01)
*A61N 1/05* (2006.01)
*A61N 1/38* (2006.01)

(52) U.S. Cl.
CPC .............. *A61N 1/3968* (2013.01); *A61N 1/05* (2013.01); *A61N 1/0504* (2013.01);
(Continued)

(58) Field of Classification Search
CPC ...... A61N 1/3968; A61N 1/05; A61N 1/0504; A61N 1/0563; A61N 1/38; A61N 1/3925; A61N 1/3956; A61N 1/37518
See application file for complete search history.

(56) References Cited

U.S. PATENT DOCUMENTS

| 4,291,707 A | 9/1981 | Heilman et al. |
| 4,817,634 A | 4/1989 | Holleman et al. |
| (Continued) | | |

FOREIGN PATENT DOCUMENTS

| WO | 0241946 A2 | 5/2002 |
| WO | 03018122 A1 | 3/2003 |

OTHER PUBLICATIONS

A Patient's Guide—Living with your S-ICD System, 2012.
(Continued)

*Primary Examiner* — Lindsey G Wehrheim
(74) *Attorney, Agent, or Firm* — Seager, Tufte & Wickhem LLP

(57) ABSTRACT

A subcutaneous implantable cardioverter-defibrillator (S-ICD) comprising shocking electrodes configured to reduce the defibrillation threshold. The S-ICD may include a canister housing a source of electrical energy, a capacitor, and operational circuitry that senses heart rhythms and an electrode and lead assembly. The electrode and lead assembly may comprise a lead, at least one sensing electrode, and at least one shocking electrode. The at least one shocking electrode may extend over a length in the range of 50 to 110 millimeters and a width in the range of 1 to 40 millimeters.

18 Claims, 39 Drawing Sheets

Related U.S. Application Data

(60) Provisional application No. 62/344,042, filed on Jun. 1, 2016, provisional application No. 62/331,737, filed on May 4, 2016.

(52) U.S. Cl.
CPC ............. *A61N 1/0563* (2013.01); *A61N 1/38* (2013.01); *A61N 1/3925* (2013.01); *A61N 1/3956* (2013.01)

(56) References Cited

U.S. PATENT DOCUMENTS

| | | | |
|---|---|---|---|
| 5,203,348 A | 4/1993 | Dahl et al. | |
| 5,331,966 A | 7/1994 | Bennett et al. | |
| 5,336,254 A | 8/1994 | Brennan et al. | |
| 5,348,538 A | 9/1994 | Wang et al. | |
| 5,534,022 A | 7/1996 | Hoffmann et al. | |
| 5,714,110 A | 2/1998 | Wang et al. | |
| 5,865,728 A | 2/1999 | Moll et al. | |
| 6,038,483 A | 3/2000 | Kenknight et al. | |
| 6,102,890 A | 8/2000 | Stivland et al. | |
| 6,148,230 A | 11/2000 | Kenknight | |
| 6,546,292 B1 | 4/2003 | Steinhaus et al. | |
| 6,647,292 B1 | 11/2003 | Bardy et al. | |
| 6,721,597 B1 | 4/2004 | Bardy et al. | |
| 7,070,576 B2 | 7/2006 | O'Brien et al. | |
| 7,149,575 B2 | 12/2006 | Ostroff et al. | |
| 7,288,096 B2 | 10/2007 | Chin | |
| 7,299,092 B2 | 11/2007 | Bardy et al. | |
| 7,499,758 B2 | 3/2009 | Cates et al. | |
| 7,522,959 B2 | 4/2009 | Hauser et al. | |
| 7,570,997 B2 | 8/2009 | Lovett et al. | |
| 7,632,288 B2 | 12/2009 | Wu | |
| 7,657,322 B2 | 2/2010 | Bardy et al. | |
| 7,684,864 B2 | 3/2010 | Olson et al. | |
| 7,734,343 B2 | 6/2010 | Ransbury et al. | |
| 7,758,604 B2 | 7/2010 | Wu et al. | |
| 7,769,472 B2 | 8/2010 | Gerber | |
| 7,890,191 B2 | 2/2011 | Rutten et al. | |
| 7,976,557 B2 | 7/2011 | Kunis | |
| 8,050,774 B2 | 11/2011 | Kveen et al. | |
| 8,079,959 B2 | 12/2011 | Sanghera et al. | |
| 8,157,813 B2 | 4/2012 | Ko et al. | |
| 8,231,637 B2 | 7/2012 | Greenberg et al. | |
| 8,241,210 B2 | 8/2012 | Lunsford et al. | |
| 8,285,375 B2 | 10/2012 | Bardy et al. | |
| 8,364,280 B2 | 1/2013 | Marnfeldt et al. | |
| 8,483,841 B2 | 7/2013 | Sanghera et al. | |
| 8,491,615 B2 | 7/2013 | Manderfeld et al. | |
| 8,577,454 B2 | 11/2013 | Bardy et al. | |
| 8,644,926 B2 | 2/2014 | Ostroff et al. | |
| 8,660,668 B2 | 2/2014 | Bardy et al. | |
| 8,706,217 B2 | 4/2014 | Bardy et al. | |
| 8,718,760 B2 | 5/2014 | Bardy et al. | |
| 8,718,793 B2 | 5/2014 | O'Connor | |
| 8,801,729 B2 | 8/2014 | Ko et al. | |
| 8,986,335 B2 | 3/2015 | Chin | |
| 9,079,035 B2 | 7/2015 | Sanghera et al. | |
| 9,216,284 B2 | 12/2015 | O'Connor | |
| 2004/0215308 A1 | 10/2004 | Bardy et al. | |
| 2008/0183225 A1 | 7/2008 | Adamski et al. | |
| 2010/0152798 A1 | 6/2010 | Sanghera et al. | |
| 2012/0029335 A1 | 2/2012 | Sudam et al. | |
| 2014/0172034 A1* | 6/2014 | Bornzin | A61N 1/37512 607/17 |
| 2014/0330208 A1 | 11/2014 | Christie et al. | |
| 2014/0330326 A1 | 11/2014 | Thompson-Nauman et al. | |
| 2016/0213270 A1 | 7/2016 | Cao et al. | |
| 2016/0310746 A1 | 10/2016 | Greenhut et al. | |
| 2017/0020551 A1 | 1/2017 | Reddy et al. | |
| 2017/0021159 A1 | 1/2017 | Reddy et al. | |

OTHER PUBLICATIONS

Ferrari et al., Journal of Arrhythmia, 1-3, 2015.
Lieberman et al., MDT Anterior Posterior SubQ Testing Article, Heart Rhythm, vol. 5, No. 1, 28-34, 2008.
Jolley et al., Finite element modeling of subcutaneous implantable defibrillator electrodes in an adult torso, Heart Rhythm (2009).
Weiss et al., Arrhythmia/Electrophysiology, Circulation, 128, 944-954, 2013.
Darrat, Y. (May 11, 2018). B-PO05-034 / B-P005-034—Single Incision Technique For Placement Of Subcutaneous Implantable Cardioverter Defibrillators. Retrieved from http://abstractsonline.com/pp8/#!/4554/presentation/7501.
International Search Report and Written Opinion dated Jul. 25, 2017 for International Application No. PCT/US2017/031092.

* cited by examiner

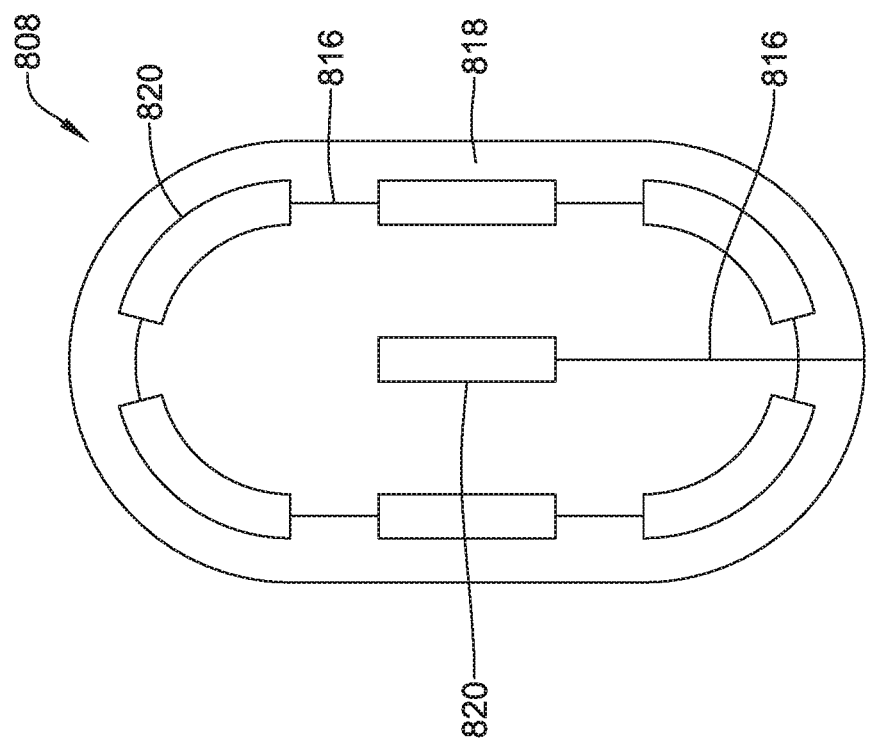

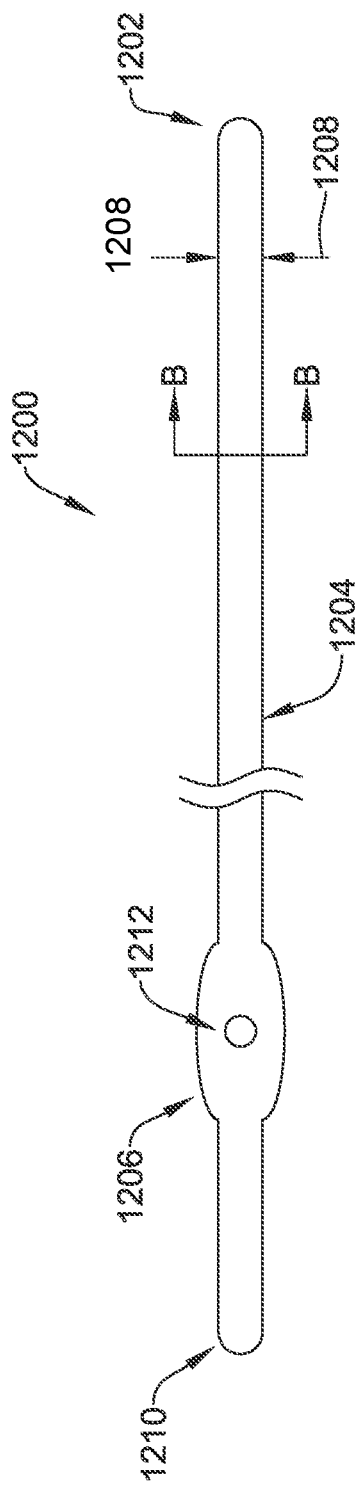
FIG. 12A
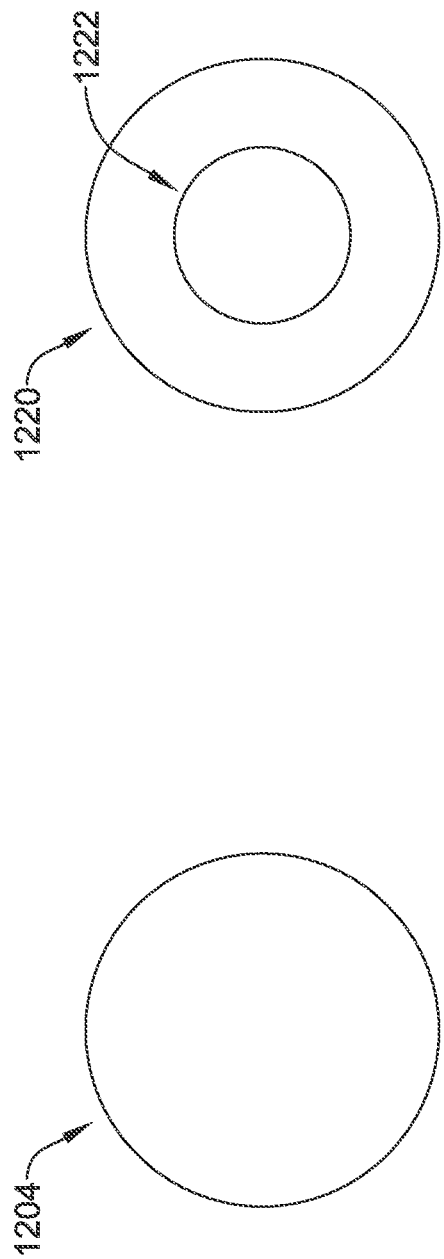
FIG. 12B
FIG. 12C

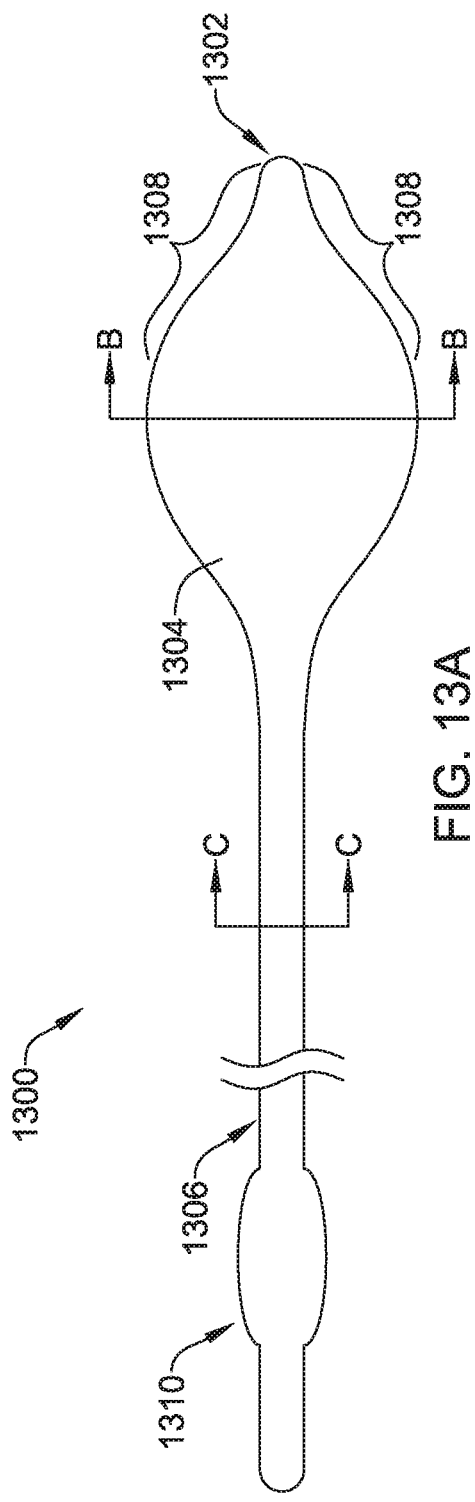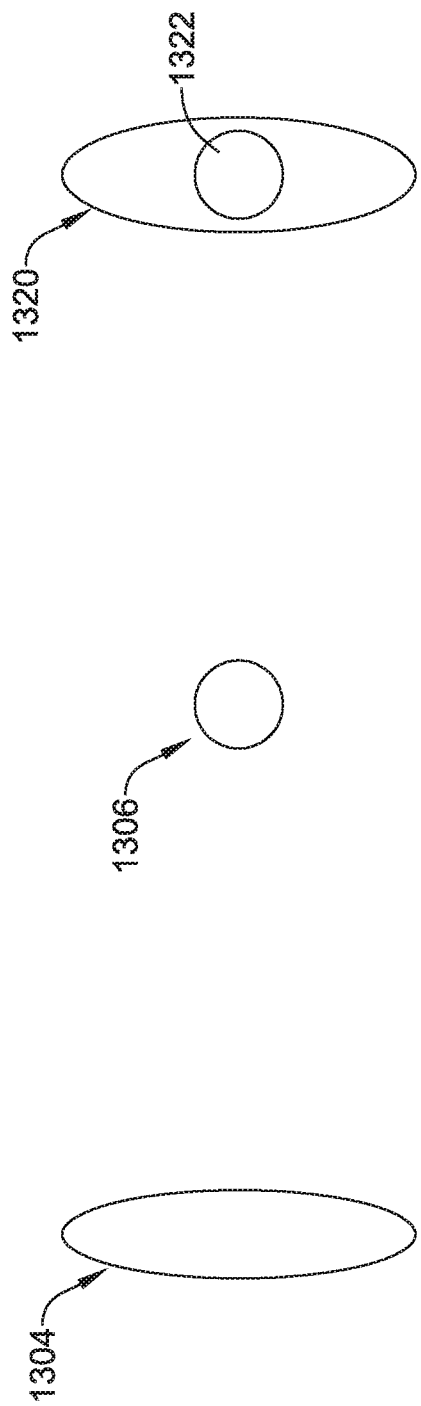
FIG. 13A
FIG. 13B
FIG. 13C
FIG. 13D

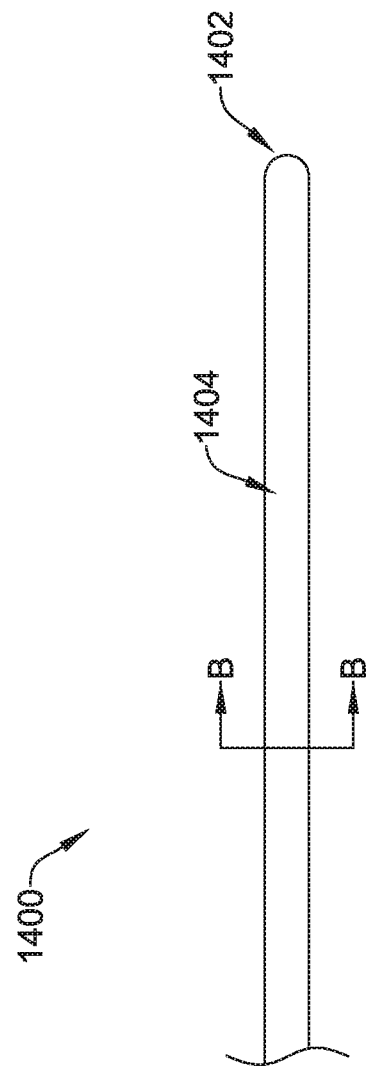

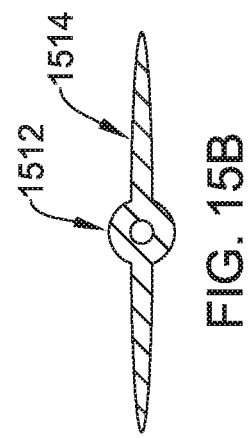
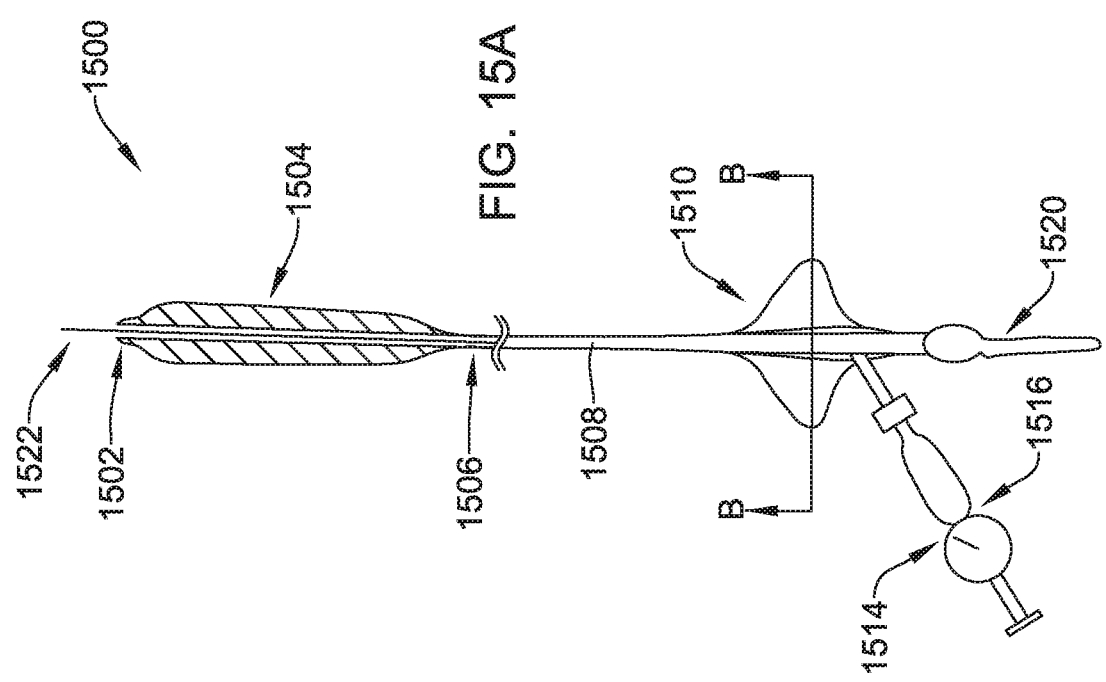

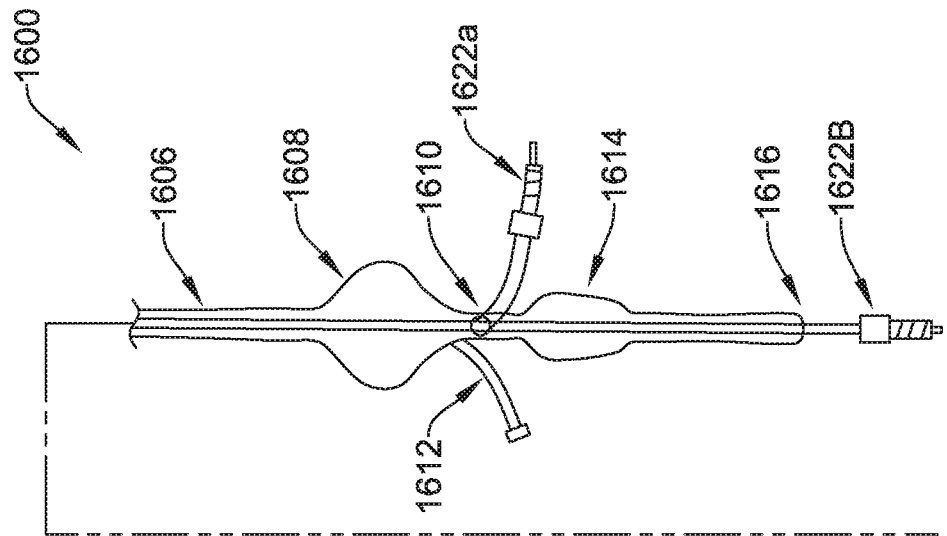
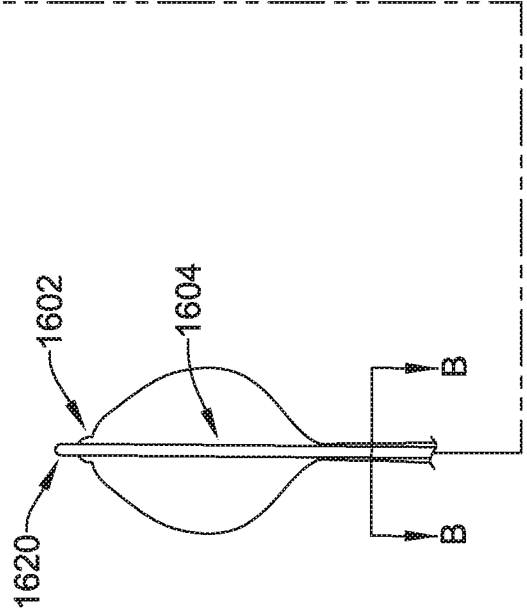
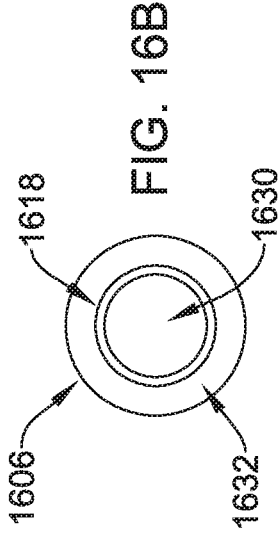
FIG. 16A
FIG. 16B

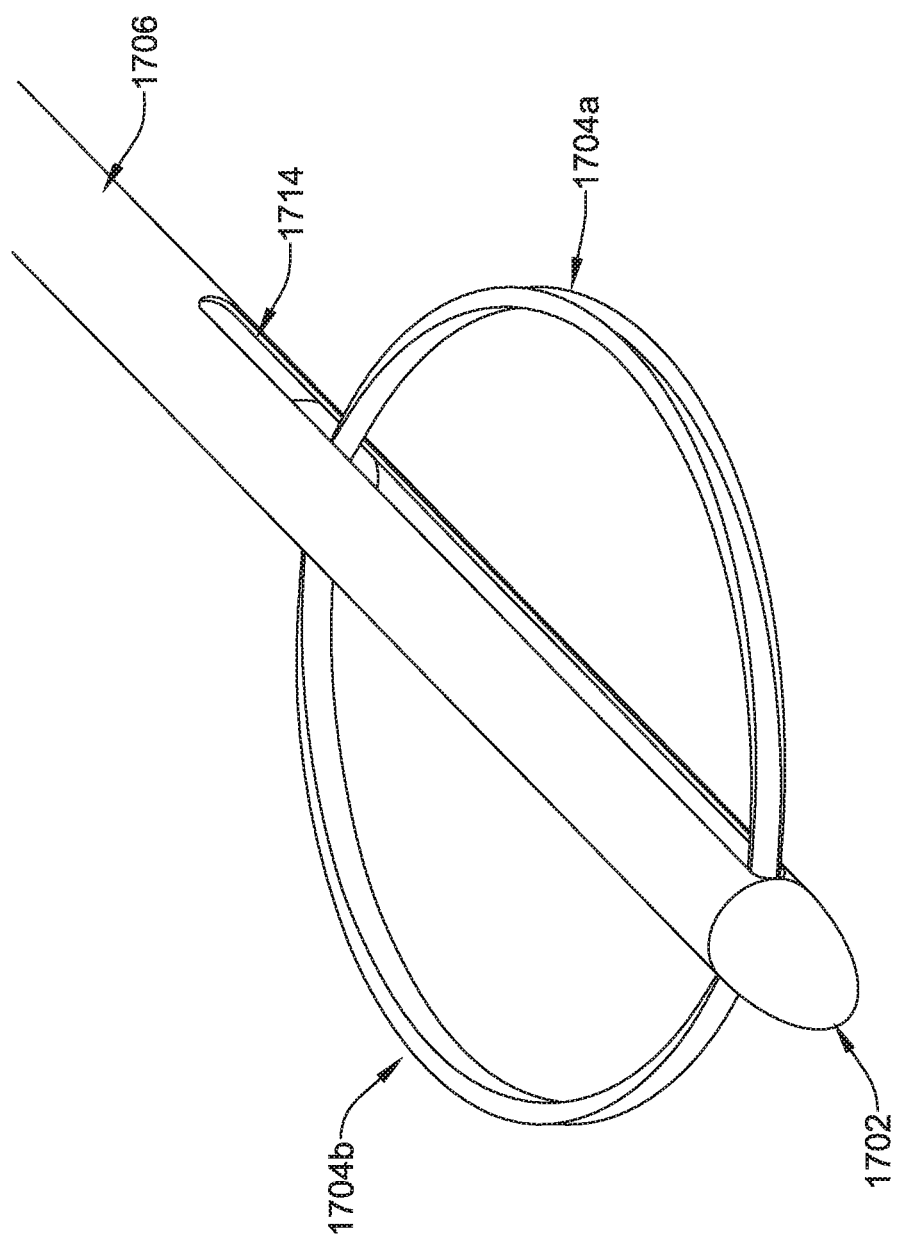

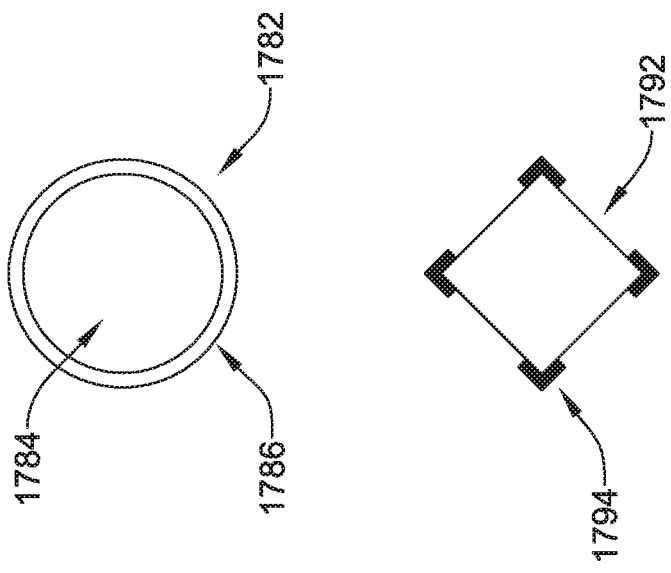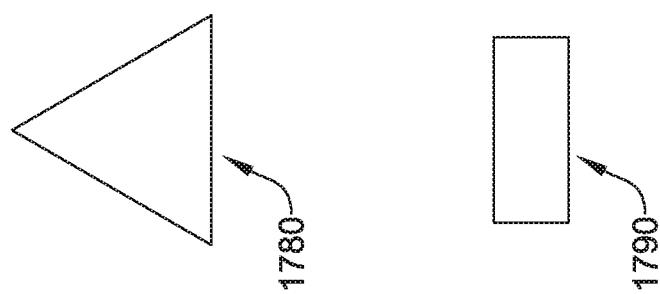
FIG. 17G

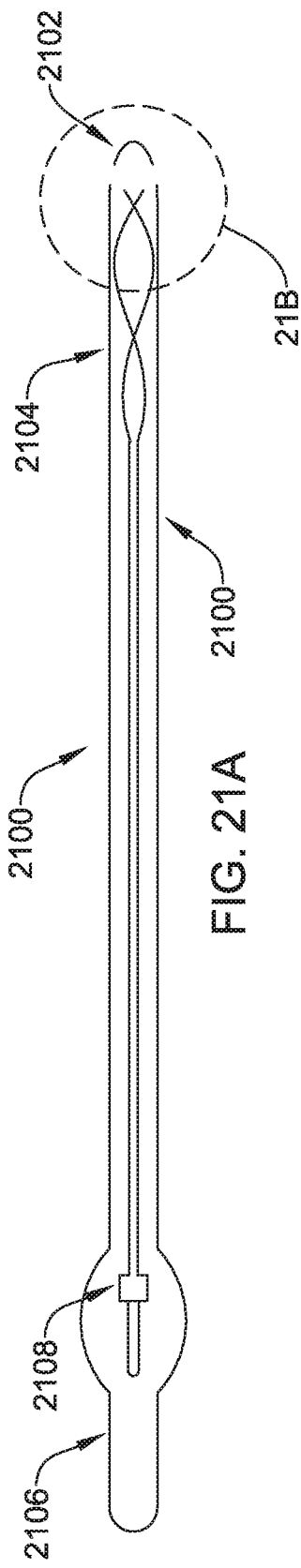
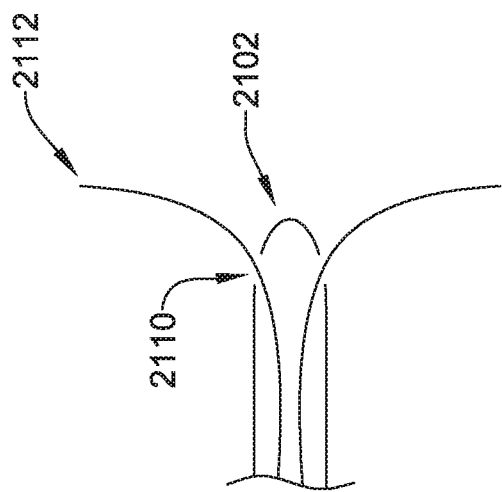
FIG. 21A
FIG. 21B

ELECTRODE DESIGNS IN IMPLANTABLE DEFIBRILLATOR SYSTEMS

CROSS-REFERENCE TO RELATED PATENT DOCUMENTS

The present application is a continuation of U.S. patent application Ser. No. 15/587,020, filed May 4, 2017 and titled ELECTRODE DESIGNS IN IMPLANTABLE DEFIBRILLATOR SYSTEMS, which claims the benefit of and priority to U.S. Provisional Patent Application Ser. No. 62/331,737, filed on May 4, 2016, and titled ELECTRODE DESIGNS IN IMPLANTABLE DEFIBRILLATOR SYSTEMS and to U.S. Provisional Patent Application Ser. No. 62/344,042, filed on Jun. 1, 2016, and titled ELECTRODE DESIGNS IN IMPLANTABLE DEFIBRILLATOR SYSTEMS the disclosures of which are incorporated herein by reference. The present application is related to U.S. Provisional Application Ser. No. 62/331,721 filed on May 4, 2016 and titled DELIVERY TOOLS IN IMPLANTABLE DEFIBRILLATOR SYSTEMS, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

The first approved commercial version of the S-ICD System™ delivered approximately 80 Joules of energy for defibrillation therapy. To supply this amount of energy in a timely fashion over the life of the device, three high power capacitors and three batteries were used in the first approved S-ICD System™ devices. Enhancements to reduce the total energy required may allow for reduction in size by facilitating the use of smaller or fewer batteries and/or capacitors. In addition, it is desired to increase the already high likelihood of successful implantation as measured by the ability to convert induced ventricular fibrillation at implant using 65 Joule therapy (an imputed success rate of 96.5% was calculated in PMA P11042: FDA Summary of Safety and Effectiveness Data, available online at http://www.accessdata.fda.gov/cdrh_docs/pdf11/P110042b.pdf). New and alternative defibrillation lead and electrode designs, as well as alternative implant tools and methods, may be useful to achieve these goals.

OVERVIEW

The present inventors have recognized, among other things, that a problem to be solved is the provision of new and different lead designs and delivery tools for use therewith for implantable defibrillators. Various electrode designs are shown below, as are new tools for implanting such devices. Some electrodes have a width or surface area that is larger than typical shocking electrodes. The increased surface area or shadow may reduce the defibrillation threshold. Some electrodes may move between a low profile delivery configuration and an expanded implanted configuration. Embedded electrodes and/or printed circuit electrodes may also be used to reduce the defibrillation threshold.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 8A-8E show another illustrative electrode for use with an implantable cardiac rhythm management system;

FIGS. 12A-12C show an illustrative tunneling tool;

FIGS. 13A-13D show another illustrative tunneling tool;

FIGS. 14A-14C show another illustrative tunneling tool;

FIGS. 15A-15E show an illustrative tunneling tool having an inflatable element;

FIGS. 16A-16B show another illustrative tunneling tool having an inflatable element;

FIGS. 17A-17G show several details and variants for another illustrative tunneling tool;

FIGS. 21A-21B show another illustrative tunneling tool.

DETAILED DESCRIPTION

Figure 1:
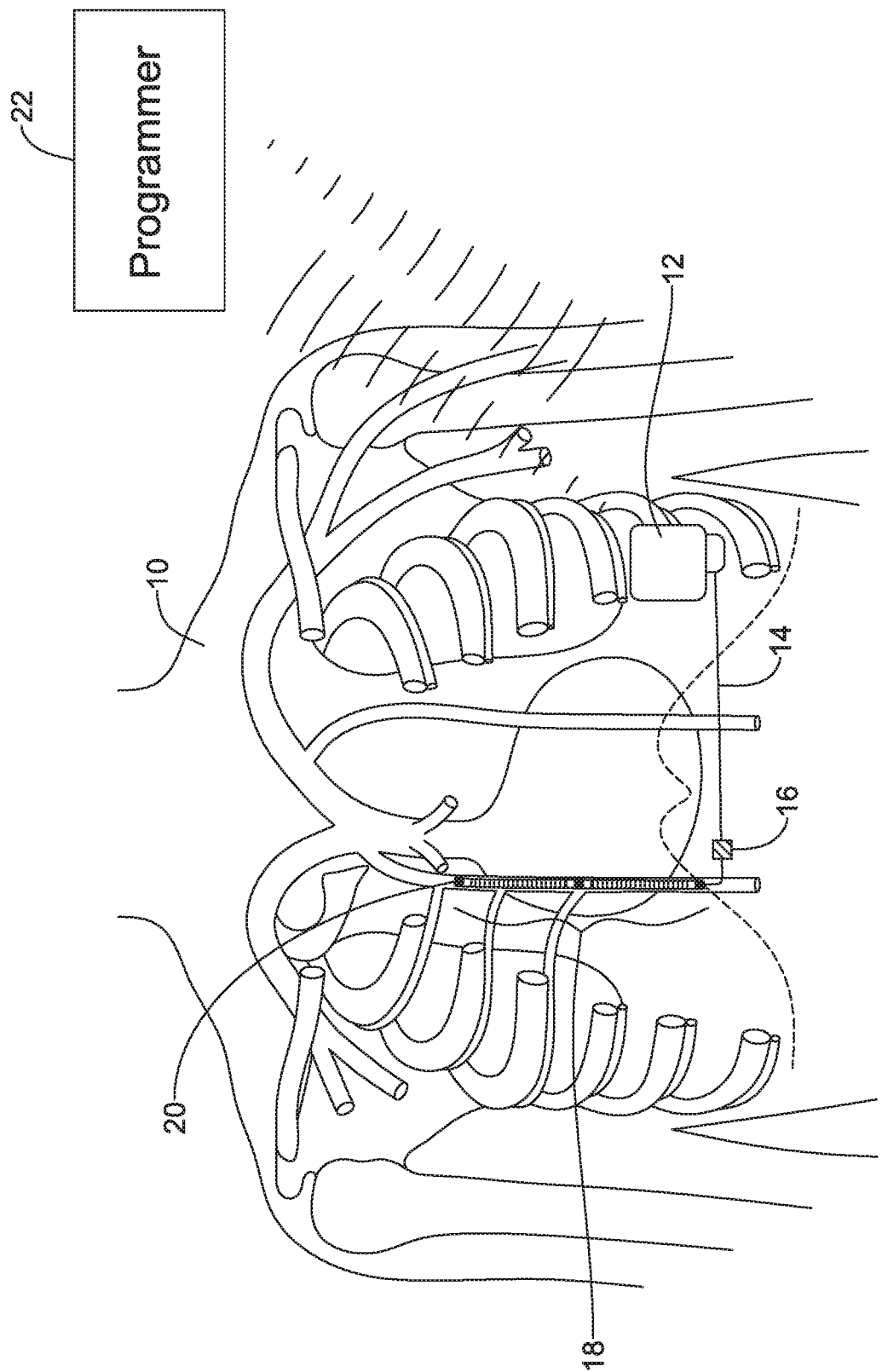
FIG. 1 shows an illustrative implantable cardiac rhythm management system.

FIG. 1 shows the subcutaneous implantable cardioverter-defibrillator (S-ICD) System™ from Cameron Health, Inc., and Boston Scientific Corporation, as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may include componentry appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12. Though not shown, the system may also be used with a remote monitor, as such systems are known in the art.

The placement of a defibrillator system entirely subcutaneously can be associated with a need for higher voltage, power and/or current when delivering therapy defibrillation and/or pacing therapy. One effect of higher power and/or voltage requirements is that the size of the implantable canister 12 may be limited by a need, for example, to include two or even three batteries and/or high power capacitors. For example, the S-ICD System® as approved by the United States Food and Drug Administration in 2012 had three batteries and three high power capacitors, which consumed the vast majority of the implantable device volume.

One proposed solution for reduction of power is placement of the lead 14 beneath the sternum, such as discussed in Guenther et al., Substernal Lead Implantation: A Novel Option to Manage DFT Failure in S-ICD Patients, Clin. Res. Cardiol (2015) 104:189-191. Some tools and methods to perform substernal implantation are discussed in U.S. Provisional Patent Application 62/195,695, titled SUBSTERNAL PLACEMENT OF A PACING AND/OR DEFIBRILLATING ELECTRODE, the disclosure of which is incorporated herein by reference. The enhancements suggested in the present patent application may be implemented in subcutaneous-only and/or substernal lead systems. It should be noted that while the example of FIG. 1 shows a device implanted without any leads and/or electrodes in or on the heart, the enhancements herein may also be used in systems that include one or more such leads or electrodes. Additionally, while FIG. 1 shows a left lateral or axillary canister 12 with a parasternal lead 14, other positions may be used instead such as those shown in U.S. Pat. Nos. 6,721,597 and 7,149,575, the disclosure of which are incorporated herein by reference. For example, and without limitation, the canister 12 may be placed anterior, right-sided, posterior, abdominal, pectoral/infraclavicular, or placed in any other desired position, with the lead 14 extending vertically or horizontally on the anterior, side, or posterior of the patient's torso, for example. Additional enhancements are desired, both in terms of the electrode and lead to be implanted as well as methods and tools for such implantation.

Figure 2:
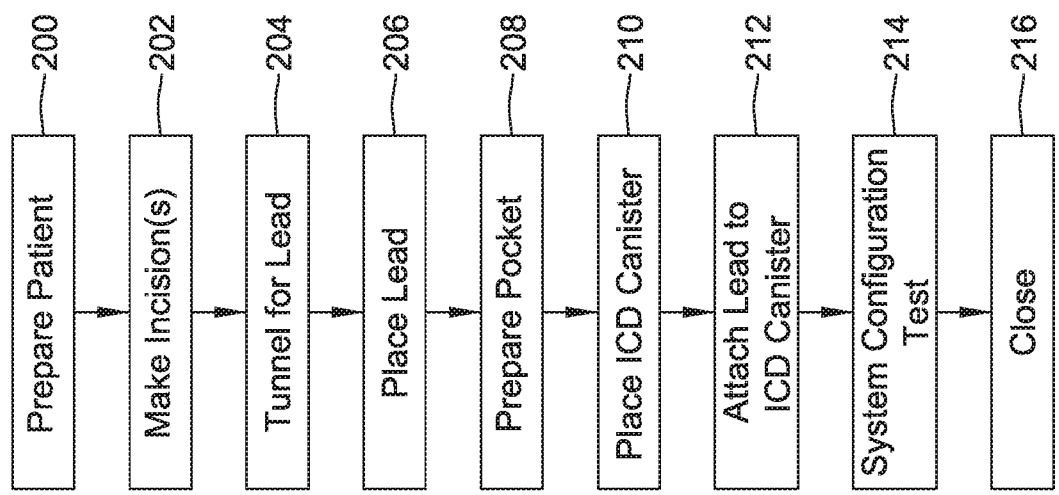
FIG. 2 shows an illustrative method in block flow form.

FIG. 2 shows an illustrative method of implantation in block flow form. In this example, the patient is prepared at 200 for implantation of the device. The patient may undergo screening and testing to ensure appropriate patient selection using device indications and the like. Optionally, in some examples a pre-screen check may be performed as disclosed in U.S. Pat. No. 8,079,959, titled PATIENT SCREENING TOOLS FOR IMPLANTABLE CARDIAC STIMULUS SYSTEMS, the disclosure of which is incorporated herein by reference. The patient may also be prepared by delivery of anesthetics and or other medications and sterile field, etc. will be prepared, as is known in the art.

One or more incisions are then made as indicated at 202. The incisions may include, for example, those suggested by FIG. 1 including an incision in the left axilla and another at or near the xiphoid process. Some procedures may further include a superior incision at or inferior to the manubrium for a subcutaneous implant procedure. Methods and devices for subcutaneous implantation of a lateral/axillary canister with parasternal lead are discussed further in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference.

Alternatively, a substernal implant procedure may include a xiphoid or sub-xiphoid incision allowing tunneling along the back side of the sternum, such as in U.S. Provisional Patent Application No. 62/195,695, titled SUBSTERNAL PLACEMENT OF A PACING OR DEFIBRILLATING ELECTRODE, the disclosure of which is incorporated herein by reference. It has also been proposed to use a single-incision implant procedure with a steerable insertion tool, for example in U.S. Provisional Patent Application No. 62/195,700, titled MINIMALLY INVASIVE METHOD TO IMPLANT A SUBCUTANEOUS ELECTRODE, or U.S. Pat. No. 6,647,292, titled UNITARY SUBCUTANEOUS ONLY IMPLANTABLE CARDIOVERTER-DEFIBRILLATOR AND OPTIONAL PACER the disclosures of which are incorporated herein by reference. If a subcutaneous implant position other than that shown in FIG. 1 is desired, the incisions may be placed elsewhere as desired, including for example, for use with right sided, anterior-posterior, or other implant positions such as shown in U.S. Pat. No. 6,721,597, titled SUBCUTANEOUS ONLY IMPLANTABLE CARDIOVERTER DEFIBRILLATOR AND OPTIONAL PACER, and U.S. Pat. No. 7,149,575, titled SUBCUTANEOUS CARDIAC STIMULATOR DEVICE HAVING AN ANTERIORLY POSITIONED ELECTRODE, the disclosures of which are incorporated herein by reference.

A subcutaneous or substernal tunnel for emplacement of a lead is then made, as indicated at 204. The tunnel, for the most part, is formed by separating tissue layers, as opposed to tearing through tissue layers themselves, and is desirably made as close to the fascia as it can in order to avoid capturing subcutaneous fat or other tissue in the electrical therapy field. Tunneling may be performed using a blunt-ended (for example, bullet-shaped) and stiff electrode insertion tool specially made for the purpose of tunneling to implant a subcutaneous electrode.

With the tunnel formed, a lead is emplaced as shown at 206. Various methods for emplacing the lead can be used. In some examples, a suture may be attached to an end of a lead after being passed through the subcutaneous tunnel and the suture is then used to pull the end of the lead from one incision to another (see, for example, US PG Publication No. 20120029335 and or the labeling of the S-ICD System as originally approved by the FDA in PMA P11042). In other examples, tunneling may be performed with a splittable sheath placed over a tunneling tool, and the tunneling tool is removed while keeping the sheath in place, such that the lead can be inserted into the splittable sheath to the desired position. In other examples a lead and an insertion tool may include attachment features, such as tines, eyelets or other features, allowing attachment therebetween, as shown for example in U.S. Pat. No. 7,657,322, titled SUBCUTANEOUS ELECTRODE WITH IMPROVED CONTACT SHAPE FOR TRANSTHORACIC CONDUCTION, and U.S. Pat. No. 8,718,793, titled ELECTRODE INSERTION TOOLS, LEAD ASSEMBLIES, KITS AND METHODS FOR PLACEMENT OF CARDIAC DEVICE ELECTRODES, the disclosures of which are incorporated herein by reference. Lead placement may also include securing the lead in a desired position by the use of sutures, clips, suture sleeves, or other devices and steps. For example, a suture sleeve integrated into or on the lead, or a suture hole, may be secured at a desired location such as (assuming implant as in FIG. 1) at the end of the lead along the sternum or near the xiphoid, with the suture being secured desirable to the fascia for secure anchoring. U.S. Provisional Patent Application No. 62/195,695 also includes some discussion of anchoring for a substernal location.

A pocket for receiving the canister of the device is also prepared, as shown at 208. Pocket preparation 208 may be done manually or using a blunt tool, for example. The ICD canister is then placed in the prepared pocket as shown at 210, and the lead is attached to the ICD canister, as shown at 212. The exact order of steps may vary; in some examples, step 212 may precede step 210 such that the lead is attached to the canister prior to placement of the canister. Step 212 may include, for example, the use of a setscrew to secure the lead and canister together. Step 210 may also include, again, suturing the ICD canister down to the fascia, if desired.

The system then may undergo configuration and testing as indicated at 214. Configuration may include setting various parameters, such as parameters for determining whether a treatable arrhythmia is occurring (for example, setting rate boundaries to define ventricular fibrillation and ventricular tachyarrhythmia for the patient), setting sensing parameters such as sensing vector selection, gain setting or other parameters, setting therapy parameters including pacing and defibrillation therapy parameters, or any other suitable parameters. System test may include the performance of induction testing, in which the patient's heart is placed in an arrhythmic state (such by inducing ventricular fibrillation by application of a stimulus on the T-wave, a long DC signal, or the use of a relatively fast 40 to 80 Hz signal), and the device is allowed detect the arrhythmia and deliver therapy to ensure both that the device can sense appropriately and that the delivered therapy will work for its intended purposes.

If system configuration and testing is completed appropriately in block 214, the procedure can end by closing all incisions as shown at 216 and/or other appropriate post-surgery steps. As noted above, the steps in FIG. 2 may be performed in an order other than that shown. Following the close of surgery 216, other testing and configuration steps may be performed as well prior to release of the patient, such as further setting of the sensing configuration, if desired.

Figure 3A:
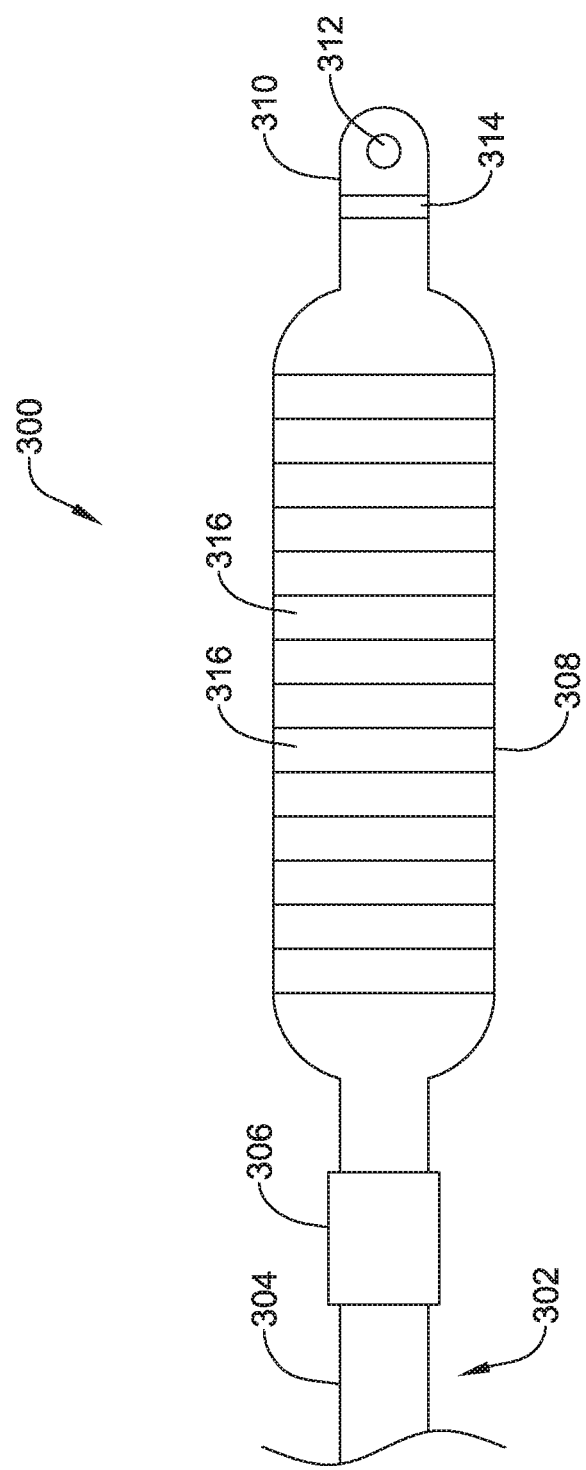
FIGS. 3A-3C show an illustrative electrode for use with an implantable cardiac rhythm management system.

FIG. 3A shows a top view of an illustrative lead and electrode assembly 300 for use with an implantable cardiac rhythm management system, such as, but not limited to the S-ICD System™ from Cameron Health, Inc., and Boston Scientific Corporation described above with respect to FIG. 1. While not explicitly shown, the lead 302 may include a proximal end with a proximal pin which along with additional contacts serves in this example as an electrical contact, which may be separated by insulating material. The proximal end may further include seal plugs. A proximal plug sheath may be provided for a region near the proximal end of the lead 302. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 302 extends from this proximal configuration through an intermediate region 304 to a distal end having a proximal electrode 306, a coil electrode 308, and a distal tip electrode 310. The positioning and/or spacing of the electrodes 306, 308, 310 may be adjusted and/or reconfigured to optimize sensing and/or therapy delivery. For example, both sensing electrodes 306, 310 may be placed proximal to or distal to the coil electrode 308. This is just an example. It is contemplated that the electrodes 306, 308, 310 may be placed beneath the skin and over the ribcage of the patient. In other embodiments, the electrodes 306, 308, 310 may be placed in a substernal location using an implant procedure that may include a xiphoid or sub-xiphoid incision that allows for tunneling along the back side of the sternum. The electrodes 306, 308, 310 may also be placed elsewhere as desired including for example, for use with right sided, anterior-posterior, or other implant positions. Some illustrative discussion of a lead as used in the S-ICD™ System is provided in U.S. Pat. No. 8,483,841.

Lead 302 is shown for illustrative purposes, however, other designs and configurations including fewer, more or different electrodes 306, 308, 310, or contacts, may be used. Additional design elements such as bifurcation or other splitting, paddles or other designs may be used instead with an anchoring device attached at the time of implant. The lead 302 is not shown as including a passageway for a stylet to use during introduction, however, a lumen for that purpose may be provided if desired. In the illustrative example, the lead 302 has a body that contains passageways having connectors therein for coupling the proximal contacts to the coil 308, proximal electrode 306, and/or distal electrode 310.

The distal tip electrode 310 is shown with a suture hole 312. The suture hole 312 may be coupled to a base portion 314. Other designs may be used. In some embodiments, a suture hole 312, or other fixation means, may not be required and/or may not be provided.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

Figure 3C:
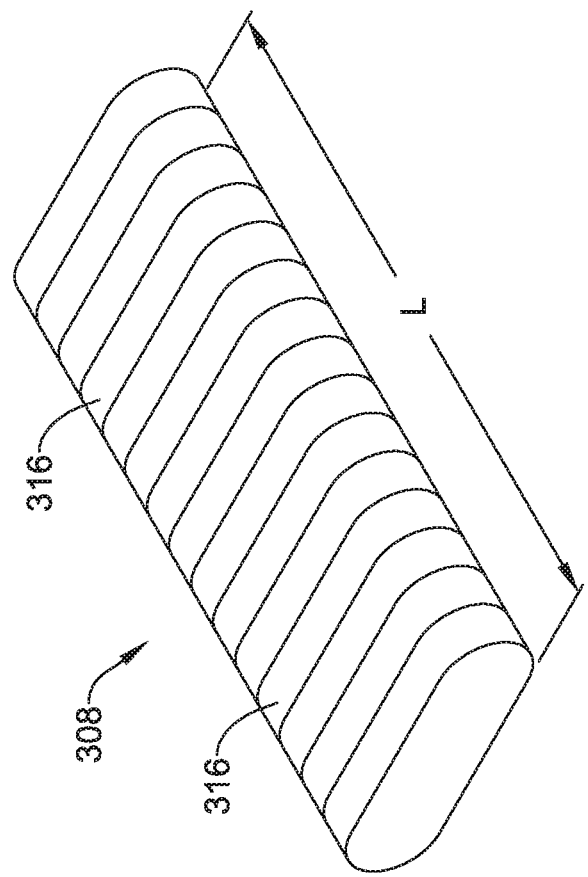
Figure 3B:
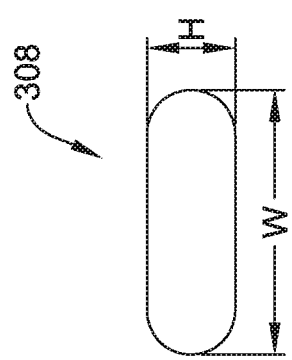

The shocking coil electrode 308 may have a generally flattened cross-sectional configuration, although this is not required. For example, referring to FIGS. 3B and 3C which illustrate an end view and a perspective view, respectively, of the illustrative coil electrode 308, the coil electrode 308 may have a cross-sectional shape that generally takes the form of an oval. The cross-sectional shape may have two curved ends and two parallel sides connecting the curved ends. Other cross-sectional shapes may also be used, including, but not limited to, rectangular, polygonal, circular, square, etc. The coil electrode 308 may have a length L that is generally larger than a width W. The width W may be generally larger than a height H of the electrode 308. The length L of the electrode 308 may be in the range of 50 to 110 millimeters (mm), 60 to 100 mm, 70 to 90 mm or about 80 mm. The width W of the electrode 308 may be in the range of 1 to 40 mm, 5 to 35 mm, 10 to 30 mm, 15 to 25 mm, or about 20 mm. The height H of the electrode 308 may be in the range of 0.5 mm to 6 mm, 1 mm to 5 mm, 2 mm to 4 mm, or about 3 mm. The coil electrode 308 may have a larger surface area and/or shadow than a typical shocking coil electrode. It is contemplated that increasing the surface area and/or shadow of the shocking electrode 308 may allow the defibrillation threshold to be lowered which may allow the canister, such as canister 12, to have a smaller profile.

The coil electrode 308 may be formed from a round or flat (ribbon) wire, as desired. In some embodiments, the coil electrode 308 may be formed as a subassembly and placed over the lead body 302. Alternatively, the coil electrode 308 may be formed as a unitary structure with or otherwise formed over the lead body 302. While not explicitly shown, the coil electrode 308 may include a lumen or passageway for receiving a stylet or other delivery aid. In some instances, adjacent windings 316 of the coil electrode 308 may be in contact with one another while in other instances adjacent windings 316 may be spread out or spaced a distance from one another, as desired.

A thin permeable membrane may be positioned over the coil 308 and/or other portions of the lead and electrode assembly 300 to inhibit tissue ingrowth. Coatings, such as, but not limited to expanded polytetrafluoroethylene (ePTFE) may also be applied to the lead and electrode assembly 300, or portions thereof, to facilitate extraction and/or to reduce tissue ingrowth. In some embodiments, one or more of the electrodes 306, 308, 310 may be include a high capacitive coating such as, but not limited to iridium oxide (IrOx), titanium nitride (TiN), or other "fractal" coatings which may be used, for example, to improve electrical performance. The lead and electrode assembly 300, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

Figure 3D:
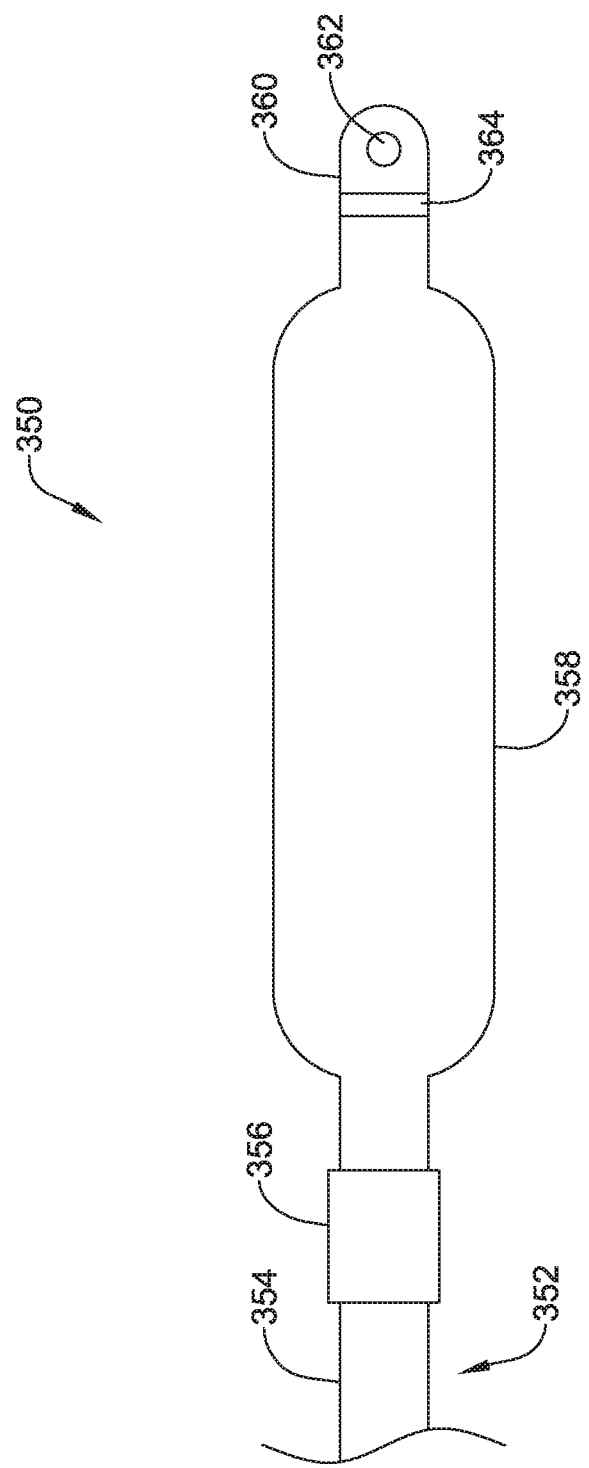
FIGS. 3D-3E show another illustrative electrode for use with an implantable cardiac rhythm management system.

FIG. 3D shows a top view of an illustrative lead and electrode assembly 350 for use with an implantable cardiac rhythm management system, such as, but not limited to the S-ICD System™ from Cameron Health, Inc., and Boston Scientific Corporation described above with respect to FIG. 1. While not explicitly shown, the lead 352 may include a proximal end with a proximal pin which along with additional contacts serves in this example as an electrical contact, which may be separated by insulating material. The proximal end may further include seal plugs. A proximal plug sheath may be provided for a region near the proximal end of the lead 352. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 352 extends from this proximal configuration through an intermediate region 354 to a distal end having a proximal electrode 356, a solid surface electrode 358, and a distal tip electrode 360. The positioning and/or spacing of the electrodes 356, 358, 360 may be adjusted and/or reconfigured to optimize sensing and/or therapy delivery. For example, both sensing electrodes 356, 360 may be placed proximal to or distal to the solid surface electrode 358. This is just an example. It is contemplated that the electrodes 356, 358, 360 may be placed beneath the skin and over the ribcage of the patient. In other embodiments, the electrodes 356, 358, 360 may be placed in a substernal location using an implant procedure that may include a xiphoid or sub-xiphoid incision that allows for tunneling along the back side of the sternum. The electrodes 356, 358, 360 may also be placed elsewhere as desired including for example, for use with right sided, anterior-posterior, or other implant positions. Some illustrative discussion of a lead as used in the S-ICD™ System is provided in U.S. Pat. No. 8,483,841.

Lead 352 is shown for illustrative purposes, however, other designs and configurations including fewer, more or different electrodes 356, 358, 360, or contacts, may be used. Additional design elements such as bifurcation or other splitting, paddles or other designs may be used instead with an anchoring device attached at the time of implant. The lead 352 is not shown as including a passageway for a stylet to use during introduction, however, a lumen for that purpose may be provided if desired. In the illustrative example, the lead 352 has a body that contains passageways having connectors therein for coupling the proximal contacts to the solid surface electrode 358, proximal electrode 356, and/or distal electrode 360.

The distal tip electrode 360 is shown with a suture hole 362. The suture hole 362 may be coupled to a base portion 364. Other designs may be used. In some embodiments, a suture hole 362, or other fixation means, may not be required and/or may not be provided.

As used herein, a solid surface electrode may have a generally, substantially, or entirely solid outer surface. In some cases, the solid surface electrode may be a solid unitary metallic structure. In other embodiments, the solid surface electrode may be a rigid polymer structure with a metallic shell disposed over the polymeric structure. It is contemplate that the metallic shell may be placed over the polymeric structure in such a way to minimize gaps or openings in the conductive portion.

Figure 3E:
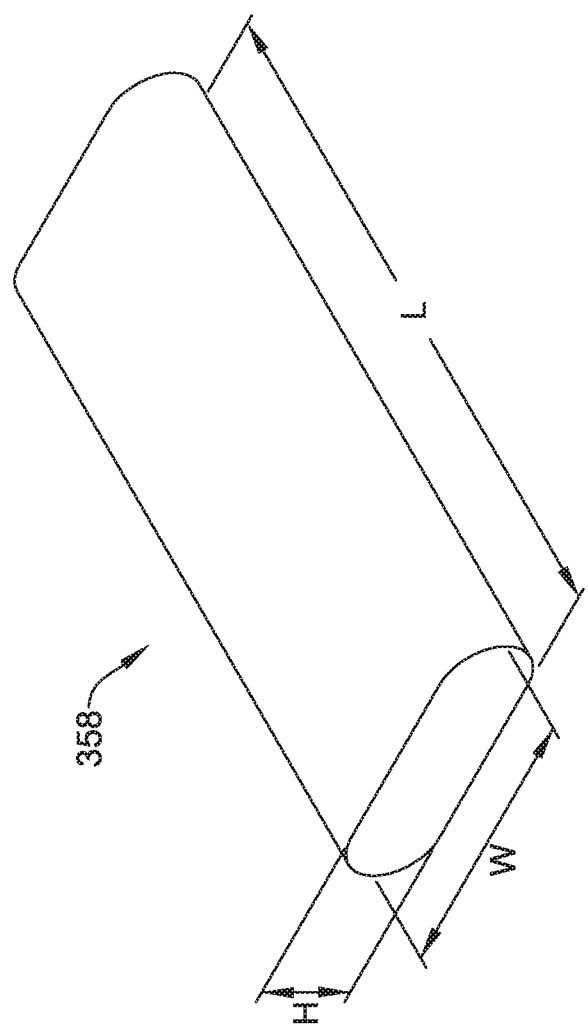

The shocking solid surface electrode 358 may have a generally flattened cross-sectional configuration, although this is not required. For example, referring to FIG. 3E which illustrates a perspective view of the illustrative electrode 358, the solid surface electrode 358 may have a cross-sectional shape that generally takes the form of an oval. The cross-sectional shape may have two curved ends and two parallel sides connecting the curved ends. Other cross-sectional shapes may also be used, including, but not limited to, rectangular, polygonal, circular, square, etc. The solid surface electrode 358 may have a length L that is generally larger than a width W. The width W may be generally larger than a height H of the electrode 358. The length L of the electrode 358 may be in the range of 50 to 110 millimeters (mm), 60 to 100 mm, 70 to 90 mm or about 80 mm. The width W of the electrode 358 may be in the range of 1 to 40 mm, 5 to 35 mm, 10 to 30 mm, 15 to 25 mm, or about 20 mm. The height H of the electrode 358 may be in the range of 0.5 mm to 6 mm, 1 mm to 5 mm, 2 mm to 4 mm, or about 3 mm. The solid surface electrode 358 may have a larger surface area and/or shadow than a typical shocking coil electrode. It is contemplated that increasing the surface area and/or shadow of the shocking electrode 358 may allow the defibrillation threshold to be lowered which may allow the canister, such as canister 12, to have a smaller profile.

In some embodiments, the solid surface electrode 358 may be formed as a subassembly and placed over the lead body 352. Alternatively, the solid surface electrode 358 may be formed as a unitary structure with or otherwise formed over the lead body 352. While not explicitly shown, the solid surface electrode 358 may include a lumen or passageway for receiving a stylet or other delivery aid.

Figure 4A:
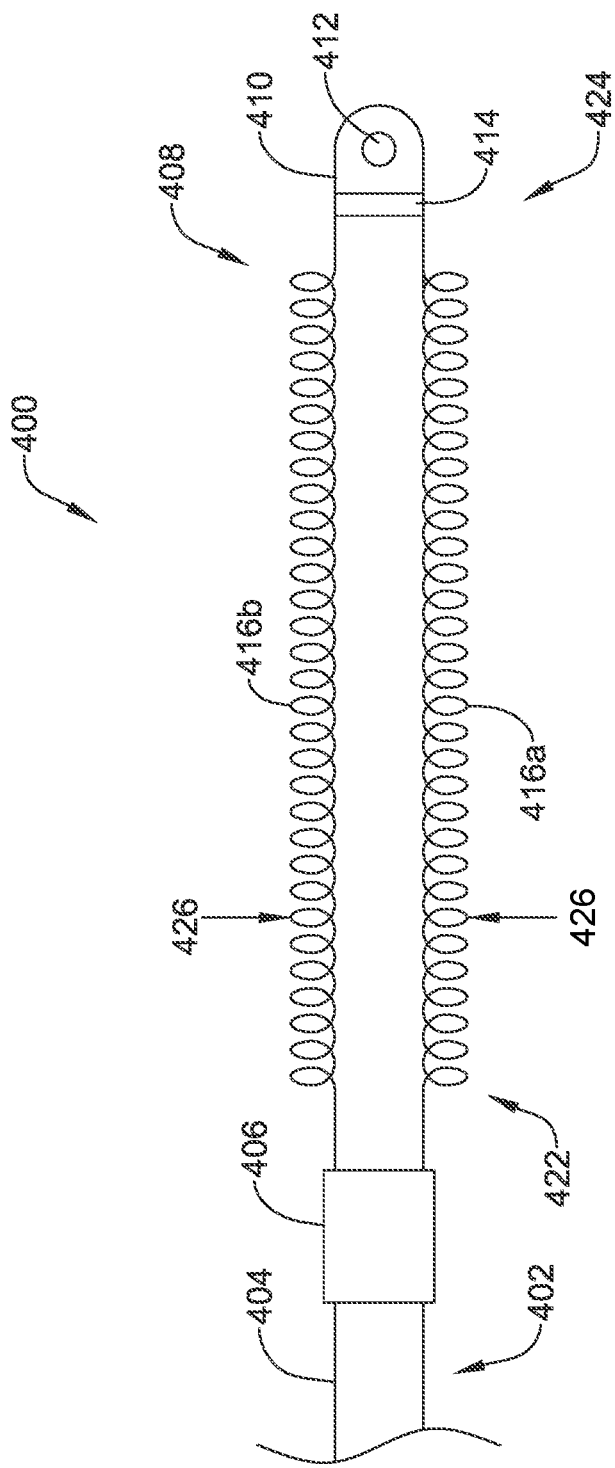
FIGS. 4A-4D show another illustrative electrode for use with an implantable cardiac rhythm management system.
Figure 4B:
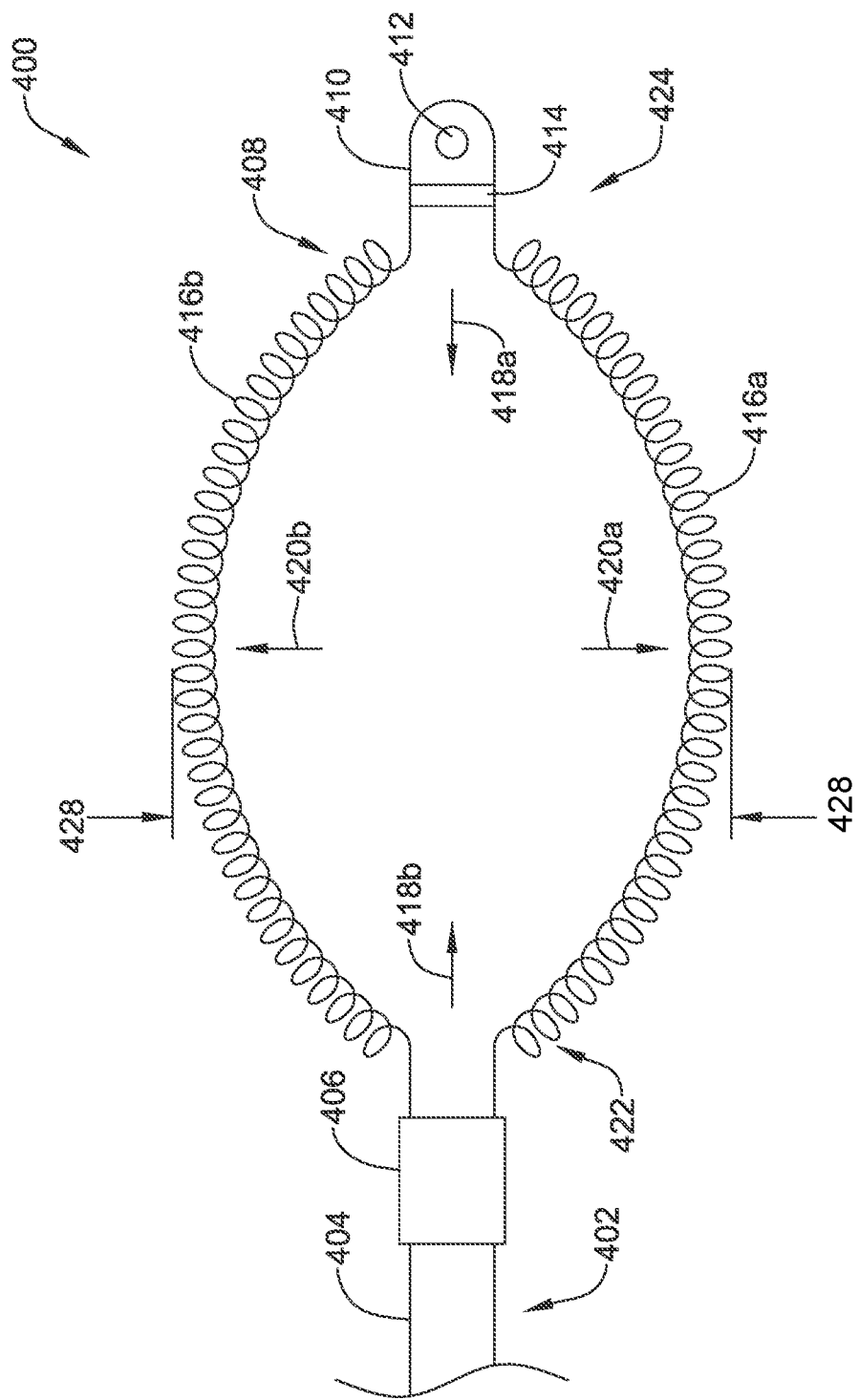

A thin permeable membrane may be positioned over the coil 358 and/or other portions of the lead and electrode assembly 350 to inhibit tissue ingrowth. Coatings, such as, but not limited to expanded polytetrafluoroethylene (ePTFE) may also be applied to the lead and electrode assembly 350, or portions thereof, to facilitate extraction and/or to reduce tissue ingrowth. In some embodiments, one or more of the electrodes 356, 358, 360 may be include a high capacitive coating such as, but not limited to iridium oxide (IrOx), titanium nitride (TiN), or other "fractal" coatings which may be used, for example, to improve electrical performance. The lead and electrode assembly 350, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid FIGS. 4A and 4B show a top view of another illustrative lead and electrode assembly 400 for use with an implantable cardiac rhythm management system, such as, but not limited to the S-ICD System™ from Cameron Health, Inc., and Boston Scientific Corporation described with respect to FIG. 1. In some embodiments, the illustrated assembly 400 may be configured to move between a collapsed or delivery configuration, shown in FIG. 4A and an expanded or implanted configuration, shown in FIG. 4B. However, it is contemplated that the illustrative lead and electrode assembly 400 of FIG. 4A may be both the delivery configuration and the implanted configuration. Similarly, the illustrative lead and electrode assembly 400 of FIG. 4B may be both the delivery configuration and the implanted configuration.

While not explicitly shown, the lead 402 may include a proximal end with a proximal pin which along with additional contacts serves in this example as an electrical contact, which may be separated by insulating material. The lead 402 may be similar in form and function to the lead 302 described above. The proximal end may further include seal plugs. A proximal plug sheath may be provided for a region near the proximal end of the lead 402. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 402 extends from this proximal configuration through an intermediate region 404 to a distal end having a proximal electrode 406, a coil electrode 408, and a distal tip electrode 410. The positioning and/or spacing of the electrodes 406, 408, 410 may be adjusted and/or reconfigured to optimize sensing and/or therapy delivery. For example, both sensing electrodes 406, 410 may be placed proximal to or distal to the coil electrode 408. This is just an example. It is contemplated that the electrodes 406, 408, 410 may be placed beneath the skin and over the ribcage of the patient. In other embodiments, the electrodes 406, 408, 410 may be placed in a substernal location using an implant procedure that may include a xiphoid or sub-xiphoid incision that allows for tunneling along the back side of the sternum. The electrodes 406, 408, 410 may also be placed elsewhere as desired including for example, for use with right sided, anterior-posterior, or other implant positions.

Lead 402 is shown for illustrative purposes, however, other designs and configurations including fewer, more or different electrodes 406, 408, 410, or contacts, may be used. Additional design elements such as bifurcation or other splitting, paddles or other designs may be used instead with an anchoring device attached at the time of implant. The lead 402 is not shown as including a passageway for a stylet to use during introduction, however, a lumen for that purpose may be provided if desired. In the illustrative example, the lead 402 has a body that contains passageways having connectors therein for coupling the proximal contacts to the coil 408, proximal electrode 406, and/or distal electrode 410.

The distal tip electrode 410 is shown with a suture hole 412. The suture hole 412 may be coupled to a base portion 414. Other designs may be used. In some embodiments, a suture hole 412, or other fixation means, may not be required and/or may not be provided.

The coil electrode 408 may be formed from two or more individual coil electrodes 416a, 416b. While the coil electrode 408 is illustrated as including two coil electrodes 416a, 416b, the coil electrode 408 may including any number of individual coil electrodes desired, such as, but not limited to, one, two, three, four, five, or more. Further, in either configuration, the coil electrodes 416a, 416b may be positioned close to one another (e.g. touching) or spaced a distance, as desired. The coil electrode 408 may be affixed to the lead body 402 at its proximal end 422 and its distal end 424. While not explicitly shown, in some embodiments, the lead body 402 may include a portion that extends between the proximal end 422 and the distal end 424 of the coil electrode 408. It is contemplated that the lead body 402 may include a telescoping feature or nested tubular members that allows the proximal end 422 and/or distal end 424 of the coil electrode 408 to be moved along a longitudinal axis of the system 400, such as in the direction of arrows 418a, 418b, shown in FIG. 4B. In other embodiments, the lead body 402 may be disposed within one or both of the coil electrodes 416a, 416b. While not explicitly shown, the coil electrode 408 may include a lumen or passageway for receiving a stylet or other delivery aid.

Each of the coil electrodes 416a, 416b may be formed from a round or flat (ribbon) wire, as desired. In some instances, adjacent windings of the coil electrodes 416a, 416b may be in contact with one another while in other instances adjacent windings may be spread out or spaced a distance from one another, as desired. It is contemplated that the individual coil electrodes 416a, 416b may have the same or similar structure, or may be different, as desired. For example one coil electrode 416a may be more tightly wound than the other 416b. This is just an example.

A thin permeable membrane may be positioned over the coil 408 and/or other portions of the lead and electrode assembly 400 to inhibit tissue ingrowth. A single permeable membrane may surround both coil electrodes 416a, 416b. Alternatively, or additionally, separate membranes may surround each of the coil electrodes 416a, 416b individually. Coatings, such as, but not limited to expanded polytetrafluoroethylene (ePTFE) may also be applied to the lead and electrode assembly 400, or portions thereof, to facilitate extraction and/or to reduce tissue ingrowth. In some embodiments, one or more of the electrodes 406, 408, 410 may be include a high capacitive coating such as, but not limited to iridium oxide (IrOx), titanium nitride (TiN), or other "fractal" coatings which may be used, for example, to improve electrical performance. The lead and electrode assembly 400, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

The coil electrodes 416a, 416b may be actuatable or expandable from a delivery configuration having a first width 426, shown in FIG. 4A, to an implanted configuration having a second larger width 428, as shown in FIG. 4B. While the embodiments shown in FIGS. 4A and 4B are described as movable between two different configurations, it is contemplated the lead and electrode assembly 400 may be fixed in either arrangement. In other words, in some embodiments the electrodes 416a, 416b may be movable relative to one another while in other embodiments, the electrodes 416a, 416b may be in a fixed arrangement relative to one another. It is contemplated that the coil electrode 408, in either the delivery configuration or the implanted configuration, may be similar in size to the coil electrode 308 described above. The coil electrode 408 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

The lead and electrode assembly 400 may be actuated between the delivery configuration and the implanted configuration using any number of deployment mechanisms. In one example, the distal electrode 410 may be secured to the tissue. Once the distal end has been secured, the lead body 402 may be distally advanced to apply a pushing force to the proximal end 422 of the coil electrode 408. This may cause the coil electrodes 416a, 416b to bias outward, for example in directions 420a, 420b, shown in FIG. 4B while also shortening in length, as shown at arrows 418a, 418b. It is contemplated that the same result may be achieved by applying a proximal, or pulling force to the distal end 424 of the coil. In yet another example, the coil electrodes 416a, 416b may be formed in the expanded configuration illustrated in FIG. 4B. The coil electrodes 416a, 416b may be compressed into a lower profile delivery configuration through the application of a biasing force. For example, when the coil electrodes 416a, 416b are disposed within a delivery tool, the delivery tool may maintain the coil electrodes 416a, 416b in a reduced profile configuration.

Figure 4C:
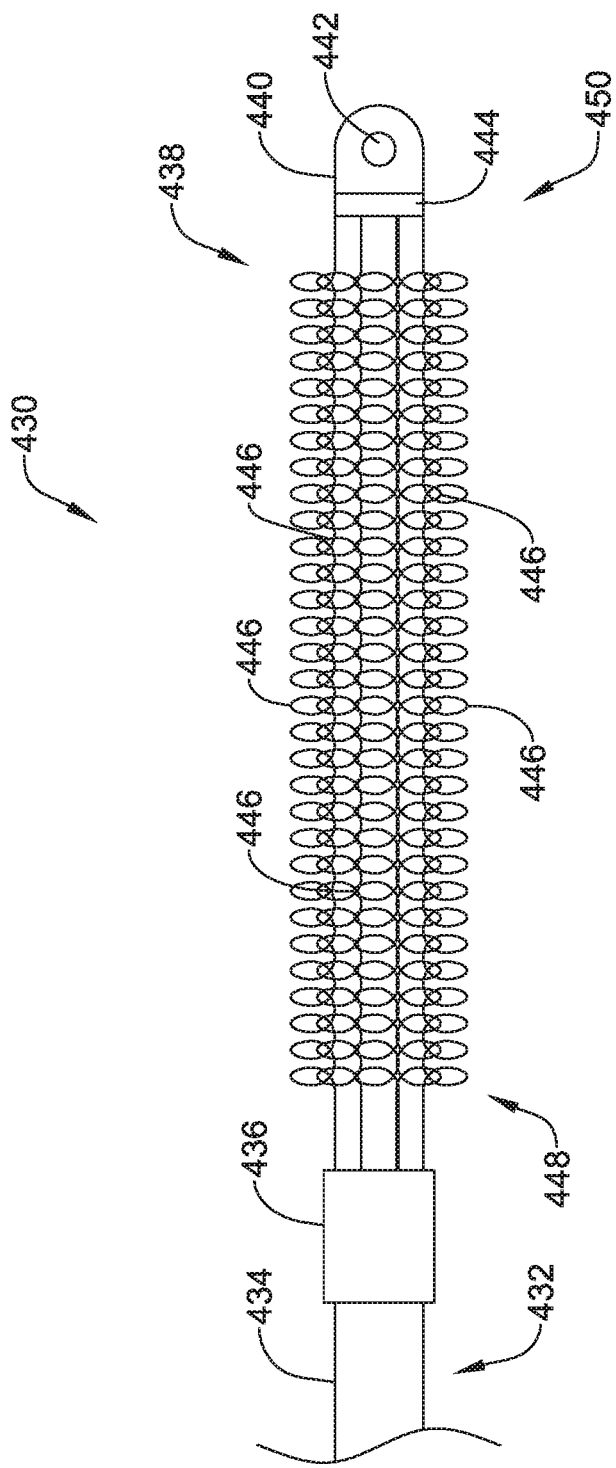

FIG. 4C shows a top view of another illustrative lead and electrode assembly 430 for use with an implantable cardiac rhythm management system, such as, but not limited to the S-ICD System™ from Cameron Health, Inc., and Boston Scientific Corporation described with respect to FIG. 1. While not explicitly shown, the illustrated assembly 430 may be configured to move between a collapsed or delivery configuration and an expanded or implanted configuration such as that described with respect to FIGS. 4A and 4B. However, this is not required. It is contemplated that the illustrative lead and electrode assembly 430 of FIG. 4C may be both the delivery configuration and the implanted configuration.

While not explicitly shown, the lead 432 may include a proximal end with a proximal pin which along with additional contacts serves in this example as an electrical contact, which may be separated by insulating material. The lead 432 may be similar in form and function to the lead 302 described above. The proximal end may further include seal plugs. A proximal plug sheath may be provided for a region near the proximal end of the lead 432. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 432 extends from this proximal configuration through an intermediate region 434 to a distal end having a proximal electrode 436, a coil electrode 438, and a distal tip electrode 440. The positioning and/or spacing of the electrodes 436, 438, 440 may be adjusted and/or reconfigured to optimize sensing and/or therapy delivery. For example, both sensing electrodes 436, 440 may be placed proximal to or distal to the coil electrode 438. It is contemplated that the electrodes 436, 438, 440 may be placed beneath the skin and over the ribcage of the patient. In other embodiments, the electrodes 436, 438, 440 may be placed in a substernal location using an implant procedure that may include a xiphoid or sub-xiphoid incision that allows for tunneling along the back side of the sternum. The electrodes 436, 438, 440 may also be placed elsewhere as desired including for example, for use with right sided, anterior-posterior, or other implant positions.

Lead 432 is shown for illustrative purposes, however, other designs and configurations including fewer, more or different electrodes 436, 438, 440, or contacts, may be used. Additional design elements such as bifurcation or other splitting, paddles or other designs may be used instead with an anchoring device attached at the time of implant. The lead 432 is not shown as including a passageway for a stylet to use during introduction, however, a lumen for that purpose may be provided if desired. In the illustrative example, the lead 432 has a body that contains passageways having connectors therein for coupling the proximal contacts to the coil 438, proximal electrode 436, and/or distal electrode 440.

The distal tip electrode 440 is shown with a suture hole 442. The suture hole 442 may be coupled to a base portion 444. Other designs may be used. In some embodiments, a suture hole 442, or other fixation means, may not be required and/or may not be provided.

The coil electrode 438 may be formed from a plurality of individual coil electrodes 446. While the coil electrode 438 is illustrated as including five coil electrodes 446, the coil electrode 438 may including any number of individual coil electrodes desired, such as, but not limited to, one, two, three, four, five, or more. Further, the coil electrodes 446 may be positioned close to one another (e.g. touching) or spaced a distance, as desired. In some embodiments, the coil electrodes 446 may extend generally parallel to one another and to a longitudinal axis of the lead 432. It is contemplated that the coil electrode 438, may be similar in size to the coil electrode 308 described above. The coil electrode 438 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

The coil electrode 438 may be affixed to the lead body 432 at its proximal end 448 and its distal end 450. While not explicitly shown, in some embodiments, the lead body 432 may include a portion that extends between the proximal end 448 and the distal end 450 of the coil electrode 438. In other embodiments, the lead body 432 may be disposed within one or more of the coil electrodes 446. While not explicitly shown, the coil electrode 438 may include a lumen or passageway for receiving a stylet or other delivery aid.

Each of the coil electrodes 446 may be formed from a round or flat (ribbon) wire, as desired. In some instances, adjacent windings of the coil electrodes 446 may be in contact with one another while in other instances adjacent windings may be spread out or spaced a distance from one another, as desired. It is contemplated that the individual coil electrodes 446 may have the same or similar structure, or may be different, as desired. For example one coil electrode may be more tightly wound than another. This is just an example.

A thin permeable membrane may be positioned over the coil 438 and/or other portions of the lead and electrode assembly 430 to inhibit tissue ingrowth. In some embodiments, a single permeable membrane may surround the plurality of coil electrodes 446. Alternatively, or additionally, separate membranes may surround each of the coil electrodes 446 individually. Coatings, such as, but not limited to expanded polytetrafluoroethylene (ePTFE) may also be applied to the lead and electrode assembly 430, or portions thereof, to facilitate extraction and/or to reduce tissue ingrowth. In some embodiments, one or more of the electrodes 436, 438, 440 may be include a high capacitive coating such as, but not limited to iridium oxide (IrOx), titanium nitride (TiN), or other "fractal" coatings which may be used, for example, to improve electrical performance. The lead and electrode assembly 430, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

Figure 4D:
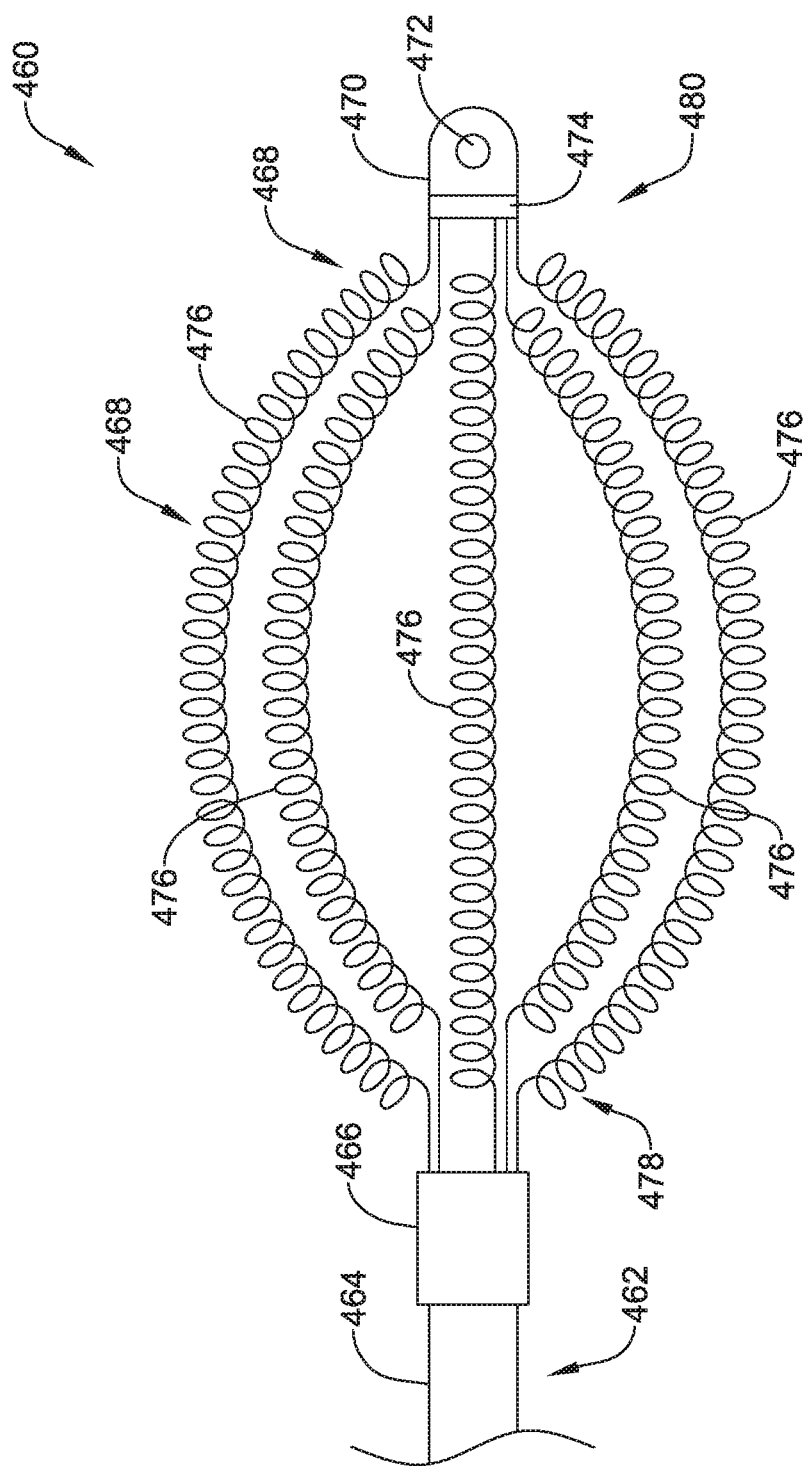

FIG. 4D shows a top view of another illustrative lead and electrode assembly 460 for use with an implantable cardiac rhythm management system, such as, but not limited to the S-ICD System™ from Cameron Health, Inc., and Boston Scientific Corporation described with respect to FIG. 1. While not explicitly shown, the illustrated assembly 460 may be configured to move between a collapsed or delivery configuration and an expanded or implanted configuration such as that described with respect to FIGS. 4A and 4B. However, this is not required. It is contemplated that the illustrative lead and electrode assembly 460 of FIG. 4D may be both the delivery configuration and the implanted configuration.

While not explicitly shown, the lead 462 may include a proximal end with a proximal pin which along with additional contacts serves in this example as an electrical contact, which may be separated by insulating material. The lead 462 may be similar in form and function to the lead 302 described above. The proximal end may further include seal plugs. A proximal plug sheath may be provided for a region near the proximal end of the lead 462. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 462 extends from this proximal configuration through an intermediate region 464 to a distal end having a proximal electrode 466, a coil electrode 468, and a distal tip electrode 470. The positioning and/or spacing of the electrodes 466, 468, 470 may be adjusted and/or reconfigured to optimize sensing and/or therapy delivery. For example, both sensing electrodes 466, 470 may be placed proximal to or distal to the coil electrode 468. It is contemplated that the electrodes 466, 468, 470 may be placed beneath the skin and over the ribcage of the patient. In other embodiments, the electrodes 466, 468, 470 may be placed in a substernal location using an implant procedure that may include a xiphoid or sub-xiphoid incision that allows for tunneling along the back side of the sternum. The electrodes 466, 468, 470 may also be placed elsewhere as desired including for example, for use with right sided, anterior-posterior, or other implant positions.

Lead 462 is shown for illustrative purposes, however, other designs and configurations including fewer, more or different electrodes 466, 468, 470, or contacts, may be used. Additional design elements such as bifurcation or other splitting, paddles or other designs may be used instead with an anchoring device attached at the time of implant. The lead 462 is not shown as including a passageway for a stylet to use during introduction, however, a lumen for that purpose may be provided if desired. In the illustrative example, the lead 462 has a body that contains passageways having connectors therein for coupling the proximal contacts to the coil 468, proximal electrode 466, and/or distal electrode 470.

The distal tip electrode 470 is shown with a suture hole 472. The suture hole 472 may be coupled to a base portion 474. Other designs may be used. In some embodiments, a suture hole 472, or other fixation means, may not be required and/or may not be provided.

The coil electrode 468 may be formed from a plurality of individual coil electrodes 476. While the coil electrode 468 is illustrated as including five coil electrodes 476, the coil electrode 468 may including any number of individual coil electrodes desired, such as, but not limited to, one, two, three, four, five, or more. Further, the coil electrodes 476 may be positioned close to one another (e.g. touching) or spaced a distance, as desired. In some embodiments, some or all of the coil electrodes 476 may have a generally curved configuration such that the coil electrode 468 is generally oval in its overall shape. This is not required. The coil electrode 468 may take any shape desired. It is contemplated that the coil electrode 468, may be similar in size to the coil electrode 308 described above. The coil electrode 468 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

The coil electrode 468 may be affixed to the lead body 462 at its proximal end 478 and its distal end 480. While not explicitly shown, in some embodiments, the lead body 462 may include a portion that extends between the proximal end 478 and the distal end 480 of the coil electrode 468. In other embodiments, the lead body 462 may be disposed within one or more of the coil electrodes 476. While not explicitly shown, the coil electrode 468 may include a lumen or passageway for receiving a stylet or other delivery aid.

Each of the coil electrodes 476 may be formed from a round or flat (ribbon) wire, as desired. In some instances, adjacent windings of the coil electrodes 476 may be in contact with one another while in other instances adjacent windings may be spread out or spaced a distance from one another, as desired. It is contemplated that the individual coil electrodes 476 may have the same or similar structure, or may be different, as desired. For example one coil electrode may be more tightly wound than another. This is just an example.

A thin permeable membrane may be positioned over the coil 468 and/or other portions of the lead and electrode assembly 460 to inhibit tissue ingrowth. In some embodiments, a single permeable membrane may surround the plurality of coil electrodes 476. Alternatively, or additionally, separate membranes may surround each of the coil electrodes 476 individually. Coatings, such as, but not limited to expanded polytetrafluoroethylene (ePTFE) may also be applied to the lead and electrode assembly 460, or portions thereof, to facilitate extraction and/or to reduce tissue ingrowth. In some embodiments, one or more of the electrodes 466, 468, 470 may be include a high capacitive coating such as, but not limited to iridium oxide (IrOx), titanium nitride (TiN), or other "fractal" coatings which may be used, for example, to improve electrical performance. The lead and electrode assembly 460, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

Figure 5A:
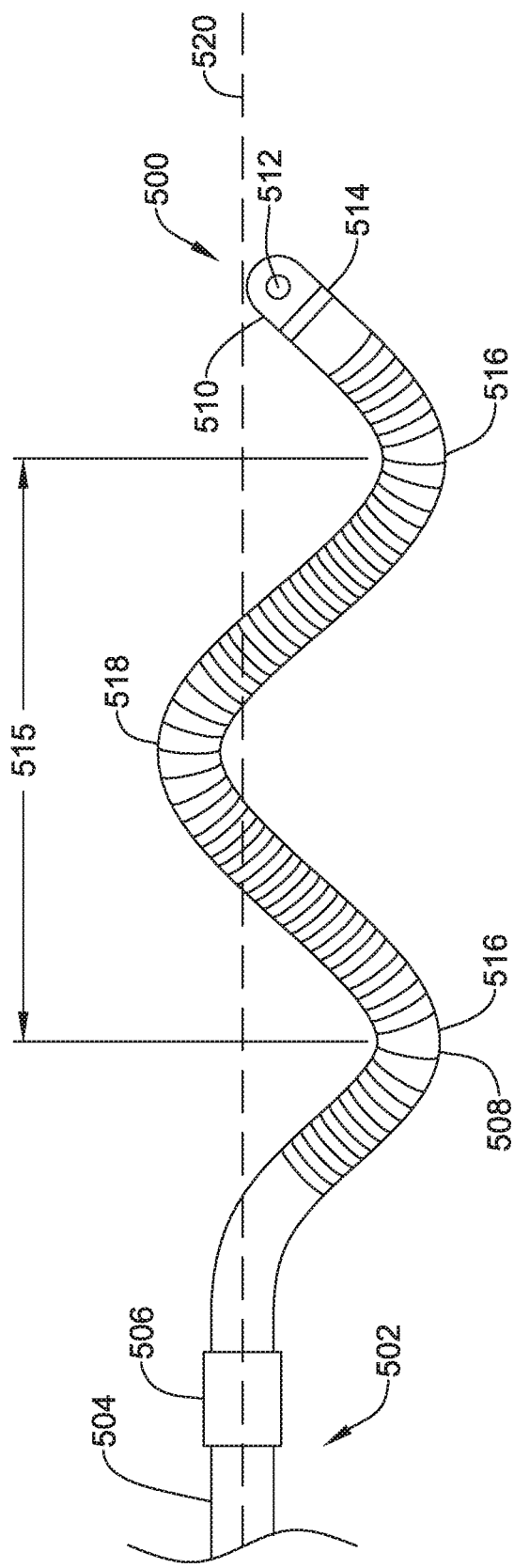
FIGS. 5A-5B show another illustrative electrode for use with an implantable cardiac rhythm management system.

FIG. 5A shows a top view of another illustrative lead and electrode assembly 500 for use with an implantable cardiac rhythm management system, such as, but not limited to the S-ICD System™ from Cameron Health, Inc., and Boston Scientific Corporation described with respect to FIG. 1. While not explicitly shown, the illustrated assembly 500 may be configured to move between a delivery configuration and an implanted configuration. For example, the illustrated assembly 500 may be delivered in a generally linear configuration and placed into the oscillating configuration shown in FIG. 5A after deployment. This may allow a smaller delivery tool to be used for insertion of the lead assembly 500. However, this is not required. It is contemplated that the illustrative lead and electrode assembly 500 may be delivered in the oscillating or curved configuration.

While not explicitly shown, the lead 502 may include a proximal end with a proximal pin which along with additional contacts serves in this example as an electrical contact, which may be separated by insulating material. The lead 502 may be similar in form and function to the lead 302 described above. The proximal end may further include seal plugs. A proximal plug sheath may be provided for a region near the proximal end of the lead 502. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 502 extends from this proximal configuration through an intermediate region 504 to a distal end having a proximal electrode 506, a coil electrode 508, and a distal tip electrode 510. The positioning and/or spacing of the electrodes 506, 508, 510 may be adjusted and/or reconfigured to optimize sensing and/or therapy delivery. For example, both sensing electrodes 506, 510 may be placed proximal or distal to the coil electrode 508. This is just an example. It is contemplated that the electrodes 506, 508, 510 may be placed beneath the skin and over the ribcage of the patient. In other embodiments, the electrodes 506, 508, 510 may be placed in a sub sternal location using an implant procedure that may include a xiphoid or subxiphoid incision that allows for tunneling along the back side of the sternum. The electrodes 506, 508, 510 may also be placed elsewhere as desired including for example, for use with right sided, anterior-posterior, or other implant positions.

Lead 502 is shown for illustrative purposes, however, other designs and configurations including fewer, more or different electrodes 506, 508, 510, or contacts, may be used. Additional design elements such as bifurcation or other splitting, paddles or other designs may be used instead with an anchoring device attached at the time of implant. The lead 502 is not shown as including a passageway for a stylet to use during introduction, however, a lumen for that purpose may be provided if desired. In the illustrative example, the lead 502 has a body that contains passageways having connectors therein for coupling the proximal contacts to the coil 508, proximal electrode 506, and/or distal electrode 510.

The distal tip electrode 510 is shown with a suture hole 512. The suture hole 512 may be coupled to a base portion 514. Other designs may be used. In some embodiments, a suture hole 512, or other fixation means, may not be required and/or may not be provided.

The coil electrode 508 have a generally oscillating shape. For example, the coil electrode 508 may include one or more oscillations 515 each having a peak 516 and a valley 518. The oscillations 515 may be uniformly positioned along the longitudinal axis 520 of the assembly 500 along a least a portion of the length of the coil electrode 508. In such an instance, the peak 516 and valley 518 may have the same "height" or peak amplitude (as measured from the longitudinal axis 520). Alternatively, or additionally, the oscillations may be shifted from the longitudinal axis 520 such that either the peak 516 or the valley 518 has a greater peak amplitude than the other along a least a portion of the length of the coil electrode 508. The frequency of the oscillations 515 may also be varied. For example, the frequency of the oscillations 515 may be increased such that there are more oscillations over a similar length. It is contemplated that the coil electrode 508 may include less than one, one, two, three, four, five, or more oscillations, as desired. It is further contemplated that the frequency of the oscillations 515 may be varied along the length of a coil electrode 508. Any combination of frequency, peak amplitude, and/or offsets from the longitudinal axis 520 may be used to arrive at the desired shape.

It is contemplated that the coil electrode 508, or the shadow of the coil electrode 508, may be similar in size to the coil electrode 308 described above. The coil electrode 508 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

A thin permeable membrane may be positioned over the coil 508 and/or other portions of the lead and electrode assembly 500 to inhibit tissue ingrowth. Coatings, such as, but not limited to expanded polytetrafluoroethylene (ePTFE) may also be applied to the lead and electrode assembly 500, or portions thereof, to facilitate extraction and/or to reduce tissue ingrowth. In some embodiments, one or more of the electrodes 506, 508, 510 may be include a high capacitive coating such as, but not limited to, iridium oxide (IrOx), titanium nitride (TiN), or other "fractal" coatings which may be used, for example, to improve electrical performance. The lead and electrode assembly 500, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

In some embodiments, the coil electrode 508 may be delivered in a straightened, or generally linear, configuration. This may allow the assembly 500 to be implanted using a smaller profile delivery device. In one example, the distal electrode 510 may be secured to the tissue and subsequently the lead body 502 may be distally advanced to apply a pushing force to the proximal end region of the coil electrode 508. This may cause the coil electrode 508 to wind back and forth, as shown in FIG. 5A, while also shortening in length. It is contemplated that the same result may be achieved by fixing the proximal end and applying a proximal, or pulling force to the distal end of the coil electrode 508. In yet another example, the coil electrode 508 may be formed in the oscillating configuration illustrated in FIG. 5A. The coil electrode 508 may be compressed into a lower profile delivery configuration through the application of a biasing force. For example, when the coil electrode 508 are disposed within a delivery tool, the delivery tool may maintain the coil electrode 508 in a reduced profile configuration (e.g. elongated or compressed). In yet another embodiment, the coil electrode 508 may be implanted in its oscillating configuration using a delivery tool wide enough to house the coil electrode 508 in its oscillating configuration.

Figure 5B:
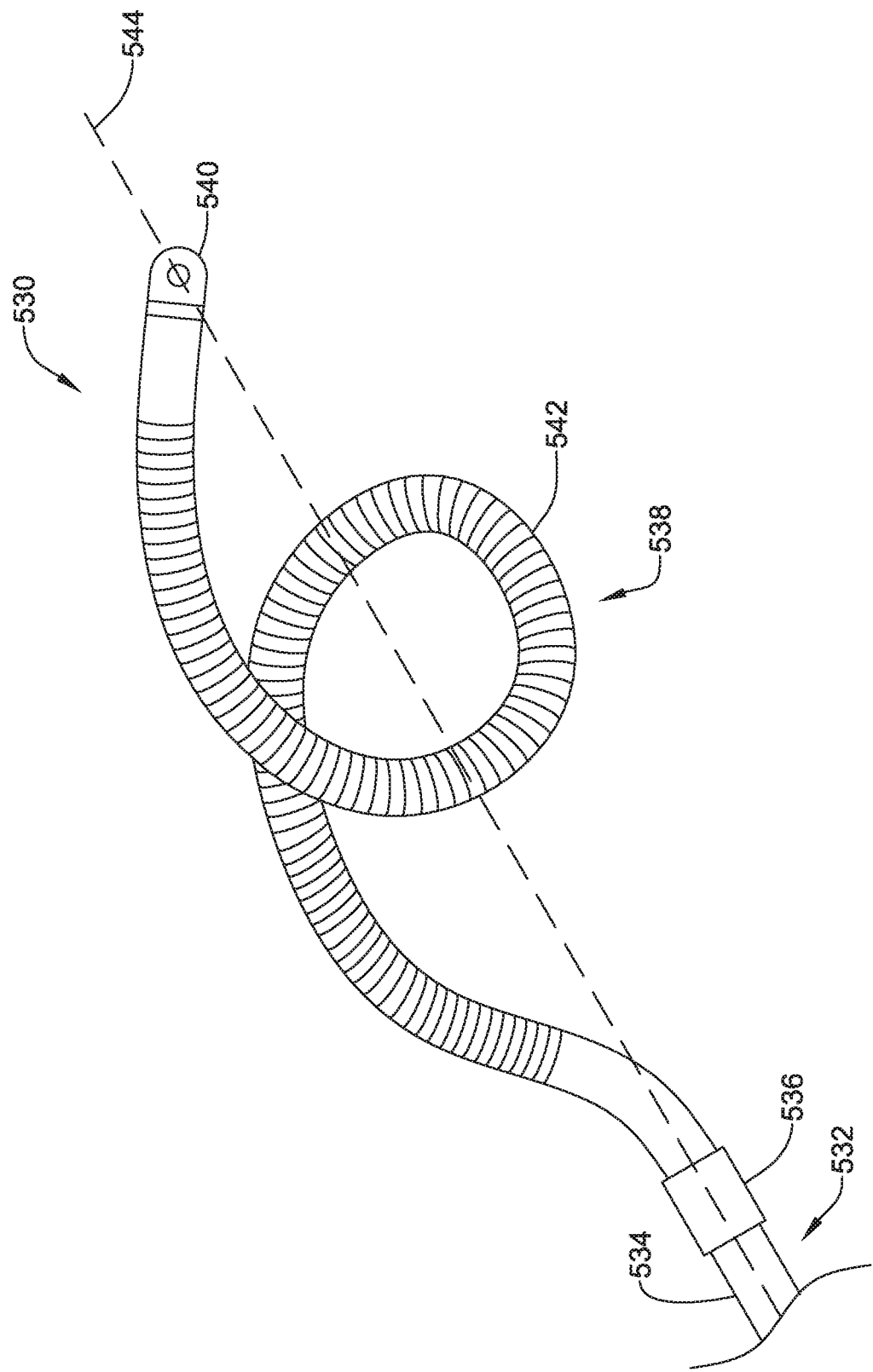

FIG. 5B shows a top view of another illustrative lead and electrode assembly 530 for use with an implantable cardiac rhythm management system, such as, but not limited to the S-ICD System™ from Cameron Health, Inc., and Boston Scientific Corporation described with respect to FIG. 1. While not explicitly shown, the illustrated assembly 530 may be configured to move between a delivery configuration and an implanted configuration. For example, the illustrated assembly 530 may be delivered in a generally linear configuration and placed into the helical configuration shown in FIG. 5B after deployment. This may allow a smaller delivery tool to be used for insertion of the lead assembly 530. However, this is not required. It is contemplated that the illustrative lead and electrode assembly 530 may be delivered in the helical configuration.

While not explicitly shown, the lead 532 may include a proximal end with a proximal pin which along with additional contacts serves in this example as an electrical contact, which may be separated by insulating material. The lead 532 may be similar in form and function to the lead 302 described above. The proximal end may further include seal plugs. A proximal plug sheath may be provided for a region near the proximal end of the lead 532. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 532 extends from this proximal configuration through an intermediate region 534 to a distal end having a proximal electrode 536, a coil electrode 538, and a distal tip electrode 540. The positioning and/or spacing of the electrodes 536, 538, 540 may be adjusted and/or reconfigured to optimize sensing and/or therapy delivery. For example, both sensing electrodes 536, 540 may be placed proximal or distal to the coil electrode 538. This is just an example. It is contemplated that the electrodes 536, 538, 540 may be placed beneath the skin and over the ribcage of the patient. In other embodiments, the electrodes 536, 538, 540 may be placed in a sub sternal location using an implant procedure that may include a xiphoid or subxiphoid incision that allows for tunneling along the back side of the sternum. The electrodes 536, 538, 540 may also be placed elsewhere as desired including for example, for use with right sided, anterior-posterior, or other implant positions.

Lead 532 is shown for illustrative purposes, however, other designs and configurations including fewer, more or different electrodes 536, 538, 540, or contacts, may be used. Additional design elements such as bifurcation or other splitting, paddles or other designs may be used instead with an anchoring device attached at the time of implant. The lead 532 is not shown as including a passageway for a stylet to use during introduction, however, a lumen for that purpose may be provided if desired. In the illustrative example, the lead 532 has a body that contains passageways having connectors therein for coupling the proximal contacts to the coil 538, proximal electrode 536, and/or distal electrode 540.

While not explicitly shown, the distal tip electrode 540 may include a suture hole similar to those described above. Other designs may be used. In some embodiments, a suture hole, or other fixation means, may not be required and/or may not be provided.

The coil electrode 538 have a generally helical shape. For example, the coil electrode 538 may be wound into a helix 542. The helix 524 may have a three dimensional shape which may facilitate better contact with the facial plane. The coil electrode 538 forming the helix 542 may have a generally round or a generally flat (e.g. rectangular) cross-sectional shape, as desired. However, other cross-sectional shapes may be used. The helix 542 may have a closed pitch, or in other words, adjacent windings may contact one another. Alternatively, the helix 542 may have an open pitch such that adjacent windings are spaced a distance from one another. The pitch may be uniform or varied along a length of the coil electrode. A varied pitch may be gradual tapered changes in pitch or abrupt or step-wise changes in pitch. The helix 542 may include any number of windings desired, such as, but not limited to less than one, one, two, three, four, or more.

The windings of the helix 542 may be uniformly positioned (e.g. centered) along the longitudinal axis 544 of the assembly 530 along a least a portion of the length of the coil electrode 538. Alternatively, or additionally, the helix 542 may be shifted from the longitudinal axis 544 such the center of the helix 542 is offset from the longitudinal axis 544 along a least a portion of the length of the coil electrode 538. Any combination of pitch, winding diameter, and/or offsets from the longitudinal axis 544 may be used to arrive at the desired shape.

It is contemplated that the coil electrode 538, or the shadow of the coil electrode 538, may be similar in size to the coil electrode 308 described above. The coil electrode 538 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

A thin permeable membrane may be positioned over the coil 538 and/or other portions of the lead and electrode assembly 530 to inhibit tissue ingrowth. Coatings, such as, but not limited to expanded polytetrafluoroethylene (ePTFE) may also be applied to the lead and electrode assembly 530, or portions thereof, to facilitate extraction and/or to reduce tissue ingrowth. In some embodiments, one or more of the electrodes 536, 538, 540 may be include a high capacitive coating such as, but not limited to iridium oxide (IrOx), titanium nitride (TiN), or other "fractal" coatings which may be used, for example, to improve electrical performance. The lead and electrode assembly 530, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

In some embodiments, the coil electrode 538 may be delivered in a straightened, or generally linear, configuration. This may allow the assembly 530 to be implanted using a smaller profile delivery device. In one example, the distal electrode 540 may be secured to the tissue and subsequently the lead body 532 may be distally advanced to apply a pushing force to the proximal end region of the coil electrode 538. This may cause the coil electrode 538 to coil, as shown in FIG. 5B while also shortening in length, as shown at arrows 418a, 418b. It is contemplated that the same result may be achieved by fixing the proximal end and applying a proximal, or pulling force to the distal end of the coil electrode 538. In yet another example, the coil electrode 538 may be formed in the helical configuration illustrated in FIG. 5B. The coil electrode 538 may be compressed (e.g. elongated or stretched) into a lower profile delivery configuration through the application of a biasing force. For example, when the coil electrode 538 are disposed within a delivery tool, the delivery tool may maintain the coil electrode 538 in a reduced profile configuration (e.g. elongated, compressed, stretched, etc.). In yet another embodiment, the coil electrode 538 may be implanted in its helical configuration using a delivery tool wide enough to house the coil electrode 538 in its helical configuration.

Figure 6A:
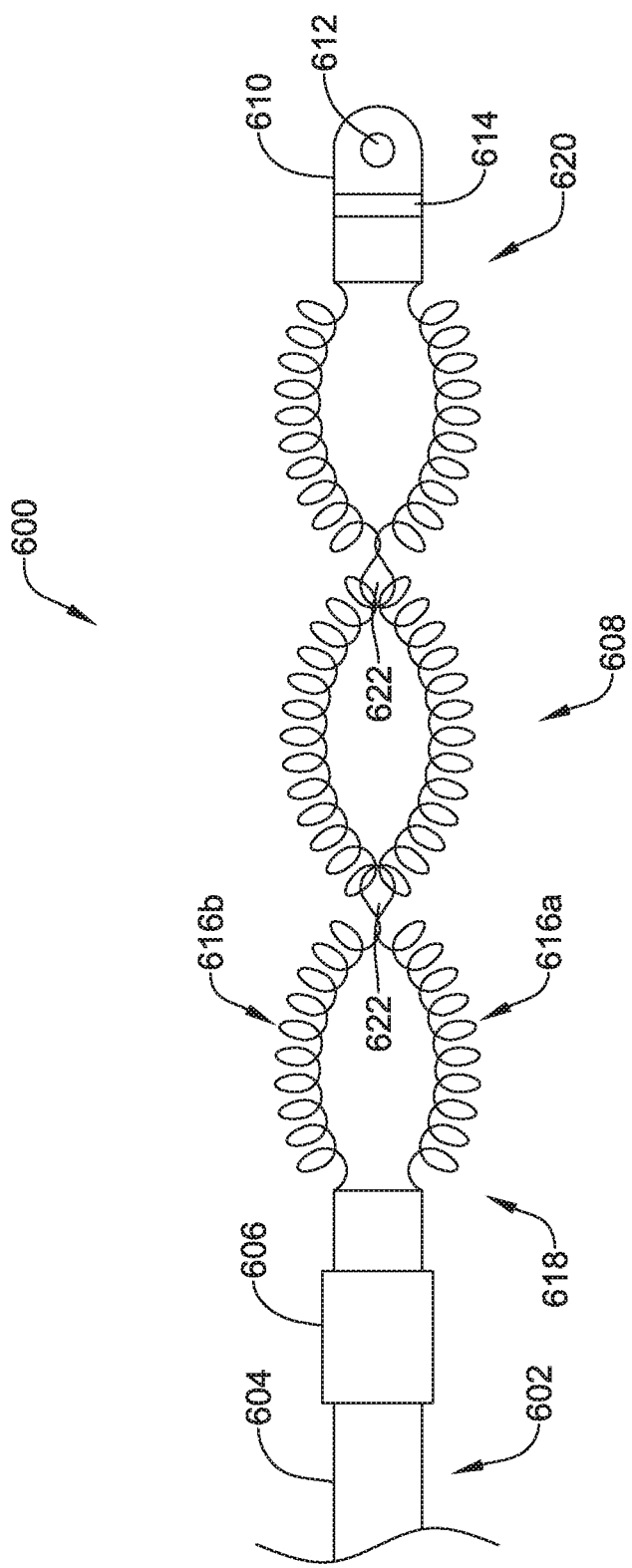
FIGS. 6A-6B show another illustrative electrode for use with an implantable cardiac rhythm management system.
Figure 6B:
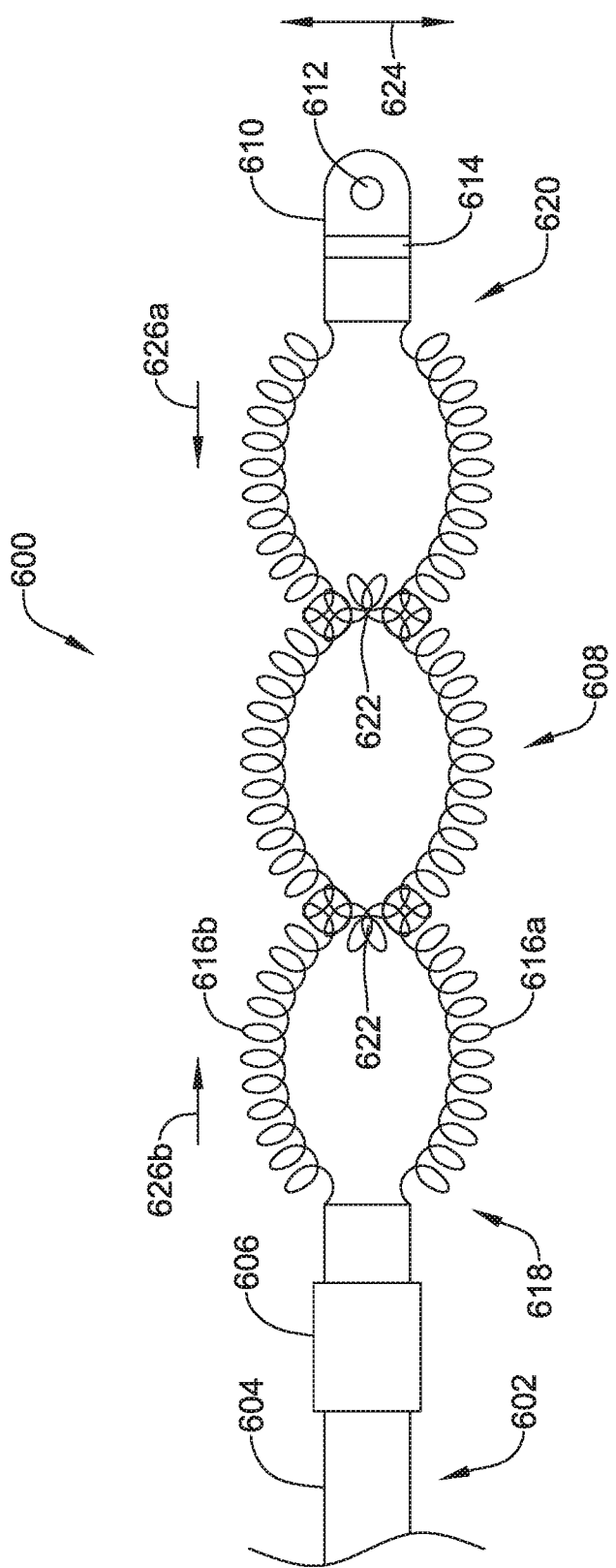

FIGS. 6A and 6B show a top view of another illustrative lead and electrode assembly 600 for use with an implantable cardiac rhythm management system, such as, but not limited to the S-ICD System™ from Cameron Health, Inc., and Boston Scientific Corporation described with respect to FIG. 1. In some embodiments, the illustrated assembly 600 may be configured to move between a collapsed or delivery configuration, shown in FIG. 6A and an expanded or implanted configuration, shown in FIG. 6B. However, it is contemplated that the illustrative lead and electrode assembly 600 of FIG. 6A may be both the delivery configuration and the implanted configuration. Similarly, the illustrative lead and electrode assembly 600 of FIG. 6B may be both the delivery configuration and the implanted configuration.

While not explicitly shown, the lead 602 may include a proximal end with a proximal pin which along with additional contacts serves in this example as an electrical contact, which may be separated by insulating material. The lead 602 may be similar in form and function to the lead 302 described above. The proximal end may further include seal plugs. A proximal plug sheath may be provided for a region near the proximal end of the lead 602. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 602 extends from this proximal configuration through an intermediate region 604 to a distal end having a proximal electrode 606, a coil electrode 608, and a distal tip electrode 610. The positioning and/or spacing of the electrodes 606, 608, 610 may be adjusted and/or reconfigured to optimize sensing and/or therapy delivery. For example, both sensing electrodes 606, 610 may be placed proximal to or distal to the coil electrode 608. This is just an example. It is contemplated that the electrodes 606, 608, 610 may be placed beneath the skin and over the ribcage of the patient. In other embodiments, the electrodes 606, 608, 610 may be placed in a sub sternal location using an implant procedure that may include a xiphoid or subxiphoid incision that allows for tunneling along the back side of the sternum. The electrodes 606, 608, 610 may also be placed elsewhere as desired including for example, for use with right sided, anterior-posterior, or other implant positions.

Lead 602 is shown for illustrative purposes, however, other designs and configurations including fewer, more or different electrodes 606, 608, 610, or contacts, may be used. Additional design elements such as bifurcation or other splitting, paddles or other designs may be used instead with an anchoring device attached at the time of implant. The lead 602 is not shown as including a passageway for a stylet to use during introduction, however, a lumen for that purpose may be provided if desired. In the illustrative example, the lead 602 has a body that contains passageways having connectors therein for coupling the proximal contacts to the coil 608, proximal electrode 606, and/or distal electrode 610.

The distal tip electrode 610 is shown with a suture hole 612. The suture hole 612 may be coupled to a base portion 614. Other designs may be used. In some embodiments, a suture hole 612, or other fixation means, may not be required and/or may not be provided.

The coil electrode 608 may be formed from two or more individual coil electrodes 616a, 616b. While the coil electrode 608 is illustrated as including two coil electrodes 616a, 616b, the coil electrode 608 may including any number of individual coil electrodes desired, such as, but not limited to, one, two, three, four, five, or more. The coil electrodes 616a, 616b may have a generally two dimensional oscillatory configuration, similar in form and function to the oscillatory configuration described with respect to FIG. 5A. Alternatively, the coil electrodes 616a, 616b may have a generally three dimensional helical configuration, similar in form and function to the helical configuration described with respect to FIG. 5B. The coil electrodes 616a, 616b may be wound or coiled in opposite directions such that the coil electrodes 616a, 616b cross at cross points 622. In some embodiments, the coil electrodes 616a, 616b may be secured to one another at the cross points 622, although this is not required. It is contemplated that the coil electrode 608 may include any number of cross points 622 desired, such as, but not limited to one, two, three, four, or more.

The coil electrode 608 may be affixed to the lead body 602 at its proximal end 618 and its distal end 620. While not explicitly shown, in some embodiments, the lead body 602 may include a portion that extends between the proximal end 618 and the distal end 620 of the coil electrode 608. It is contemplated that the lead body 602 may include a telescoping feature or nested tubular members that allows the proximal end 618 and/or distal end 620 of the coil electrode 608 to be moved along a longitudinal axis of the system 600, such as in the direction of arrows 626a, 626b, shown in FIG. 6B. In other embodiments, the lead body 602 may be disposed within one or both of the coil electrodes 616a, 616b. While not explicitly shown, the coil electrode 608 may include a lumen or passageway for receiving a stylet or other delivery aid.

Each of the coil electrodes 616a, 616b may be formed from a round or flat (ribbon) wire, as desired. In some instances, adjacent windings of the coil electrodes 616a, 616b may be in contact with one another while in other instances adjacent windings may be spread out or spaced a distance from one another, as desired. It is contemplated that the individual coil electrodes 616a, 616b may have the same or similar structure, or may be different, as desired. For example one coil electrode 616a may be more tightly wound than the other 616b. This is just an example.

A thin permeable membrane may be positioned over the coil 608 and/or other portions of the lead and electrode assembly 600 to inhibit tissue ingrowth. A single permeable membrane may surround both coil electrodes 616a, 616b. Alternatively, or additionally, separate membranes may surround each of the coil electrodes 616a, 616b individually. Coatings, such as, but not limited to expanded polytetrafluoroethylene (ePTFE) may also be applied to the lead and electrode assembly 600, or portions thereof, to facilitate extraction and/or to reduce tissue ingrowth. In some embodiments, one or more of the electrodes 606, 608, 610 may be include a high capacitive coating such as, but not limited to iridium oxide (IrOx), titanium nitride (TiN), or other "fractal" coatings which may be used, for example, to improve electrical performance. The lead and electrode assembly 600, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

The coil electrodes 616a, 616b may be actuatable or expandable from a delivery configuration having a first width, shown in FIG. 6A, to an implanted configuration having a second larger width 624, as shown in FIG. 6B. For example, the second width 624 may be 2-8 times larger across than the width of the shaft 604 and/or the non-expanded configuration of the coils shown by FIG. 6A.

While the embodiments shown in FIGS. 6A and 6B are described as movable between two different configurations, it is contemplated that the lead and electrode assembly 600 may be fixed in either arrangement. In other words, in some embodiments the electrodes 616a, 616b may be movable relative to one another while in other embodiments, the electrodes 616a, 616b may be in a fixed arrangement relative to one another. It is contemplated that the coil electrode 608, in either the delivery configuration or the implanted configuration, may be similar in size to the coil electrode 308 described above. The coil electrode 608 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

The lead and electrode assembly 600 may be actuated between the delivery configuration and the implanted configuration using any number of deployment mechanisms. In one example, the distal electrode 610 may be secured to the tissue. Once the distal end has been secured, the lead body 602 may be distally advanced to apply a pushing force to the proximal end 618 of the coil electrode 608. This may cause the coil electrodes 616a, 616b to bias outward, as shown at arrow 624 in FIG. 6B while also shortening in length, as shown at arrows 626a, 626b. It is contemplated that the same result may be achieved by applying a proximal, or pulling force to the distal end 620 of the coil. In yet another example, the coil electrodes 616a, 616b may be formed in the expanded configuration illustrated in FIG. 6B. The coil electrodes 616a, 616b may be compressed into a lower profile delivery configuration through the application of a biasing force. For example, when the coil electrodes 616a, 616b are disposed within a delivery tool, the delivery tool may maintain the coil electrodes 616a, 616b in a reduced profile configuration.

Figure 7:
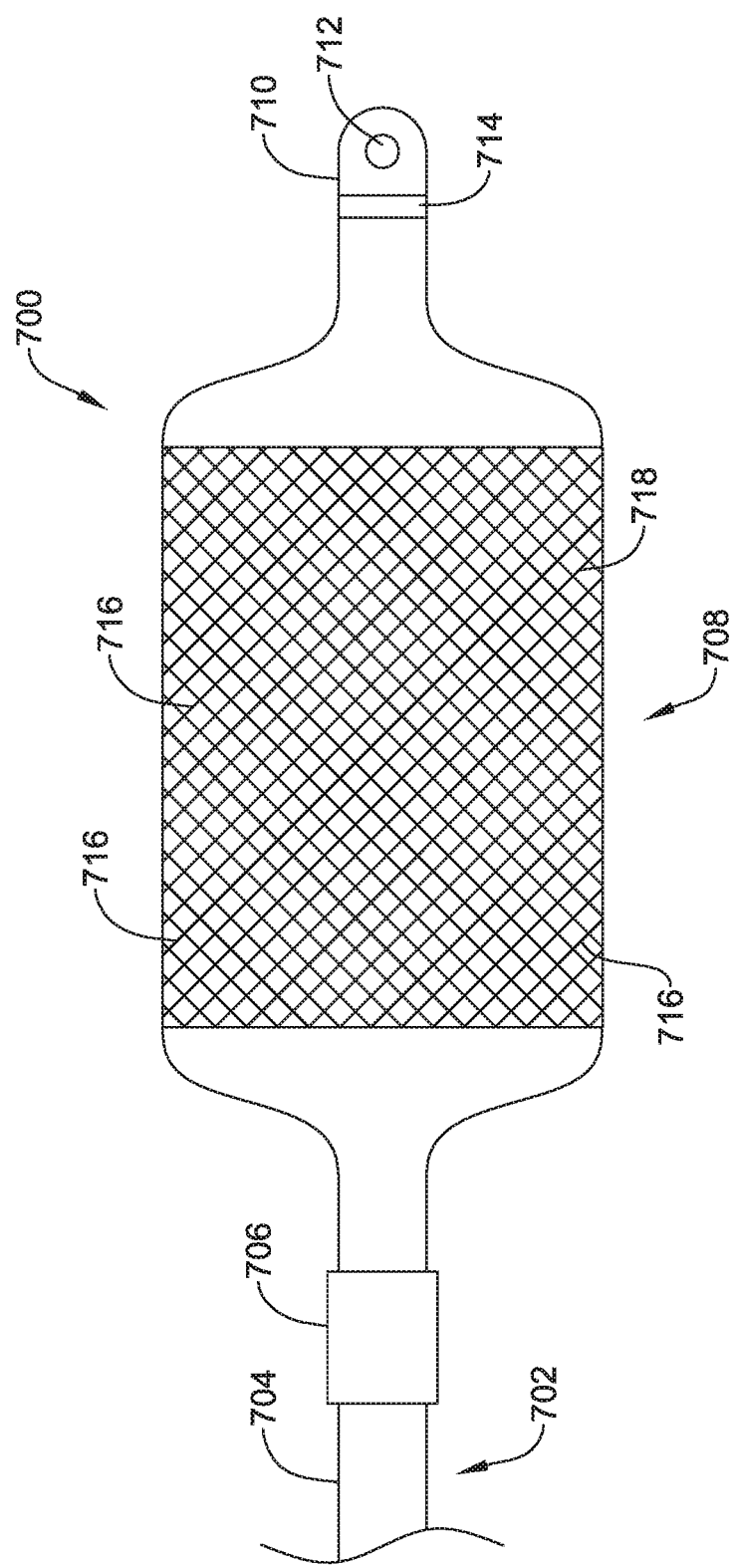
FIG. 7 shows another illustrative electrode for use with an implantable cardiac rhythm management system.

FIG. 7 shows a top view of another illustrative lead and electrode assembly 700 for use with an implantable cardiac rhythm management system, such as, but not limited to the S-ICD System™ from Cameron Health, Inc., and Boston Scientific Corporation described with respect to FIG. 1. While not explicitly shown, the illustrated assembly 700 may be configured to move between a delivery configuration and an implanted configuration. For example, the illustrated assembly 700 may be delivered in a generally collapsed configuration (e.g. rolled) and placed into the configuration shown in FIG. 7 after deployment. This may allow a smaller delivery tool to be used for insertion of the lead assembly 700. However, this is not required. It is contemplated that the illustrative lead and electrode assembly 700 may be delivered through a wide tunnel delivery tool with the shocking electrode 708 in a carrier.

While not explicitly shown, the lead 702 may include a proximal end with a proximal pin which along with additional contacts serves in this example as an electrical contact, which may be separated by insulating material. The lead 702 may be similar in form and function to the lead 302 described above. The proximal end may further include seal plugs. A proximal plug sheath may be provided for a region near the proximal end of the lead 702. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 702 extends from this proximal configuration through an intermediate region 704 to a distal end having a proximal electrode 706, a shocking electrode 708, and a distal tip electrode 710. The positioning and/or spacing of the electrodes 706, 708, 710 may be adjusted and/or reconfigured to optimize sensing and/or therapy delivery. For example, both sensing electrodes 706, 710 may be placed proximal or distal to the shocking electrode 708. This is just an example. It is contemplated that the electrodes 706, 708, 710 may be placed beneath the skin and over the ribcage of the patient. In other embodiments, the electrodes 706, 708, 710 may be placed in a substernal location using an implant procedure that may include a xiphoid or sub-xiphoid incision that allows for tunneling along the back side of the sternum. The electrodes 706, 708, 710 may also be placed elsewhere as desired including for example, for use with right sided, anterior-posterior, or other implant positions.

Lead 702 is shown for illustrative purposes, however, other designs and configurations including fewer, more or different electrodes 706, 708, 710, or contacts, may be used. Additional design elements such as bifurcation or other splitting, paddles or other designs may be used instead with an anchoring device attached at the time of implant. The lead 702 is not shown as including a passageway for a stylet to use during introduction, however, a lumen for that purpose may be provided if desired. In the illustrative example, the lead 702 has a body that contains passageways having connectors therein for coupling the proximal contacts to the shocking electrode 708, proximal electrode 706, and/or distal electrode 710.

The distal tip electrode 710 is shown with a suture hole 712. The suture hole 712 may be coupled to a base portion 714. Other designs may be used. In some embodiments, a suture hole 712, or other fixation means, may not be required and/or may not be provided.

The shocking electrode 708 have a generally woven structure. For example, the shocking electrode 708 may have a woven structure, fabricated from one or more filaments 716. The filaments 716 may be embedded in, or partially embedded in a silicone carrier 718, although this is not required. In some embodiments, the shocking electrode 708 may be braided with one filament 716. In other embodiments, the shocking electrode 708 may be braided with several filaments 716. In another embodiment, the shocking electrode 708 may be knitted or of a knotted type. The filaments 716 may be have a generally round or a generally flat (e.g. rectangular) cross-sectional shape, as desired. However, other cross-sectional shapes may be used. In some embodiments, each filament 716 may include a plurality of filaments wound or woven together. In still another embodiment, the shocking electrode 708 may be laser cut. It is contemplated that a custom laser cut plate may be used to achieve desired mechanical properties as well as to arrive at a shape which reduces the defibrillation threshold. While the shocking electrode 708 is illustrated as having a substantially rectangular peripheral shape, the shocking electrode 708 may take any shape desired such as, but not limited to ovular, circular, square, polygonal, etc. The shocking electrode 708 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

A thin permeable membrane may be positioned over the electrode 708 and/or other portions of the lead and electrode assembly 700 to inhibit tissue ingrowth. Coatings, such as, but not limited to expanded polytetrafluoroethylene (ePTFE) may also be applied to the lead and electrode assembly 700, or portions thereof, to facilitate extraction and/or to reduce tissue ingrowth. In some embodiments, one or more of the electrodes 706, 708, 710 may be include a high capacitive coating such as, but not limited to iridium oxide (IrOx), titanium nitride (TiN), or other "fractal" coatings which may be used, for example, to improve electrical performance. The lead and electrode assembly 700, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

Figure 8A:
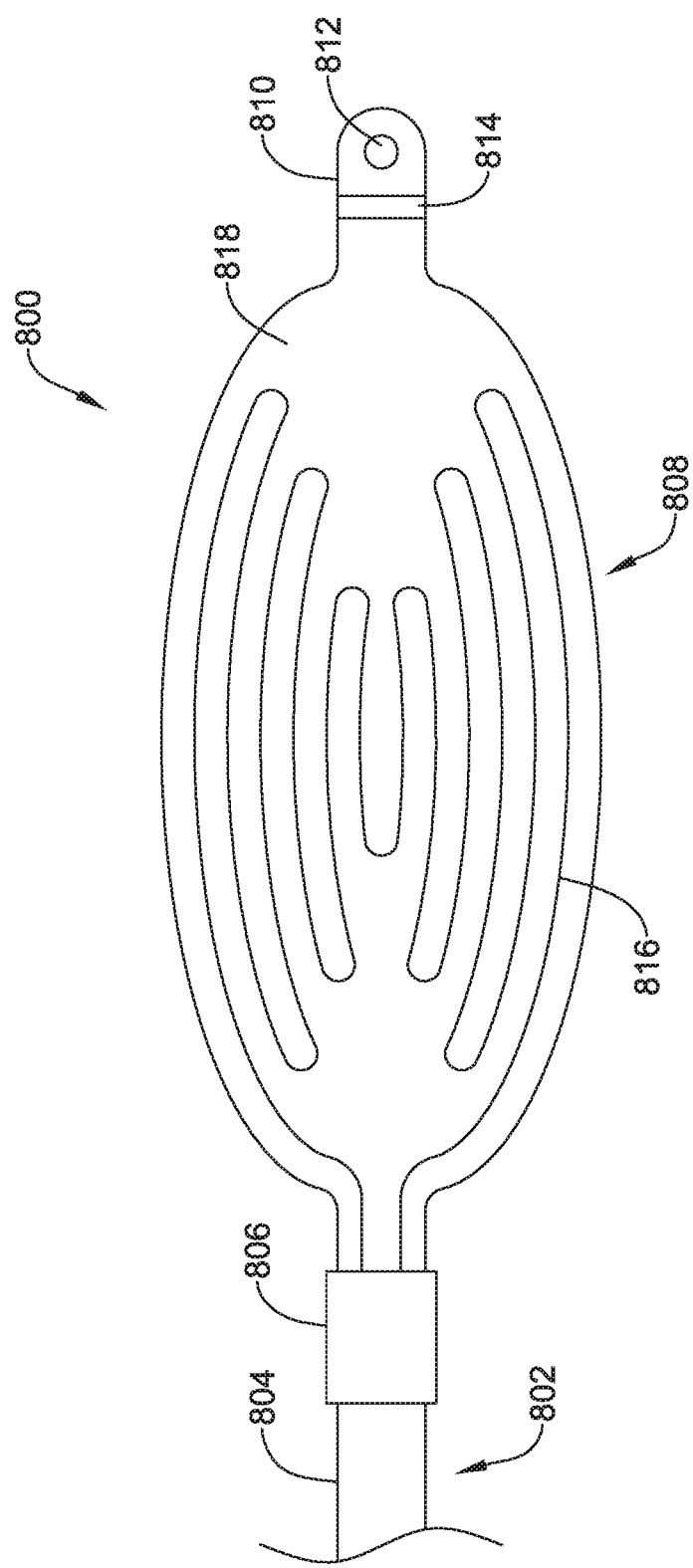

FIG. 8A shows a top view of another illustrative lead and electrode assembly 800 for use with an implantable cardiac rhythm management system, such as, but not limited to the S-ICD System™ from Cameron Health, Inc., and Boston Scientific Corporation described with respect to FIG. 1. While not explicitly shown, the illustrated assembly 800 may be configured to move between a delivery configuration and an implanted configuration. For example, the illustrated assembly 800 may be delivered in a generally collapsed configuration (e.g. rolled) and placed into the configuration shown in FIG. 8 after deployment. This may allow a smaller delivery tool to be used for insertion of the lead assembly 800. However, this is not required. It is contemplated that the illustrative lead and electrode assembly 800 may be delivered through a wide tunnel delivery tool with the shocking electrode 808 in a carrier.

While not explicitly shown, the lead 802 may include a proximal end with a proximal pin which along with additional contacts serves in this example as an electrical contact, which may be separated by insulating material. The lead 802 may be similar in form and function to the lead 302 described above. The proximal end may further include seal plugs. A proximal plug sheath may be provided for a region near the proximal end of the lead 802. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 802 extends from this proximal configuration through an intermediate region 804 to a distal end having a proximal electrode 806, a shocking electrode 808, and a distal tip electrode 810. The positioning and/or spacing of the electrodes 806, 808, 810 may be adjusted and/or reconfigured to optimize sensing and/or therapy delivery. For example, both sensing electrodes 806, 810 may be placed proximal to or distal to the shocking electrode 808. This is just an example. It is contemplated that the electrodes 806, 808, 810 may be placed beneath the skin and over the ribcage of the patient. In other embodiments, the electrodes 806, 808, 810 may be placed in a substernal location using an implant procedure that may include a xiphoid or sub-xiphoid incision that allows for tunneling along the back side of the sternum. The electrodes 806, 808, 810 may also be placed elsewhere as desired including for example, for use with right sided, anterior-posterior, or other implant positions.

Lead 802 is shown for illustrative purposes, however, other designs and configurations including fewer, more or different electrodes 806, 808, 810, or contacts, may be used. Additional design elements such as bifurcation or other splitting, paddles or other designs may be used instead with an anchoring device attached at the time of implant. The lead 802 is not shown as including a passageway for a stylet to use during introduction, however, a lumen for that purpose may be provided if desired. In the illustrative example, the lead 802 has a body that contains passageways having connectors therein for coupling the proximal contacts to the shocking electrode 808, proximal electrode 806, and/or distal electrode 810.

The distal tip electrode 810 is shown with a suture hole 812. The suture hole 812 may be coupled to a base portion 814. Other designs may be used. In some embodiments, a suture hole 812, or other fixation means, may not be required and/or may not be provided.

The shocking electrode 808 may be a printed circuit patch on a liquid crystal polymer 818. The shocking electrode 808 may include a platinum, gold, or other noble trace 816 positioned on the liquid crystal polymer. The trace 816 or circuit may take any pattern desired and may be selected to optimize the therapy. For example, the trace 816 may be a continuous trace which winds back and forth over the surface of the liquid crystal polymer 818. It is further contemplated that the peripheral shape of the shocking electrode 808 may also be selected to reduce the defibrillation threshold. While the shocking electrode 808 is illustrated as having a substantially oval peripheral shape, the shocking electrode 708 may take any shape desired such as, but not limited to rectangular, circular, square, polygonal, tear drop, etc. The shocking electrode 808 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

A thin permeable membrane may be positioned over the shocking electrode 808 and/or other portions of the lead and electrode assembly 800 to inhibit tissue ingrowth. Coatings, such as, but not limited to expanded polytetrafluoroethylene (ePTFE) may also be applied to the lead and electrode assembly 800, or portions thereof, to facilitate extraction and/or to reduce tissue ingrowth. In some embodiments, one or more of the electrodes 806, 808, 810 may be include a high capacitive coating such as, but not limited to iridium oxide (IrOx), titanium nitride (TiN), or other "fractal" coatings which may be used, for example, to improve electrical performance. The lead and electrode assembly 800, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

Figure 8B:
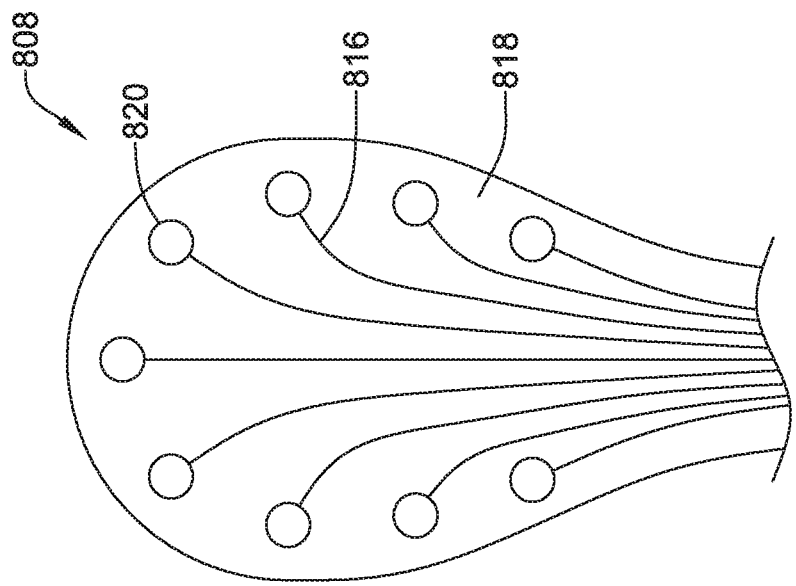

FIGS. 8B-8E show top view of alternative shocking electrodes 808 that may be used with the illustrative lead and electrode assembly 800 described above. The shocking electrodes 808 illustrated in FIGS. 8A-8E should not be considered to be inclusive of all possible arrangements of the printed circuit patch but rather examples of some possible configurations. The configurations of printed traces 816 and electrodes 820 are endless and may be highly customized to achieve a desired defibrillation threshold. FIG. 8B illustrates a shocking electrode 808 that includes a plurality of traces 816 fanning out from a central area of the liquid crystal polymer 818, in a similar manner to the veins of a leaf. A printed electrode 820 may be positioned at the end of all or some of the traces 816. The printed electrodes 820 may vary in shape and size as desired.

Figure 8C:
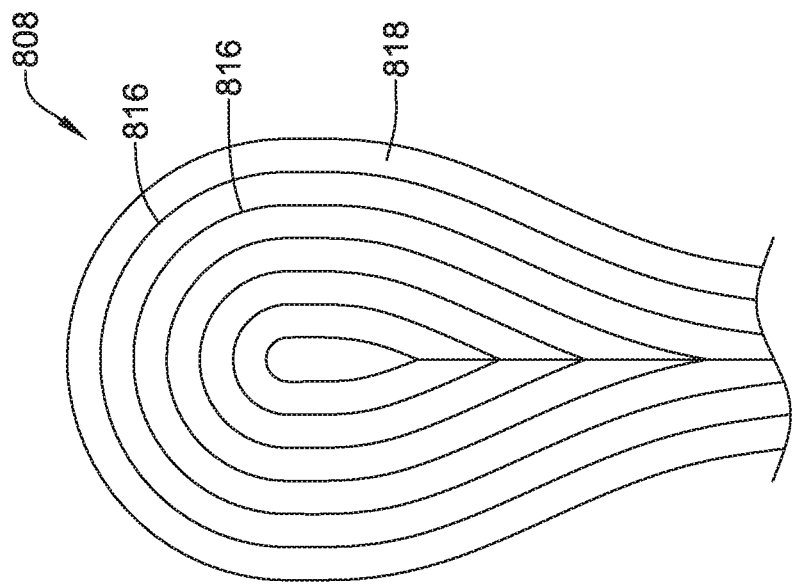

FIG. 8C illustrates a shocking electrode 808 that includes a plurality of traces 816. Each trace 816 may have a shape which mirrors the peripheral shape of the liquid crystal polymer 818. The traces 816 may be spaced a distance from one another at regular or irregular intervals. The traces 816 may get progressively smaller towards the center of the liquid crystal polymer 818. In some instances, the traces 816 may generally resemble a loop-type fingerprint. The number and/or size of the traces 816 may vary, as desired.

FIG. 8D illustrates a shocking electrode 808 that include a centrally located electrode 820 and a plurality of electrodes 820 positioned about a perimeter of the liquid crystal polymer 818. The electrodes 820 may be connected through a series of traces 816. The electrodes 820 may vary in shape, size, and/or positioning as desired.

Figure 8E:
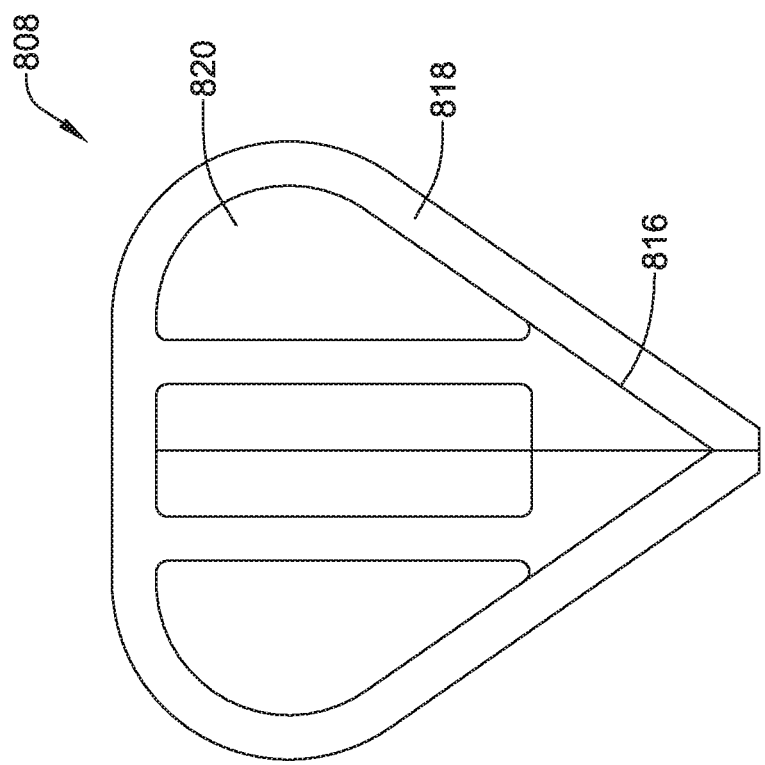

FIG. 8E a shocking electrode 808 having a bulbous shape. The shocking electrode 808 may include a plurality of electrodes 820. In some instances, the electrodes 820 may be sized and shaped to mirror a perimeter of the liquid crystal polymer 818. The electrodes 820 may be connected to one or more traces 816. The electrodes 820 may vary in shape, size, and/or positioning as desired.

Figure 9A:
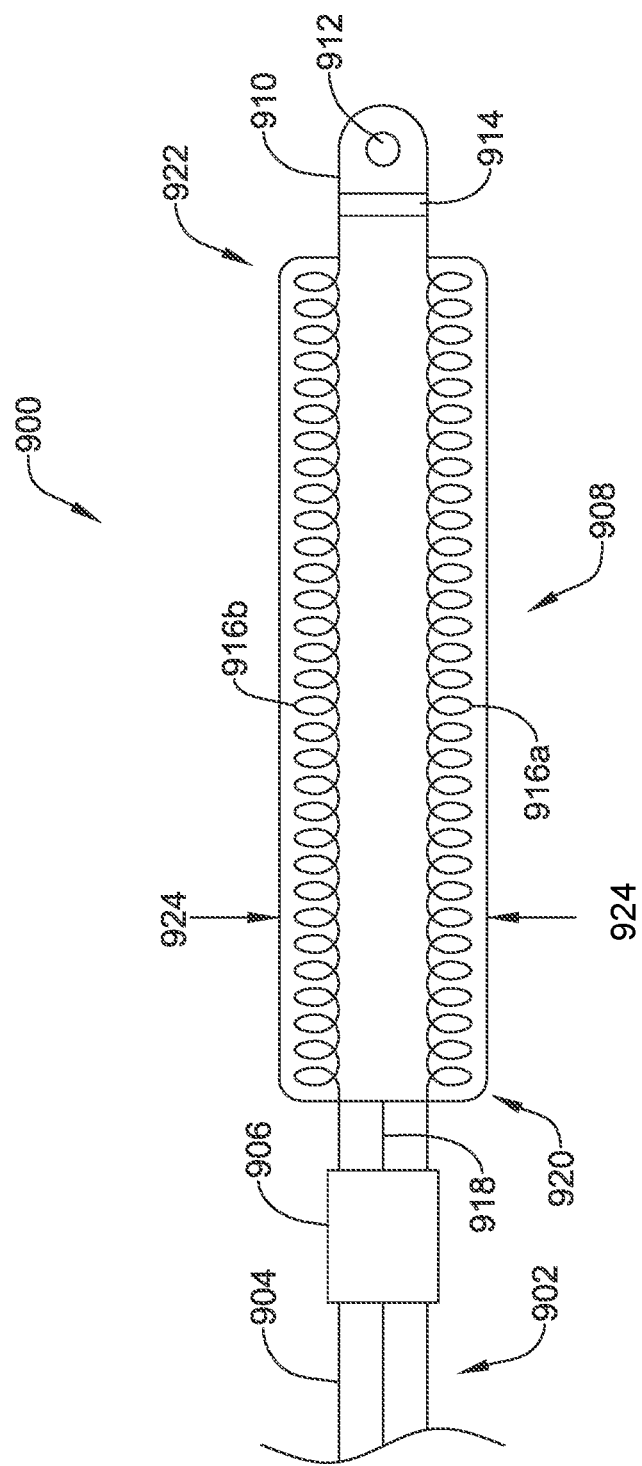
FIGS. 9A-9B show another illustrative electrode for use with an implantable to cardiac rhythm management system.
Figure 9B:
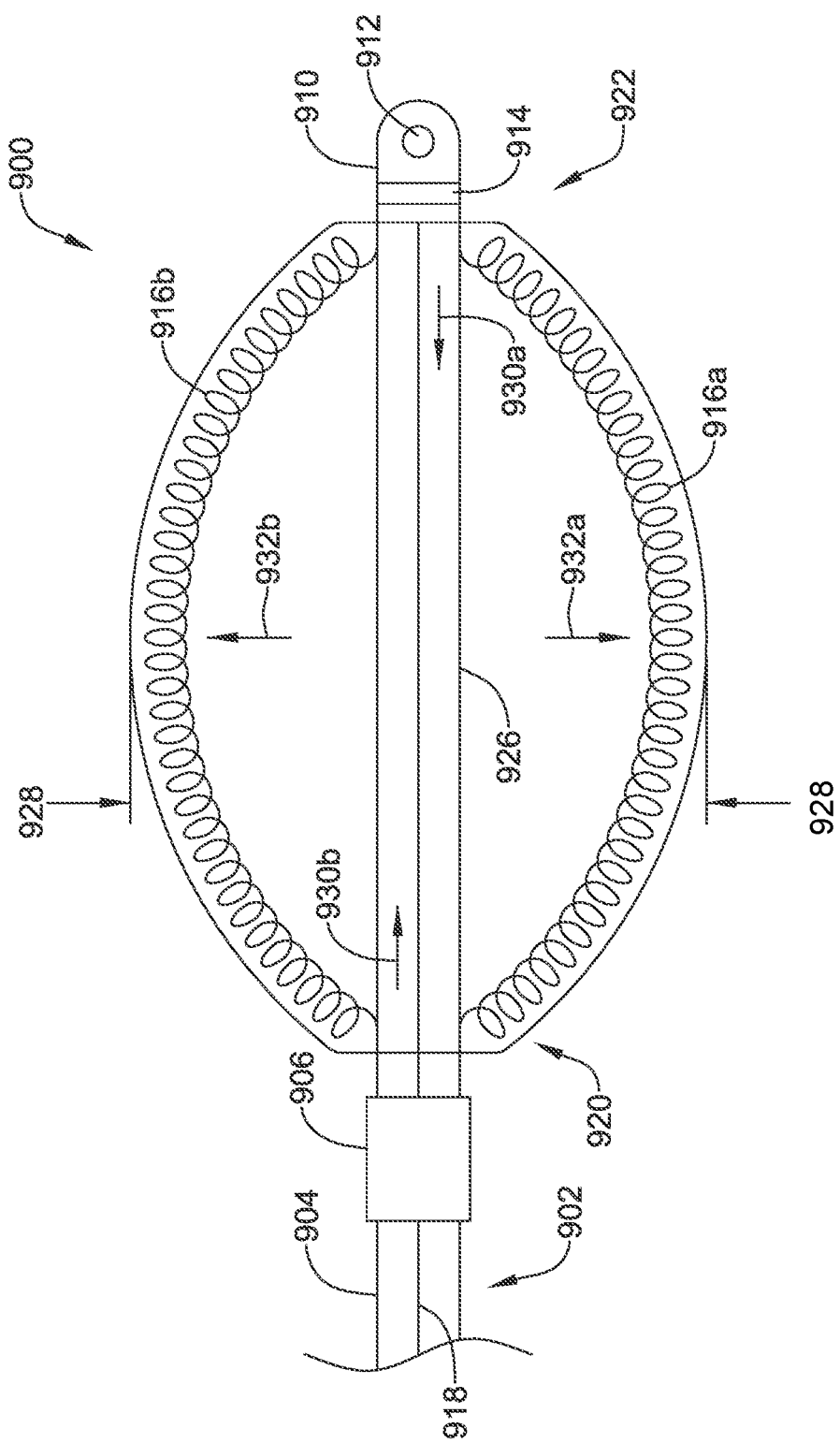

FIGS. 9A and 9B show a top view of another illustrative lead and electrode assembly 900 for use with an implantable cardiac rhythm management system, such as, but not limited to the S-ICD System™ from Cameron Health, Inc., and Boston Scientific Corporation described with respect to FIG. 1. In some embodiments, the illustrated assembly 900 may be configured to move between a collapsed or delivery configuration, shown in FIG. 9A and an expanded or implanted configuration, shown in FIG. 9B. However, it is contemplated that the illustrative lead and electrode assembly 900 of FIG. 9A may be both the delivery configuration and the implanted configuration. Similarly, the illustrative lead and electrode assembly 900 of FIG. 9B may be both the delivery configuration and the implanted configuration.

While not explicitly shown, the lead 902 may include a proximal end with a proximal pin which along with additional contacts serves in this example as an electrical contact, which may be separated by insulating material. The lead 902 may be similar in form and function to the lead 302 described above. The proximal end may further include seal plugs. A proximal plug sheath may be provided for a region near the proximal end of the lead 902. The pin, contacts, insulating material, and seal plugs may be configured for placement inside a bore on a header of an implantable pulse generator. In some embodiments, the proximal end may have standard plug designs (DF-1, DF-4, etc.) for use in other devices. The lead 902 extends from this proximal configuration through an intermediate region 904 to a distal end having a proximal electrode 906, a coil electrode 908, and a distal tip electrode 910. The positioning and/or spacing of the electrodes 906, 908, 910 may be adjusted and/or reconfigured to optimize sensing and/or therapy delivery. For example, both sensing electrodes 906, 910 may be placed proximal or distal to the coil electrode 908. This is just an example. It is contemplated that the electrodes 906, 908, 910 may be placed beneath the skin and over the ribcage of the patient. In other embodiments, the electrodes 906, 908, 910 may be placed in a sub sternal location using an implant procedure that may include a xiphoid or subxiphoid incision that allows for tunneling along the back side of the sternum. The electrodes 906, 908, 910 may also be placed elsewhere as desired including for example, for use with right sided, anterior-posterior, or other implant positions.

Lead 902 is shown for illustrative purposes, however, other designs and configurations including fewer, more or different electrodes 906, 908, 910, or contacts, may be used. Additional design elements such as bifurcation or other splitting, paddles or other designs may be used instead with an anchoring device attached at the time of implant. The lead 902 is not shown as including a passageway for a stylet to use during introduction, however, a lumen for that purpose may be provided if desired. In the illustrative example, the lead 902 has a body that contains passageways having connectors therein for coupling the proximal contacts to the coil 908, proximal electrode 906, and/or distal electrode 910.

The distal tip electrode 910 is shown with a suture hole 912. The suture hole 912 may be coupled to a base portion 914. Other designs may be used. In some embodiments, a suture hole 912, or other fixation means, may not be required and/or may not be provided.

The coil electrode 908 may be formed from two or more individual electrodes 916a, 916b. In some embodiments, the electrodes 916a, 916b may be coil electrodes. In other embodiments, the electrodes 916a, 916b may be other electrically active members, such as, but not limited to, struts. While the coil electrode 908 is illustrated as including two electrodes 916a, 916b, the coil electrode 908 may including any number of individual electrodes desired, such as, but not limited to, one, two, three, four, five, or more. Further, in either configuration, coil electrodes 916a, 916b may be positioned close to one another (e.g. touching) or spaced a distance, as desired. The coil electrode 908 may be affixed to the lead body 902 at its proximal end 920 and its distal end 922. As shown in FIG. 9B, in some embodiments, the lead body 902 may include a portion 926 that extends between the proximal end 920 and the distal end 922 of the coil electrode 908. It is contemplated that the lead body 902 may include a telescoping feature or nested tubular members that allows the proximal end 920 and/or distal end 922 of the coil electrode 908 to be moved along a longitudinal axis of the system 900, such as in the direction of arrows 930a, 930b, shown in FIG. 9B. In other embodiments, the lead body 902 may be disposed within one or both of the electrodes 916a, 916b. While not explicitly shown, the coil electrode 908 may include a lumen or passageway for receiving a stylet or other delivery aid.

Each of the electrodes 916a, 916b may be formed from a round or flat (ribbon) wire, as desired. The wires may be relatively straight or coiled, as desired. In some instances, adjacent windings of the electrodes 916a, 916b may be in contact with one another while in other instances adjacent windings may be spread out or spaced a distance from one another, as desired. It is contemplated that the individual coil 916a, 916b may have the same or similar structure, or may be different, as desired. For example one electrode 916a may be more tightly wound than the other 916b. This is just an example.

A thin permeable membrane may be positioned over the shocking electrode 908 and/or other portions of the lead and electrode assembly to inhibit tissue ingrowth. A single permeable membrane may surround both electrodes 916a, 916b. Alternatively, or additionally, separate membranes may surround each of the electrodes 916a, 916b individually. Coatings, such as, but not limited to expanded polytetrafluoroethylene (ePTFE) may also be applied to the lead and electrode assembly 900, or portions thereof, to facilitate extraction and/or to reduce tissue ingrowth. In some embodiments, one or more of the electrodes 906, 908, 910 may be include a high capacitive coating such as, but not limited to iridium oxide (IrOx), titanium nitride (TiN), or other "fractal" coatings which may be used, for example, to improve electrical performance. The lead and electrode assembly 900, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

The electrodes 916a, 916b may be actuatable or expandable from a delivery configuration having a first width 924, shown in FIG. 9A, to an implanted configuration having a second larger width 928, as shown in FIG. 9B. While the embodiments shown in FIGS. 9A and 9B are described as movable between two different configurations, it is contemplated the lead and electrode assembly 900 may be fixed in either arrangement. In other words, in some embodiments the electrodes 916a, 916b may be movable relative to one another while in other embodiments, the electrodes 916a, 916b may be in a fixed arrangement relative to one another. It is contemplated that the coil electrode 908, in either the delivery configuration or the implanted configuration, may be similar in size to the coil electrode 308 described above. The coil electrode 908 may have a larger surface area and/or shadow than a typical shocking coil electrode. It is contemplated that increasing the surface area and/or shadow may allow the defibrillation threshold to be lowered which may allow the canister, such as canister 12, to have a smaller profile.

The lead and electrode assembly 900 may be actuated between the delivery configuration and the implanted configuration using any number of deployment mechanisms. In one example, the distal electrode 910 may be secured to the tissue. Once the distal end has been secured, the lead body 902 may be distally advanced to apply a pushing force to the proximal end 920 of the coil electrode 908 using, for example a push-pull member 918. This may cause the coil electrodes 916a, 916b to bias outward, for example in directions 932a, 932b, shown in FIG. 9B while also shortening in length, as shown at arrows 930a, 930b. It is contemplated that the same result may be achieved by applying a proximal, or pulling force to the distal end 922 of the coil 908 using the push-pull member 918. In yet another example, the coil electrodes 916a, 916b may be formed in the expanded configuration illustrated in FIG. 9B. The coil electrodes 916a, 916b may be compressed into a lower profile delivery configuration through the application of a biasing force. For example, when the coil electrodes 916a, 916b are disposed within a delivery tool, the delivery tool may maintain the coil electrodes 916a, 916b in a reduced profile configuration.

Figure 10:
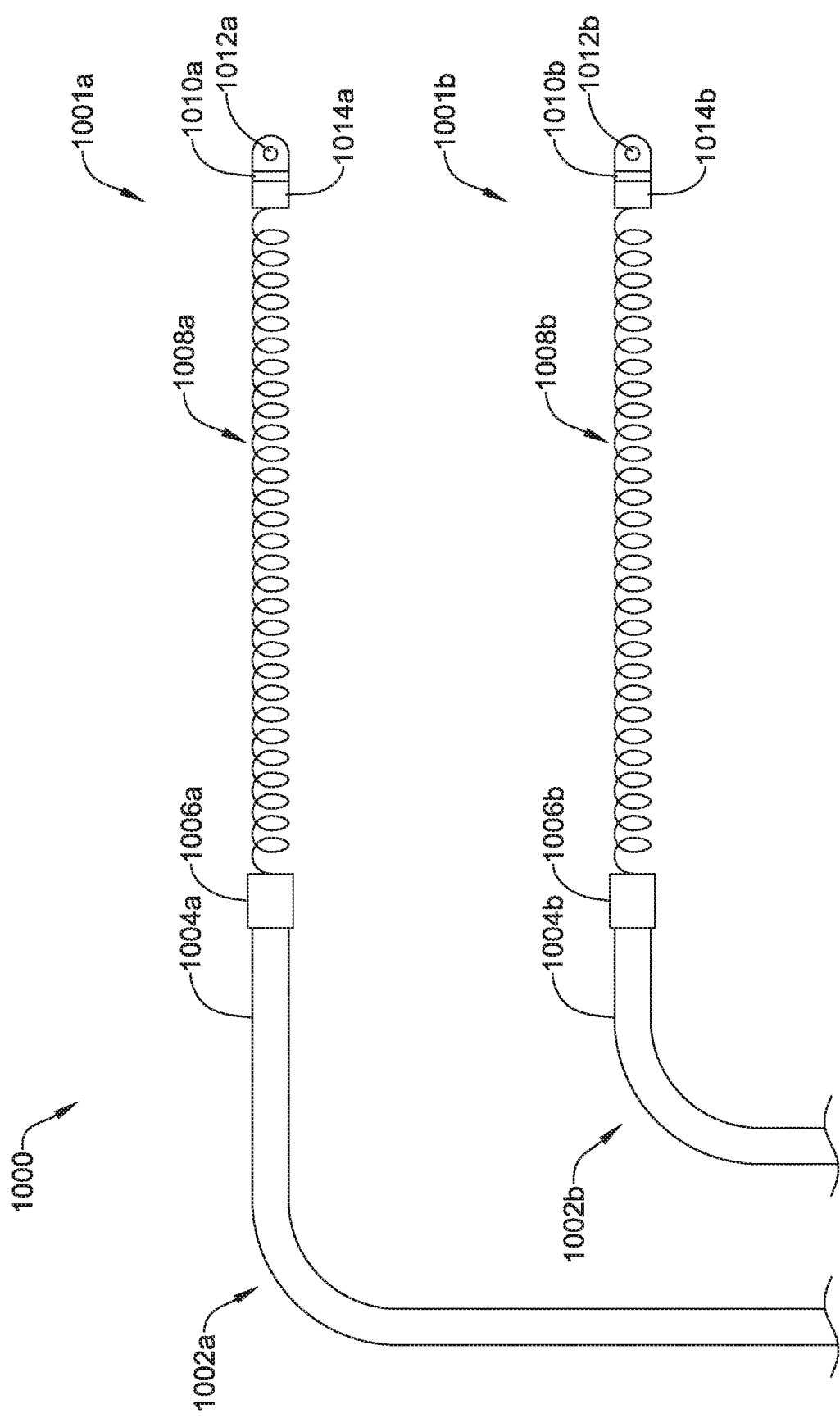
FIG. 10 shows another illustrative electrode for use with an implantable cardiac rhythm management system.

FIG. 10 shows a top view of another illustrative lead and electrode assembly 1000 for use with an implantable cardiac rhythm management system, such as, but not limited to the S-ICD System™ from Cameron Health, Inc., and Boston Scientific Corporation described with respect to FIG. 1. The lead and electrode assembly 1000 may include a first lead and electrode assembly 1001a and a second lead and electrode assembly 1001b. While the assembly 1000 is described as including two lead and electrode assemblies 1001a, 1001b, it is contemplated that the assembly 1000 may include any number of assemblies desired, such as, but not limited to one, two, three, four, or more. In some embodiments, the lead and electrode assembly 1000 may be configured to place a first lead and electrode assembly 1001a along a first side of the sternum and the other lead and electrode assembly 1001b on the opposite side of the sternum, although this is not required.

While not explicitly shown, each assembly 1001a, 1001b may include a lead 1002a, 1002b including a proximal end with a proximal pin which along with additional contacts serves in this example as an electrical contact, which may be separated by insulating material. The leads 1002a, 1002b may be similar in form and function to the lead 302 described above. The proximal end may further include seal plugs. A proximal plug sheath may be provided for a region near the proximal end of the leads 1002a, 1002b. The pin, contacts, insulating material, and seal plugs may be configured for placement inside a bore on a header of an implantable pulse generator. In some embodiments, the proximal end may have standard plug designs (DF-1, DF-4, etc.) for use in other devices. The leads 1002a, 1002b extend from this proximal configuration through an intermediate regions 1004a, 1004b to a distal end having a proximal electrode 1006a, 1006b, a coil electrode 1008a, 1008b, and a distal tip electrode 1010a, 1010b. The positioning and/or spacing of the electrodes 1006a, 1006b, 1008a, 1008b, 1010a, 1010b may be adjusted and/or reconfigured to optimize sensing and/or therapy delivery. For example, both sensing electrodes 1006a, 1006b, 1010a, 1010b may be placed proximal to or distal to the coil electrode 1008a, 1008b. In other embodiments, only one of the assemblies may include sensing electrodes. These is just an example. It is contemplated that the electrodes 1006a, 1006b, 1008a, 1008b, 1010a, 1010b may be placed beneath the skin and over the ribcage of the patient. In other embodiments, the electrodes 1006a, 1006b, 1008a, 1008b, 1010a, 1010b may be placed in a substernal location using an implant procedure that may include a xiphoid or sub-xiphoid incision that allows for tunneling along the back side of the sternum. The electrodes 1006a, 1006b, 1008a, 1008b, 1010a, 1010b may also be placed elsewhere as desired including for example, for use with right sided, anterior-posterior, or other implant positions.

Lead 1002a, 1002b is shown for illustrative purposes, however, other designs and configurations including fewer, more or different electrodes 1006a, 1006b, 1008a, 1008b, 1010a, 1010b, or contacts, may be used. Additional design elements such as bifurcation or other splitting, paddles or other designs may be used instead with an anchoring device attached at the time of implant. The lead 1002a, 1002b is not shown as including a passageway for a stylet to use during introduction, however, a lumen for that purpose may be provided if desired. In the illustrative example, the lead 1002a, 1002b has a body that contains passageways having connectors therein for coupling the proximal contacts to the coil 1008a, 1008b, proximal electrode 1006a, 1006b, and/or distal electrode 1010a, 1010b.

The distal tip electrode 1010*a*, 1010*b* is shown with a suture hole 1012*a*, 1012*b*. The suture hole 1012*a*, 1012*b* may be coupled to a base portion 1014*a*, 1014*b*. Other designs may be used. In some embodiments, a suture hole 1012*a*, 1012*b*, or other fixation means, may not be required and/or may not be provided.

These assemblies 1001*a*, 1001*b* may be designed into one single electrode with a yolk feature and single terminal for connection to the canister. For example, the two coil electrodes 1008*a*, 1008*b* may be formed as a single electrode having a "V" or "Y" configuration. Alternatively, the assemblies 1001*a*, 1001*b* may include two completely separate electrodes or assemblies that plug into a dual chamber header each with their own terminal. In yet another embodiment, the assemblies 1001*a*, 1001*b* may also use an adaptor in which each assembly 1001*a*, 1001*b* may be plugged into. The adaptor may then be plugged into the canister with a single terminal. In another embodiment, one electrode may be built with an optional "second electrode" port integrated into the lead body (similar to a built in "Y" adaptor). This may allow the user may choose to add a second electrode to the patient by plugging it into this port. These configurations may allow the coil electrodes 1008*a*, 1008*b* to have a larger surface area and/or shadow than a typical shocking coil electrode. It is contemplated that increasing the surface area and/or shadow may allow the defibrillation threshold to be lowered which may allow the canister, such as canister 12, to have a smaller profile.

While not explicitly shown, the coil electrodes 1008*a*, 1008*b* may include a lumen or passageway for receiving a stylet or other delivery aid. A thin permeable membrane may be positioned over the coil 1008*a*, 1008*b* and/or other portions of the lead and electrode assemblies 1001*a*, 1001*b* to inhibit tissue ingrowth. A single permeable membrane may surround both electrodes 1008*a*, 1008*b*. Alternatively, or additionally, separate membranes may surround each of the electrodes 1008*a*, 1008*b* individually. Coatings, such as, but not limited to expanded polytetrafluoroethylene (ePTFE) may also be applied to the lead and electrode assembly 1001*a*, 1001*b*, or portions thereof, to facilitate extraction and/or to reduce tissue ingrowth. In some embodiments, one or more of the electrodes 1006*a*, 1006*b*, 1008*a*, 1008*b*, 1010*a*, 1010*b* may be include a high capacitive coating such as, but not limited to iridium oxide (IrOx), titanium nitride (TiN), or other "fractal" coatings which may be used, for example, to improve electrical performance. The lead and electrode assembly 1001*a*, 1001*b*, or portions thereof, may include treatments in local areas to increase attachment, such as, for example, along the length of the lead, near an electrode, or at or near the distal tip, the inclusion of a roughened surface, a surface of different polymer or other material, or a local a coating to encourage tissue growth such as a steroid.

Figure 11:
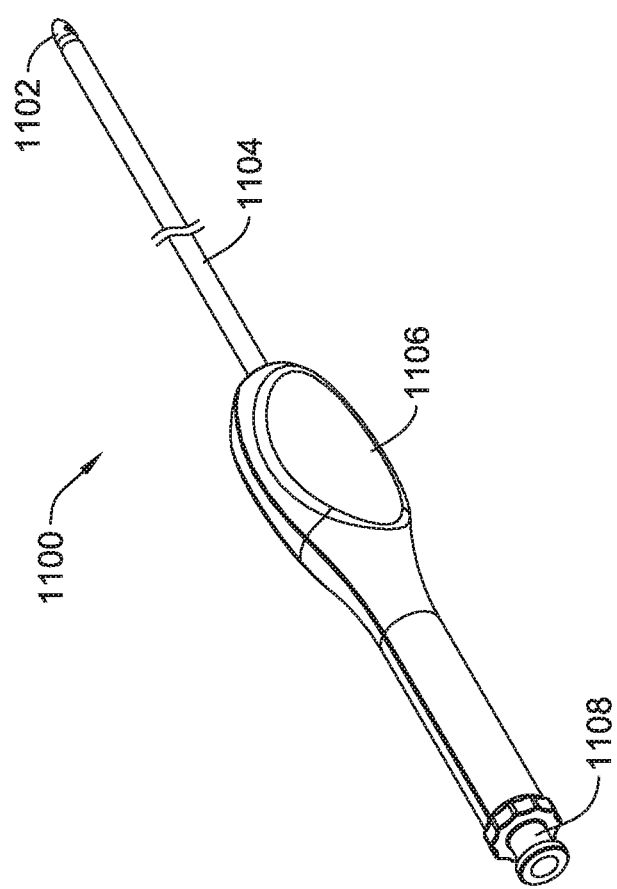
FIG. 11 shows an illustrative prior art electrode introducer tool.

FIG. 11 shows an illustrative prior art electrode introducer tool. The illustrative prior art tool 1100 includes a bullet-shaped tunneling tip 1102 at the end of a stiff shaft 1104 made, for example, of a medical grade metal such as stainless steel. At the proximal end, there is a gripping portion 1104 and a port 1108. The gripping portion 1106 is provided for ergonomics but does not provide any indication of the rotational placement of the shaft 1104 and/or tip 1102 (unlike several illustrative examples shown below).

The tip 1102 may include a hook or a suture hole, for example, to allow it to be secured to a lead for implantation. For example, in some prior methods, the tunneling tool would be used to tunnel from a xiphoid incision to an incision at the left axilla and, once the tunneling tool tip 1102 is accessible at the left axillary incision, a distal tip of a lead would be sutured thereto, in order that the lead could be pulled into the tunnel formed during advancement from the xiphoid incision to the left axillary incision as the tool 1100 is withdrawn. A suture hole or other attachment feature may be used in some of the illustrative examples that follow.

In some disclosures of a device as in FIG. 11, the proximal port 1108 may be used to infuse or inject analgesic, antibiotic, or other substance, to prevent patient pain or infection. For example, some desciptions suggested that lidocaine could be provided via the port 1108 for infusion through a lumen extending to the suture hole at the tip 1102 (see, for example, U.S. Pat. No. 8,157,813). However, the lumen so described was not suggested as providing an avenue for implantation of the electrical lead itself, in contrast to several examples that follow.

FIGS. 12A-12C show an illustrative tunneling tool. The tool 1200 is shown with a distal tunneling tip 1202, proximal to which there is an elongated, rigid shaft 1204; the shaft 1204 may be malleable to fit a particular patient anatomy if desired, and may be made, for example, of stainless steel or other suitable biocompatible material. While the tool 1200 is shown as a straight tunneling tool, it may come in a curved configuration instead. A coating of slippery material, for example, may be provided over the tunneling tip 1202 and/or shaft 1204.

A proximal handle is shown at 1206 and may include a proximal port at 1201 for infusion of a liquid, fluid or gas, if desired. The cross section at FIG. 12B shows a generally circular profile, though other shapes may be used if desired. An alternative cross section is shown at FIG. 12C, indicating this time a shaft 1220 having a lumen therein at 1222. The lumen 1222 may be sized to receive a guidewire or stylet to allow tracking or additional stiffness during tunneling. If desired, the lumen 1222 may be sized to receive a lead for implantation. In some examples, the lumen 1222 is sized to receive a lead having a collapsible section which may include an electrode, such as shown in several examples above.

Alternatively, during insertion of a tool as shown in FIGS. 12A-12B to create a tunnel in a patient for lead implantation, a sheath, such as a tearable sheath, may be placed over the tunneling tool 1200. Once the desired tunnel is made, the sheath would be held in place as the tunneling tool 1200 is removed, and the lead would be inserted into the sheath to a desired position. The sheath would then be removed by, for example, tearing it along a line of preferential tearing such as a perforation.

This illustration is somewhat similar to that of FIG. 11 in certain respects, however there are significant differences. First, the shaft 1204 in FIG. 12 is intended to be larger than that of the more conventional tool shown in FIG. 11. For example, the tool in FIG. 11 may have an outer diameter at the tip and shaft in the range of about 3.2 millimeters, while the device in FIG. 12 may have an outer diameter of 4 millimeters up to about 10 millimeters. In another respect, the lumen 1222 shown for FIG. 12 may be used for passing through a second device, such as a guidewire, stylet or the lead that is being implanted.

The device of FIGS. 12A-12C may be used in a method such as detailed above in FIG. 2. For example, the tunneling tip 1202 may be advanced through an incision to a desired location, such that a tunnel is created to that desired location which may be subcutaneous, substernal, or another location to which lead placement is desired. The tool may then be removed and a lead placed. In an alternative, the lead may be contained in a lumen such as lumen 1222 in the tunneling tool during tunneling, or may be advanced through the lumen 1222 after tunneling is complete. The proximal handle 1206 may include a port at location 1210 or as shown at 1212, through which the lead can exit. As the tool 1200 is removed, the lead may be held in place for removal in an "over-the-wire" manner. If the lead has a collapsible electrode such as one shown in various examples above, the collapsible electrode may then be expanded after the tool 1200 is removed.

FIGS. 13A-13D show another illustrative tunneling tool. Here, the tool 1300 has a wide projection near its distal tunneling tip 1302. The projection is shown at 1304 along the distal end of the shaft 1306. If desired, sharpened cutting edges may be provided on one or more edges 1308 of the projection 1304 including, for example, the leading (distal-facing) edges, as shown, or one the trailing (proximal facing) edges (not shown), as well as the outward facing edges tangent to the axis of the tool 1300. The cutting edges 1308 may be provided to make it easier for the user to dissect tissue and/or separate tissue layers during tunneling.

The projection 1304 has a width that is greater than its thickness, as highlighted in the cross section at FIG. 13B, while the main shaft may be generally circular as shown at 1306 in FIG. 13C, or may have any other suitable shape such as polygonal or oval, if desired. The handle of the tool 1300 at its proximal end may include a flattened portion as shown at 1310. By flattened portion, no specific method of manufacturing is intended to be conveyed; rather, the intend of the descriptive term is to indicate that there is a portion having a width that is greater than its thickness, with the width of the flattened portion 1310 aligned with the width of the projection 1304, as shown in FIG. 13A. The flattened portion 1310 can thus be used by an implanter to determine the orientation of the projection relative to the tissue layers of the patient quickly and without having to palpate the patient's skin.

As highlighted in FIG. 13D, the tool 1300 may include a lumen 1322 that extends through the shaft 1306 and/or projection. The lumen 1322 may be open at the distal tip 1302, if desired. The lumen 1322 may be sized to receive a guidewire or stylet to allow tracking or additional stiffness during tunneling. If desired, the lumen 1322 may be sized to receive a lead for implantation. In some examples, the lumen 1322 is sized to receive a lead having a collapsible section which may include an electrode, such as shown in several examples above.

The device of FIGS. 13A-13D may be used in a method such as detailed above in FIG. 2. For example, the tunneling tip 1302 may be advanced through an incision to a desired location, such that a tunnel is created to that desired location which may be subcutaneous, substernal, or another location to which lead placement is desired. The tunnel so created may be wider than it is thick, as defined in part by the projection 1304; generally the aim may be to separate tissue layers as opposed to actually cutting tissue itself. The physician/user may use the flattened portion 1310 of the handle to determine the orientation of projection 1304 during tunneling. The tool may then be removed and a lead placed. In an alternative, the lead may be contained in a lumen such as lumen 1322 in the tunneling tool 1300 during tunneling, or may be advanced through the lumen 1322 after tunneling is complete. The proximal handle may include a port (not shown) through which the proximal end of the lead can exit. As the tool 1300 is removed, the lead may be held in place for removal in an "over-the-wire" manner, keeping at least a portion of the lead within the patient and/or at a desired location in the patient. If the lead has a collapsible electrode such as one shown in various examples above, the collapsible electrode may then be expanded after the tool 1300 is removed.

FIGS. 14A-14C show another illustrative tunneling tool. The tool 1400 includes a distal tunneling tip 1402, and a shaft 1404 extending thereto from a handle (not shown). The shaft 1404 may have a profile as shown in FIG. 14B, and may include a lumen 1412 therethrough as shown by FIG. 14C. The handle (not shown) may include a flattened section/element having a similar utility to element 1310 in FIG. 13A.

The device of FIGS. 14A-14C may be used in a method such as detailed above in FIG. 2. For example, the tunneling tip 1402 may be advanced through an incision to a desired location, such that a tunnel is created to that desired location which may be subcutaneous, substernal, or another location to which lead placement is desired. The tunnel so created may be wider than it is thick, as defined in part by the profile shown at 1404 in FIG. 14B. Again, the aim may be to separate tissue layers as opposed to actually cutting tissue itself. The physician/user may use the flattened portion of the handle to determine the orientation of shaft 1404 during tunneling. The tool may then be removed and a lead placed. In an alternative, the lead may be contained in a lumen such as lumen 1412 in the tunneling tool 1400 during tunneling, or may be advanced through the lumen 1412 after tunneling is complete. The proximal handle may include a port (not shown) through which the lead proximal end can exit. As the tool 1400 is removed, the lead may be held in place for removal in an "over-the-wire" manner, keeping at least a portion of the lead within the patient and/or at a desired location in the patient. If the lead has a collapsible electrode such as one shown in various examples above, the collapsible electrode may then be expanded after the tool 1400 is removed.

Figure 15D:
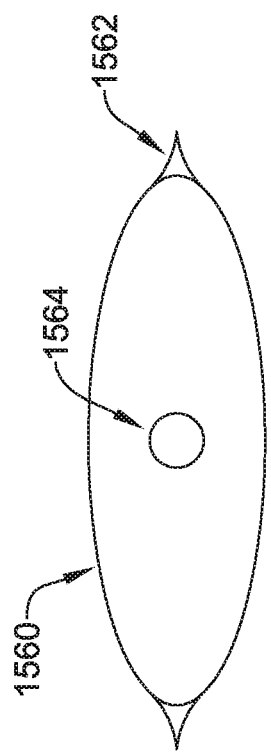

FIGS. 15A-15E show an illustrative tunneling tool having an inflatable element. In this example, the tunneling tool 1500 includes a distal tunneling tip 1502 with an inflatable balloon 1504 mounted proximally thereof on a shaft 1506. The balloon 1504 may at least initially be wrapped on the shaft 1506 to keep a reduced profile during initial tunneling (the width of the balloon 1504 shown in FIG. 15A is exaggerated for ease of visualization). One or several lumens may be provided within the shaft 1506 including, for example, an inflation lumen and a device lumen shown at 1508; the device lumen 1508 may instead be omitted if desired.

A handle is also shown at 1510 with details highlighted at FIG. 15B. A flattened portion is shown in FIG. 15B with a central piece having one or more lumens therein and wings 1514. The wings 1514, as detailed further below, may align with the width and/or cutting edges (if provided) on the balloon 1504 when the balloon is fully inflated.

Inflation is controlled at a first port 1514 which may include a pressure gage as shown at 1516 to determine and control inflation pressure. Inflation may be provided using any suitable gas or liquid; typically a sterile saline may be used for inflation. If desired, a stylet or guidewire may be provided as well, with handle 1520 for manipulating a distal tip 1522. The stylet or guidewire may be used to guide the tool 1500 to a desired location and/or may provide added stiffness during insertion.

Figure 15E:
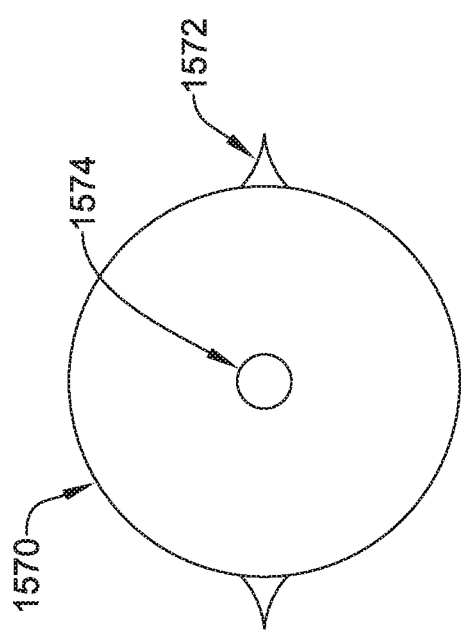
Figure 15C:
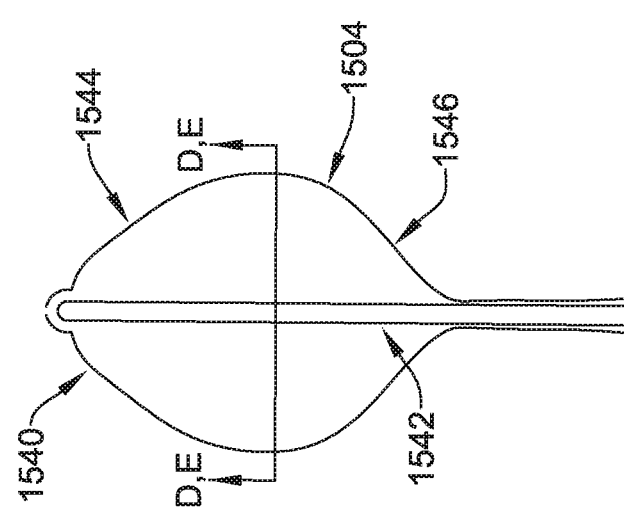

FIG. 15C shows the balloon 1504 in an inflated state. The balloon 1504 is preferably a non-complaint balloon which, when inflated to selected pressure, will assume a pre-defined shape. Various materials are known for non-compliant balloon construction, including balloons for angioplasty procedures; example materials may include nylon and polyethylene terephthalate. Some examples are discussed in U.S. Pat. Nos. 5,348,538 and 5,714,110; shape for the balloon may be created as discussed in the '538 patent.

The balloon in a fully inflated state is shown at 1540 in FIG. 15C, with leading edge 1544 and trailing edge 1546, with a central member shown at 1542 extending therethrough. FIG. 15D shows a section view of the balloon 1540, with this variant 1560 having a greater width than thickness. The central member 1564 may include a lumen (as shown), or it may be solid. One or more of the central member 1564 or the main shaft 1506 may be formed of a reinforced polymeric tube (such as a catheter having a mesh, braid, coil or other support embedded or coextruded therein), or of a hypotube, or of any other suitable structure and material.

FIG. 15E shows another variant in which the balloon 1570 may be more circular in outer profile, with the central member 1574 again being either solid (as shown) or having a lumen therein.

The balloon 1504 may include cutting edges as highlighted at 1562 in FIG. 15D and 1572 in FIG. 15E. Methods and materials for making cutting balloon catheters may be drawn from intravascular devices. Some illustrative examples are shown in U.S. Pat. Nos. 7,070,576, 7,632,288, 7,758,604, 7,976,557, and 8,491,615, the disclosures of which are incorporated herein by reference. Other designs may be used in the present invention, as the intent is not to limit to any specific material or structure for the cutting balloon design.

The device of FIGS. 15A-15E may be used in a method such as detailed above in FIG. 2. For example, the tunneling tip 1502 may be advanced through an incision to a desired location, with or without use of a guidewire or stylet 1520/1522. A preliminary tunnel is thus created to a desired location which may be subcutaneous, substernal, or another location to which lead placement is desired. Next, the inflatable element, such as balloon 1504, can be inflated via the inflation port 1514, to expand the tunnel in a preferred manner using, for example, a wide, flat balloon (FIG. 15D) or a round balloon (FIG. 15E). This may be a single step for dissection, or the inflatable element, such as balloon 1504, may be inflated, deflated, repositioned, and inflated again, to continue to create a desired space for the lead. Alternatively, the inflatable element, such as balloon 1504, may be expanded and kept in an expanded configuration while it is moved to create a desired space for the lead. Either way, the aim may be to separate tissue layers as opposed to actually cutting tissue itself.

The physician/user may use the flattened portion of the handle to determine the orientation of shaft 1506 during tunneling. The tool may 1500 then be removed after the balloon 1504 is deflated, and a lead placed. In an alternative, the lead may be contained in a lumen such as lumen 1508 in the tunneling tool 1500 during tunneling, or may be advanced through the lumen 1508 after tunneling is complete. The proximal handle may include a port through which the lead proximal end can exit. As the tool 1500 is removed, the lead may be held in place for removal in an "over-the-wire" manner, keeping at least a portion of the lead within the patient and/or at a desired location in the patient. If the lead has a collapsible electrode such as one shown in various examples above, the collapsible electrode may then be expanded after the tool 1500 is removed.

FIGS. 16A-16B show another illustrative tunneling tool having an inflatable element. The tunneling tool 1600 is shown with a tunneling tip 1602 that, in this instance, has an open ended lumen therethrough. An expandable member is shown as inflated balloon 1604 through which a central member extends. Though not included in the embodiment shown in FIGS. 16A-16B, the balloon 1604 may include cutting edges if desired. The main shaft 1606 of the device extends to a handle 1608. The handle is shown having a flatter, wide portion at 1608, which can be used as a guide to maintain the desired tissue plane when inflating or otherwise using the balloon 1604 for tissue dissection/separation. In addition, the handle includes a first device port at 1610, an inflation port at 1612, a grip at 1614, and a second device port at 1616.

The first and second device ports 1610, 1616 may access the same or different lumens. In the illustration of FIG. 16A, two alternative ways of inserting an electrode are highlighted—the electrode proximal end is shown as a plug 1622A, exiting first device port 1610; as an alternative, the electrode proximal end may be at plug 1622B, exiting the second device port 1616. In another example, port 1616 may be used to insert a guidewire or stylet during insertion of the tool 1600 to a desired location in the patient, after which the guidewire or stylet may be removed and replaced with an electrode 1620 inserted through either of the device ports 1610, 1616.

The cross section at FIG. 16B illustrates the main shaft 1606 comprises an inner tubular member 1618, with a device lumen shown at 1630, and inflation lumen at 1632. A coaxial cross section is shown, however, a side-by-side configuration may be used instead if desired. As is known in the catheter arts, the outer shaft 1606 or inner tubular member 1618 may be formed for stiffness and steerability, with the inner tubular member 1618 possibly having a slippery innermost layer and an outer layer adapted for secure attachment to the balloon, with a tie layer therebetween. The outer shaft 1606 may include a braided or other support member within a polymeric extrusion, or may include or be formed of a hypotube. Additional support structures to provided added stiffness and pushability, such as a core wire or core wires, may be included as well. Some balloon angioplasty details may be found in U.S. Pat. No. 6,102,890 and the additional patents and references cited therein.

The device of FIGS. 16A-16B may be used in a method such as detailed above in FIG. 2. For example, the tunneling tip 1602 may be advanced through an incision to a desired location, with or without use of a guidewire or stylet. A preliminary tunnel is thus created to a desired location which may be subcutaneous, substernal, or another location to which lead placement is desired. Next, the inflatable element, such as balloon 1604, can be inflated via the inflation port 1612, to expand the tunnel in a preferred manner using, for example, a wide, flat balloon (see again FIG. 15D) or a round balloon (see again FIG. 15E). This may be a single step for dissection, or the inflatable element, such as balloon 1604, may be inflated, deflated, repositioned, and inflated again, to continue to create a desired space for the lead. Alternatively, the inflatable element, such as balloon 1604, may be expanded and kept in an expanded configuration while it is moved to create a desired space for the lead. Either way, the aim may be to separate tissue layers as opposed to actually cutting tissue itself.

The physician/user may use the flattened portion of the handle 1614 to determine the orientation of shaft 1606 and balloon 1604 during tunneling. The tool 1600 may then be removed after the balloon 1604 is deflated, and a lead placed. In an alternative, the lead may be contained in a lumen such as device lumen 1630 in the tunneling tool 1600 during tunneling, or may be advanced through the lumen 1630 after tunneling is complete, with the proximal end 1622A/1622B of the lead 1620 exiting either of ports 1610 or 1616. As the tool 1600 is removed, the lead may be held in place for removal in an "over-the-wire" manner, keeping at least a portion of the lead within the patient and/or at a desired location in the patient. If the lead has a collapsible electrode such as one shown in various examples above, the collapsible electrode may then be expanded after the tool 1600 is removed.

It should be noted that, if desired, a "rapid-exchange" approach may be used in which a side-by-side lumen construction on the main shaft 1606 includes a device lumen having a tearable or frangible wall, or a slit or channel, through which the lead 1620 may exit the main shaft 1606 as the tool 1600 is removed. In the "over the wire" approach shown in FIG. 16A, to remove the tool and keep the lead 1620 in place, the user needs a relatively long proximal tail on the lead 1620, such that the distal end of the lead 1620 remains in place while the entire tool 1600 is removed from the patient. In the "rapid-exchange" approach, the lead 1620 would exit laterally from the shaft 1606 during removal through the tearable or frangible wall, or slit or channel, reducing the required length of the lead 1620. Concepts and designs of rapid exchange angioplasty catheters, or from single-operator-exhange biliary catheters may be used.

Figure 17A:
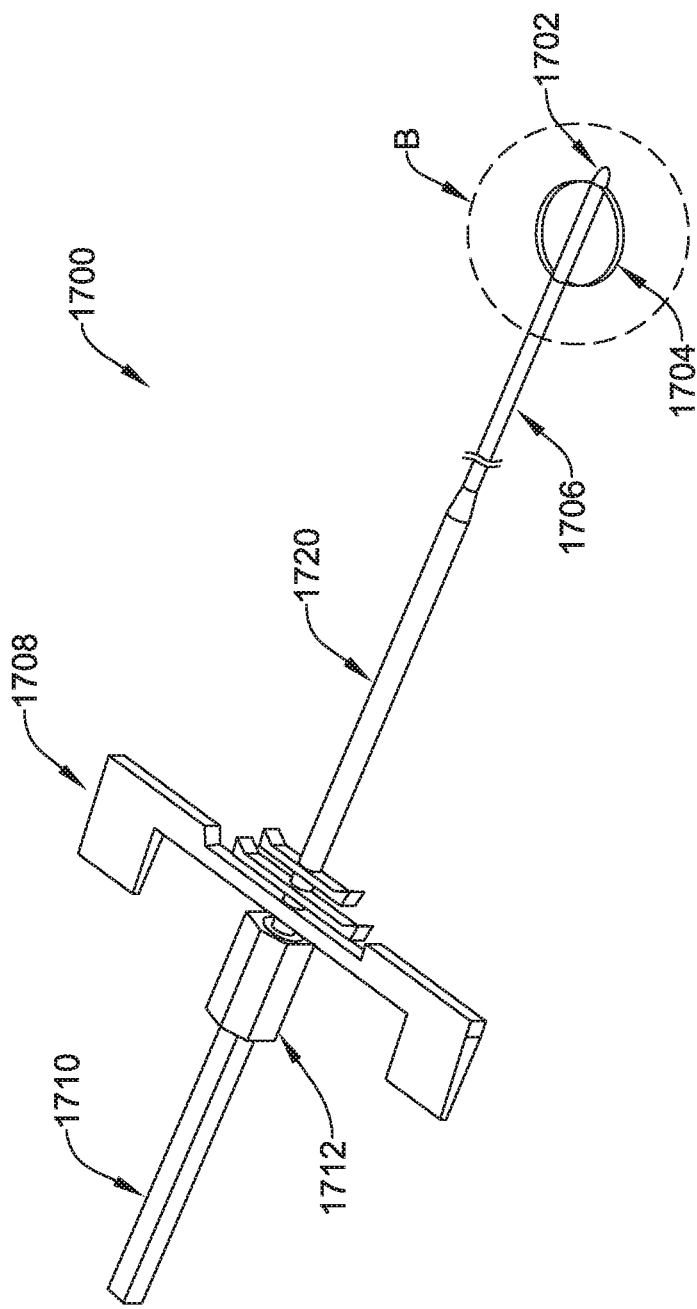

FIGS. 17A-17G show several details and variants for another illustrative tunneling tool. FIG. 17A provides a perspective view of an illustrative tunneling tool. The tool 1700 includes a distal tunneling tip 1702, proximal to which an expandable dissecting element is shown at 1704. A shaft 1706 extends to the dissecting element 1704. A handle is shown at 1708 with wings extended therefrom, with the wings aligned relative to the dissecting element 1704 so that control of the wings 1708 controls the plane defined by the width of the dissecting element 1704. A proximal handle 1710 includes a control knob 1712. Twisting the control knob 1712 determines the extent to which the dissecting element 1704 expands beyond the width of the tunneling tip 1702 and/or shaft 1706.

The tunneling tool 1700 may, in this example, be inserted through an insertion tube 1720, if desired. The insertion tube 1720 may be a splittable sheath. The additional insertion tube 1720 may be omitted. An insertion tube such as that shown at 1720 in FIG. 17A may optionally be used with any of the embodiments shown herein, if desired.

The total length from tip 1702 to handle 1708 may be in the range of, for example, 5 to 18 inches, or more or less, with the total tool length being from about 10 to 26 inches, or more or less. More desirably, the length from tip 1702 to handle may be in the range of about 6 to 12 inches. Similar lengths may be used in other embodiments shown herein.

FIG. 17B is a detail view of region B in FIG. 17A. It can be seen that shaft 1706 has a forked distal end to which the tunneling tip 1702 is attached. If desired, a central member may be included to define a lumen through the center of shaft 1706 and tip 1702, thought FIG. 17B omits such a design. The dissecting element is formed of a pair of wires 1704A, 1704B. In some examples, the two sides of the dissecting element 1704A, 1704B are designed to symmetrically expand outward as shown. The outward bend in this example may be positively induced by advancing a control rod 1704 within the shaft 1706 to force the outward bend shown. Alternatively, the outward bend may be caused by a pre-formed shape of the wires 1704A, 1704B, with the control rod being retractable from the position shown in FIG. 17B to pull the wires 1704A, 1704B back under tension to within the shaft 1706.

If desired the wires 1704A, 1704B may be coupled to an electrical source or ultrasonic transducer to induce heating or vibration and enhance the ability to cut or separate tissue layers. The wires may be springs or spring coils, if desired.

Figure 17D:
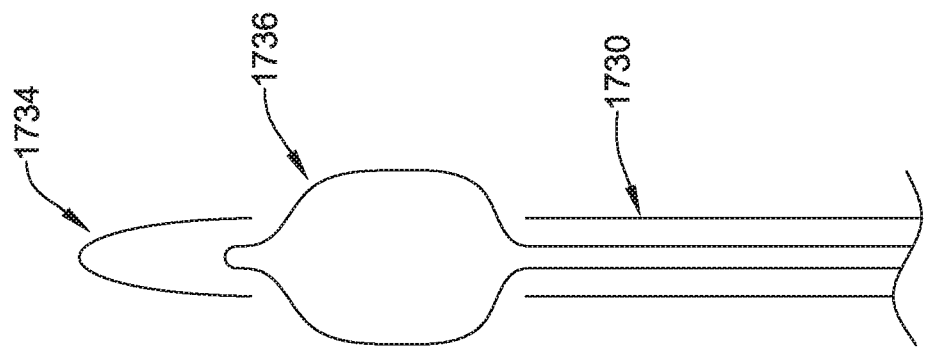
Figure 17C:
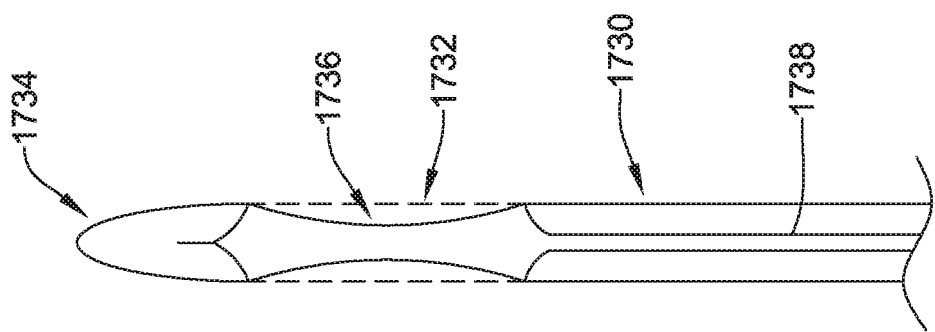

FIGS. 17C and 17D show a further illustration. The tunneling tool 1730 is shown here with an outer profile shown in dashed lines at 1732 leading to the tip 1734. When the dissecting element 1736 is in the retracted position shown in FIG. 17C, the outer dimension of the dissecting element 1736 is equal to or less than the outer profile 1732, as shown by FIG. 17C. When the dissecting element is expanded, for example by advancing the control member 1738, the dissecting element 1736 outer dimension goes beyond the outer profile 1732 of the tool 1730 and tip 1734, as shown in FIG. 17D.

Figures 17E, 17F:
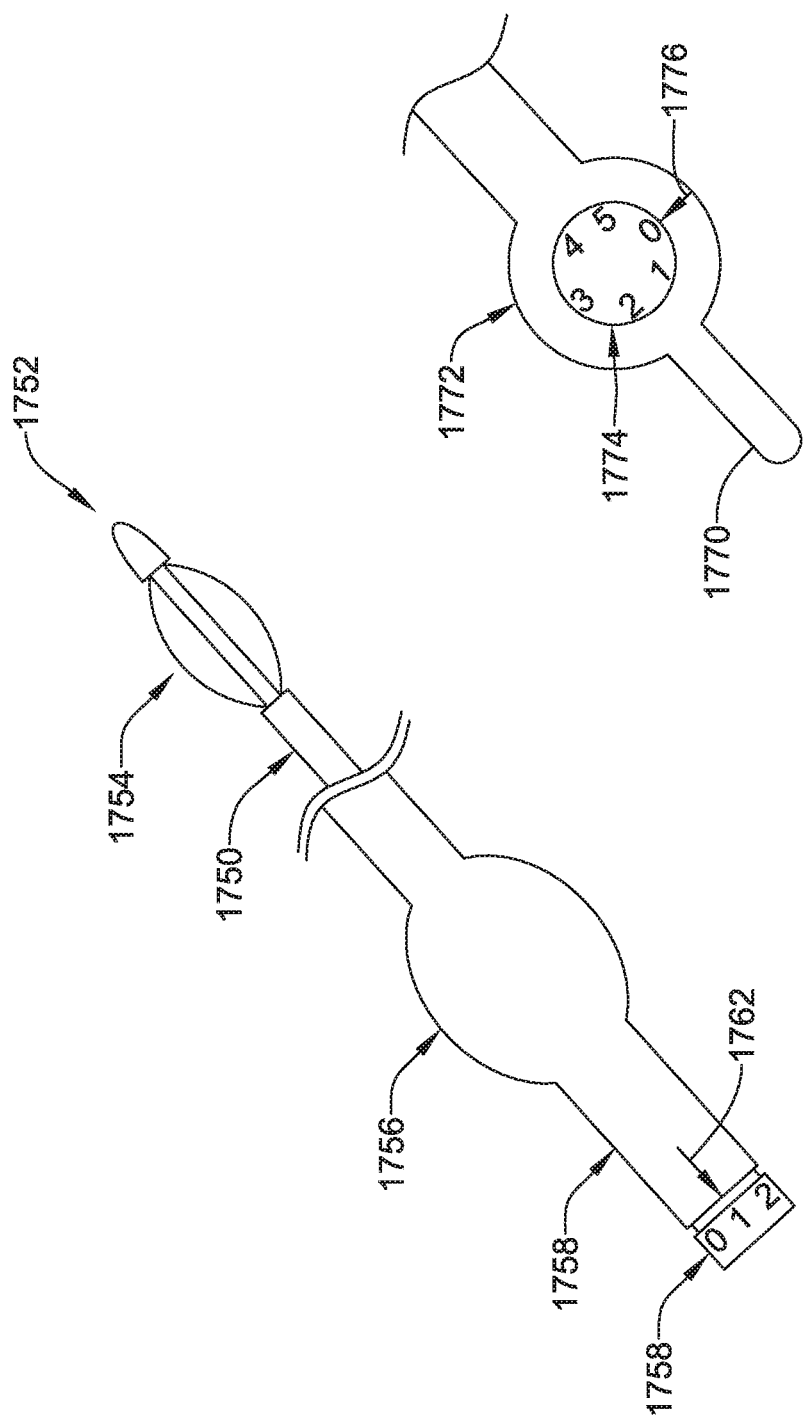

FIG. 17E shown an alternative to FIG. 17A. Here, the tool 1750 includes a tunneling tip 1752 proximal to which is a dissecting element 1754. A proximal handle is shown with a flattened portion 1756 that has a width that aligns with the width of the dissecting element 1754. A proximal grip is shown at 1758 and, in this example a dial 1760 is used with a marker 1762 to determine the extent to which the dissecting element 1754 is expanded by the control member (not shown). Turning the dial 1760 causes the shape of the dissecting element 1754 to change by one of rotating or advancing/retracting the control member (not shown). FIG. 17F shows another example with a dial 1774 that can be turned located on the flattened part 1772 of handle 1770, with marker/indicator at 1776. The numbers are shown for illustration; in some examples, the numbers may indicate a width of the dissecting member 1754, if desired.

FIG. 17G shows some illustrative wire designs that may be used in the construction of a dissecting element such as element 1736. A triangular wire 1780, a circular wire 1882, a ribbon wire 1790, and a diamond or square wire 1792 may be used. Other shapes may be used as well. If desired, as shown at 1782, the wire may comprise a central core 1784 and with an outer coating 1786 thereon. Also, as shown at 1792, cutting elements 1794 in the form of sharpened edges may be provided if desired; alternatively, items 1794 may simply be reinforcement of the edges. The wire may be formed of any suitable biocompatible material including, for example, stainless steel, platinum, titanium, or a superelastic alloy such as nickel-titanium alloy (for example, Nitinol), or others. The wires 1780, 1782, 1790, 1792 may be solid or hollow, as desired. Such materials and designs may be used as well in the embodiments of FIGS. 18A-18B, 19A-19B, 20A-20B, and 21A-21B.

The device of FIGS. 17A-17G may be used in a method such as detailed above in FIG. 2. For example, the tunneling tip 1702 may be advanced through an incision to a desired location, with or without use of a guidewire or stylet. A preliminary tunnel is thus created to a desired location which may be subcutaneous, substernal, or another location to which lead placement is desired. Next, the dissecting element 1704 is expanded to expand the tunnel. This may be a single step for dissection, or the dissecting element 1704 may be extended, retracted, repositioned, and extended again, to continue to create a desired space for the lead. Alternatively, the dissecting element 1704 may be expanded and kept in an expanded configuration while it is moved along with the rest of the tool 1700 to create a desired space for the lead. Generally speaking, the aim may be to separate tissue layers as opposed to actually cutting tissue itself. As before, if desired, a lead having an expandable electrode may be placed through a lumen (not shown) in tool 1700 and during tool removal the lead may be kept in place and the electrode then expanded into the created space.

Figure 18B:
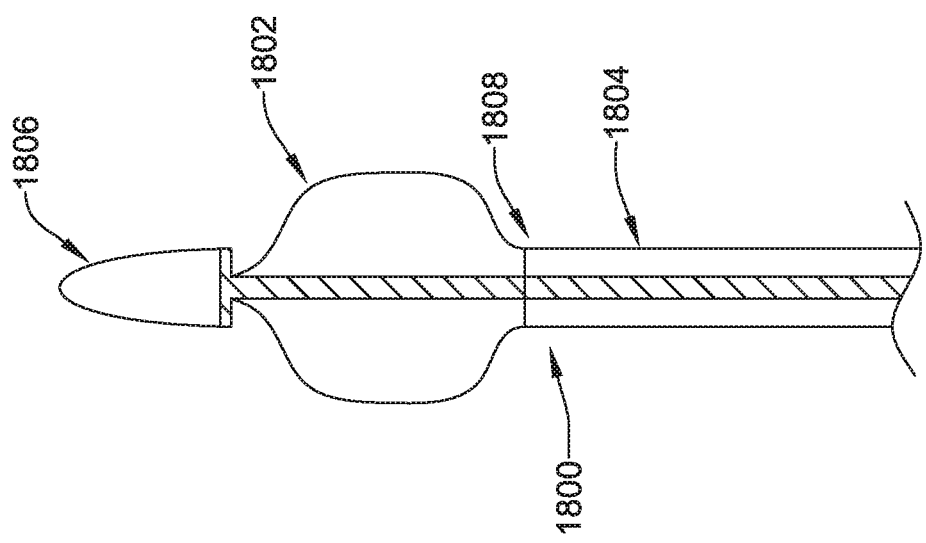
FIGS. 18A-18B show another illustrative tunneling tool.
Figure 18A:
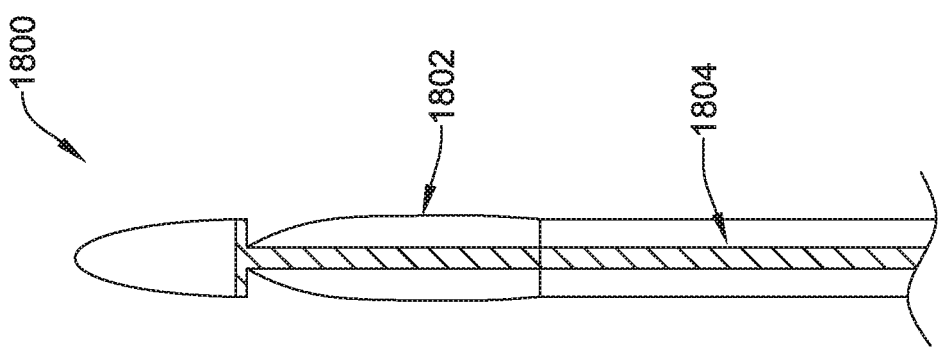

FIGS. 18A-18B show another illustrative tunneling tool, in this instance replacing the spring coils of FIGS. 17A-17G with linkage arrangements. The tool 1800 is shown having a linkage arrangement at 1802, in FIG. 18A in a retracted configuration as the control rod 1804 is in a non-extended position. When the control rod 1804 is extended, or twisted, depending on the mechanism used, the linkage 1802 extends outward from its retracted position to a dissecting configuration as shown in FIG. 18B. For example, advancing the control rod 1804 may press forward the linkage 1802 forcing it out of the slits at the end of the tool 1800. In another example, the control rod forces the linkage 1802 into the extended position by pulling the distal tip portion 1806 of tool 1800 toward the main shaft 1808. In another example, twisting the control rod, which may be eccentrically shaped near its distal end, to force the linkage out into an extended configuration. As with other examples, a lumen may be provided through the tool 1800 to allow for a guidewire, stylet, or lead to be placed therethrough, and the handle (not shown) may include a guide feature (such as a flattened portion) for alignment control relative to the linkage 1802.

The device of FIGS. 18A-18B may be used in a method such as detailed above in FIG. 2. For example, the tunneling tip of the distal tip portion 1806 may be advanced through an incision to a desired location, with or without use of a guidewire or stylet. A preliminary tunnel is thus created to a desired location which may be subcutaneous, substernal, or another location to which lead placement is desired. Next, the linkage 1802 is actuated using the control rod 1804 to assume the dissection configuration shown in FIG. 18B, expanding the preliminary tunnel. This may be a single step for dissection, or the linkage 1802 may be retracted and repositioned and extended again to continue to create a further desired space for the lead. Alternatively, linkage 1802 may be expanded and kept in an expanded configuration while it is moved to create a desired space for the lead. Either way, the aim may be to separate tissue layers as opposed to actually cutting tissue itself. As before, if desired, a lead having an expandable electrode may be placed through a lumen (not shown) in tool 1800 and during tool removal the lead may be kept in place and the electrode then expanded into the created space.

Figure 19A:
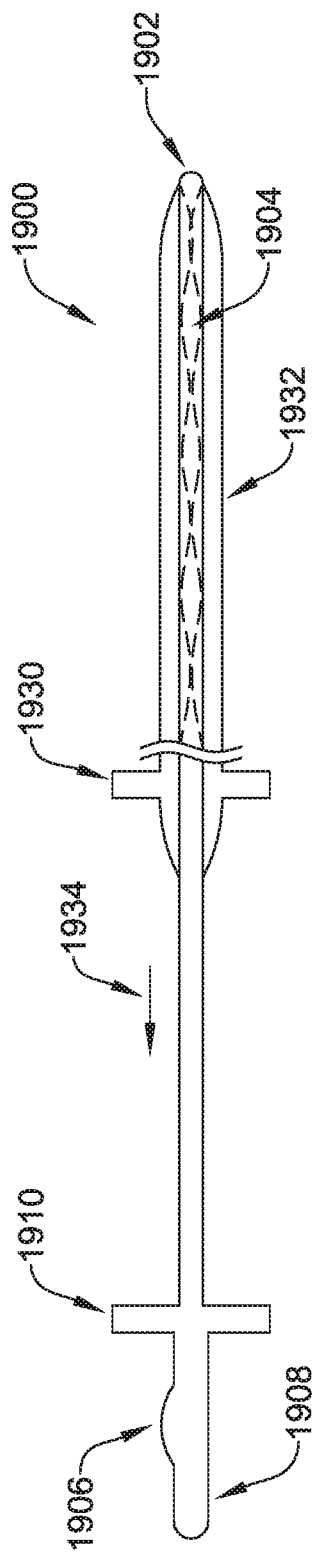
FIGS. 19A-19B show another illustrative tunneling tool.
Figure 19B:
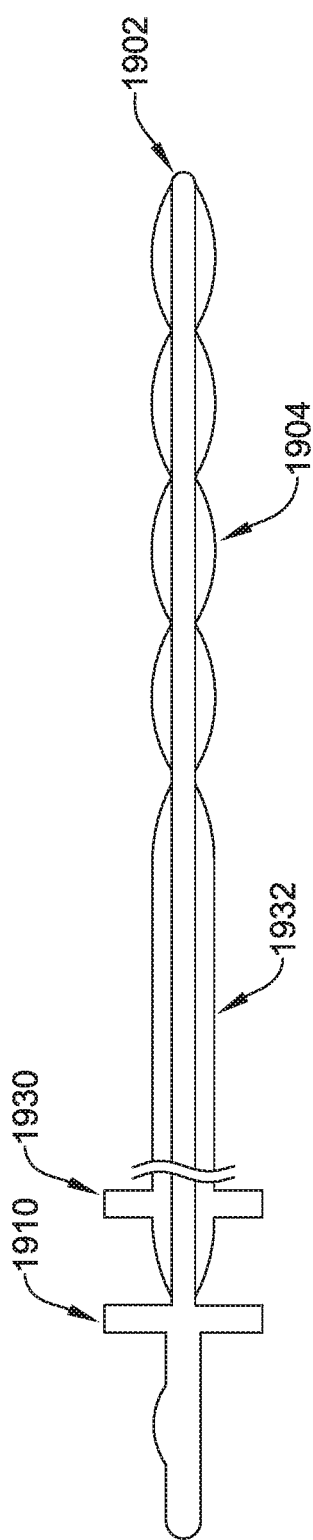

FIGS. 19A-19B show another illustrative tunneling tool. In this example, the tunneling tool 1900 has a tunneling tip at 1902 proximal to which is a spring wire shown at 1904 in phantom in FIG. 19A, and shown in FIG. 19B in an extended configuration. The tunneling tool includes a handle having a hilt 1910 adjacent to an optional flattened portion 1906 that may again serve as a guide for aligning the coil 1904 in a desired tissue plane. The proximal handle 1908 may, as before, include a port for access to a thru-lumen for use with a guidewire or stylet or to allow introduction of a lead.

The control mechanism in FIGS. 19A-19B is a sheath 1930 having a proximal handle as shown and a distally extending retraining portion shown at 1932. When the sheath 1930 is placed as shown in FIG. 19A, it covers and constrains the coil 1904. When moved in the proximal direction as indicated at 1934, the sheath 1930 releases the spring coil 1904 to create a configuration as in FIG. 19B. If desired, a control rod may be included as well to further control the shape of the spring coil 1904. Once the desired tunnel is formed, the sheath 1930 can be advanced over the coil 1904 to constrain it and prepare the tool for removal.

The device of FIGS. 19A-19B may be used in a method such as detailed above in FIG. 2. For example, the tunneling tip 1902 may be advanced through an incision to a desired location, with or without use of a guidewire or stylet. A preliminary tunnel is thus created to a desired location which may be subcutaneous, substernal, or another location to which lead placement is desired. Next, the sheath 1930 is retracted to release the spring coil 1904 to assume the dissection configuration shown in FIG. 19B, expanding the preliminary tunnel. This may be a single step for dissection, or the sheath 1930 may be advanced to constrain the coil 1904 for repositioning; once repositioned, the sheath 1930 may again be retracted to release the spring coil 1904 to create a further desired space for the lead. Alternatively, the sheath 1930 may be withdrawn to release the spring coil 1904, and the tool 1900 may be moved about to create a desired space for the lead. Either way, the aim may be to separate tissue layers as opposed to actually cutting tissue itself. As before, if desired, a lead having an expandable electrode may be placed through a lumen (not shown) in tool 1900 and during tool removal the lead may be kept in place and the electrode then expanded into the created space.

Figure 20A:
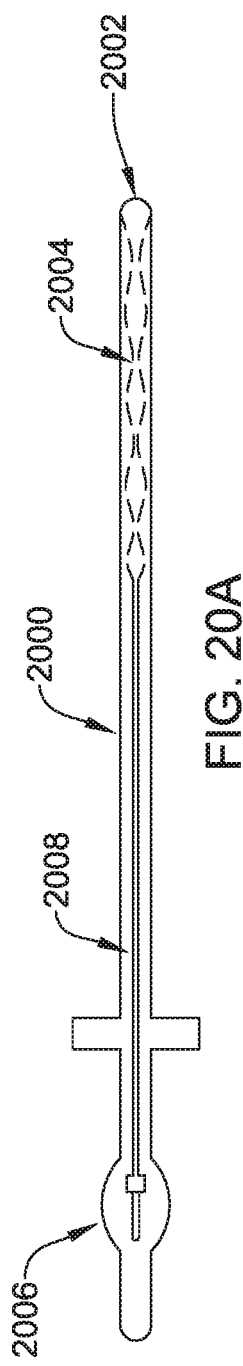
FIGS. 20A-20B show another illustrative tunneling tool.
Figure 20B:
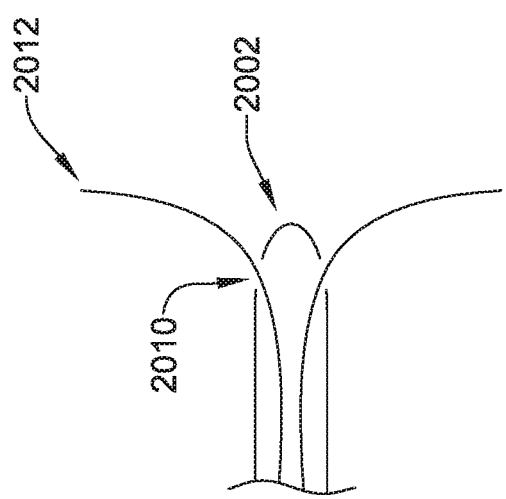

FIGS. 20A-20B show another illustrative tunneling tool. In this example, the tunneling tool 2000 includes a distal tunneling tip 2002, proximal to which there is a spring coil 2004, shown in phantom in FIG. 20A. The spring coil 2004 is coupled to a control rod 2008 that is controlled from the proximal handle by accessing a switch, slider, tab or lever at 2006. Alternatively, a knob or dial may be provided as shown for other examples above. The distal end is shown with the spring coil extended in FIG. 20B. It can be seen that the tunneling tip 2002 is near slots 2010 that allow the spring coil 2012 to exit the interior of the tool when the control rod 2008 is twisted or advanced. In this embodiment, the wire of the spring coil 2012 is preferably somewhat stiff, so that once the spring coil 2012 is extended as shown in FIG. 20B, movement of the tunneling tool 2000 causes tissue to be dissected and/or tissue layers to be separated, creating a space for lead implantation. A lumen may be provided within the tool 2000 for a guidewire, stylet, or lead.

FIGS. 21A-21B show another illustrative tunneling tool. The tool 2100 includes a tunneling tip 2102 and a shaft containing a cutting wire 2104. The handle 2106 may contain a switch, slider, tab, lever, knob or dial, or other control mechanism, 2108 proximal to which slots 2110 are provided. As can be see, in this example the cutting wire 2104 includes criss-crossed segments near the distal end of the tool 2100. When the cutting wire 2104 is actuated, it would move as shown in FIG. 21B, with free ends 2112 exiting via slots 2110 from within the tool 2100, near and proximal to the distal dissecting tip 2102. In this embodiment, the cutting wire 2104 is preferably somewhat stiff, so that once extended as shown in FIG. 21B, movement of the tunneling tool 2100 causes tissue to be dissected and/or tissue layers to be separated, creating a space for lead implantation. Again, a lumen may be provided within the tool 2100 for a guidewire, stylet, or lead.

The devices of FIGS. 20A-20B and 21A-21B may be used in a method such as detailed above in FIG. 2. For example, the tunneling tip 2002 or 2102 may be advanced through an incision to a desired location, with or without use of a guidewire or stylet. A preliminary tunnel is thus created to a desired location which may be subcutaneous, substernal, or another location to which lead placement is desired. Next, the spring coil 2004 or cutting wire 2104 is extended out of slots 2010/2110 to assume the dissection configuration shown in FIGS. 20B/21B. The tools 2000, 2100 are then moved by advancing or withdrawing them to dissect tissue or separate tissue layers. The proximal ends of each tool 2000, 2100 may include flattened or other portions for alignment to the desired tissue plane, as in earlier examples. The aim may be to separate tissue layers as opposed to actually cutting tissue itself. As before, if desired, a lead having an expandable electrode may be placed through a lumen (not shown) in tool 2000/2100 and during tool removal the lead may be kept in place and the electrode then expanded into the created space.

Non-Limiting Examples

In a first example an implantable defibrillator may comprise a canister housing a source of electrical energy, a capacitor, and operational circuitry that senses heart rhythms and an electrode and lead assembly. The electrode and lead assembly may comprise a lead, at least one sensing electrode, and at least one shocking electrode. The at least one shocking electrode may extend over a length in the range of 50 to 110 millimeters and a width in the range of 1 to 40 millimeters.

Alternatively or additionally to any of the examples above, in a second example, the at least one shocking electrode may comprise a coil electrode having a generally flattened oval shape.

Alternatively or additionally to any of the examples above, in a third example, the coil electrode may have a closed pitch.

Alternatively or additionally to any of the examples above, in a fourth example, the at least one shocking electrode may comprise a plurality of coil electrodes.

Alternatively or additionally to any of the examples above, in a fifth example, the plurality of coil electrodes may be configured to be actuated between a delivery configuration and an implanted configuration.

Alternatively or additionally to any of the examples above, in a sixth example, the implanted configuration may have a larger width than the delivery configuration.

Alternatively or additionally to any of the examples above, in a seventh example, the implantable defibrillator may further comprise a push-pull mechanism configured to move the plurality of electrodes between the delivery configuration and the implanted configuration.

Alternatively or additionally to any of the examples above, in an eighth example, the shocking electrode may comprise a first coil electrode having one or more oscillations about a longitudinal axis of the lead, each oscillation having at least one peak and valley.

Alternatively or additionally to any of the examples above, in a ninth example, the shocking electrode may comprise a first coil electrode wound into a helical configuration.

Alternatively or additionally to any of the examples above, in a tenth example, the implantable defibrillator may further comprise a second coil electrode having one or more oscillations, each oscillation having at least one peak and valley, wherein the first and second coil electrodes are coiled in directions such that a valley of the first coil electrode may be positioned adjacent to a peak of the second coil electrode.

Alternatively or additionally to any of the examples above, in an eleventh example, the implantable defibrillator may further comprise a second coil wound into a helical configuration, wherein the first and second coil electrodes are wound in opposite directions.

Alternatively or additionally to any of the examples above, in a twelfth example, the shocking electrode may comprise a woven electrically conductive mesh at least partially embedded in a silicone carrier.

Alternatively or additionally to any of the examples above, in a thirteenth example, the shocking electrode may comprise a printed circuit disposed on a liquid crystal polymer.

Alternatively or additionally to any of the examples above, in a fourteenth example, one of the at least one sensing electrode and the at least one shocking electrode may further comprise a high capacitive coating.

Alternatively or additionally to any of the examples above, in a fifteenth example, the implantable defibrillator may further comprise a membrane disposed over at least a portion of the lead and electrode assembly.

Alternatively or additionally to any of the examples above, in a sixteenth example, the at least one shocking electrode may extend over a length in the range of 60 to 100 millimeters.

Alternatively or additionally to any of the examples above, in a seventeenth example, the at least one shocking electrode may extend over a length in the range of 70 to 90 millimeters.

Alternatively or additionally to any of the examples above, in a eighteenth example, the at least one shocking electrode may have a width in the range of 10 to 30 millimeters.

Alternatively or additionally to any of the examples above, in a nineteenth example, the at least one shocking electrode may have a width in the range of 15 to 25 millimeters.

Alternatively or additionally to any of the examples above, in a twentieth example, the lead may be configured for subcutaneous implantation and the canister houses operational circuitry configured for use as a subcutaneous-only defibrillator.

In a twenty first example, a method of implanting a defibrillator as in any of examples one through twenty may comprise implanting the canister in the left axillary region of a patient, implanting the lead subcutaneously over the ribcage of the patient and beneath the skin, and coupling the lead to the canister.

Alternatively or additionally to any of the examples above, in a twenty second example, the lead may be configured for implantation beneath the sternum of a patient and the canister houses operational circuitry configured for use as a substernal defibrillator.

In a twenty third example, a method for implanting a defibrillator as in any of example one through nineteen or twenty two may comprise implanting the canister in the left axillary region of a patient, implanting the lead substernally behind the sternum of the patient and outside of the heart and pericardium, and coupling the lead to the canister.

In a twenty fourth example, an implantable defibrillator may comprise a canister housing a source of electrical energy, a capacitor, and operational circuitry that senses heart rhythms and an electrode and lead assembly. The electrode and lead assembly may comprise a lead, at least one sensing electrode, and a coil electrode comprising a helically wound element and having a generally oval cross-sectional shape. The coil electrode may extend over a length in the range of 50 to 110 millimeters and a width in the range of 1 to 40 millimeters.

Alternatively or additionally to any of the examples above, in a twenty fifth example, the coil electrode may have a closed pitch.

Alternatively or additionally to any of the examples above, in a twenty sixth example, the coil electrode may have an open pitch.

Alternatively or additionally to any of the examples above, in a twenty seventh example, the coil electrode may be disposed over a portion of the lead.

Alternatively or additionally to any of the examples above, in a twenty eighth example, the at least one sensing electrode may comprise a proximal sensing electrode positioned proximal to the coil electrode and a distal sensing electrode positioned distal to the coil electrode.

Alternatively or additionally to any of the examples above, in a twenty ninth example, one of the at least one sensing electrode and the coil electrode may further comprise a high capacitive coating.

Alternatively or additionally to any of the examples above, in a thirtieth example, the implantable defibrillator may further comprise a membrane disposed over at least a portion of the lead and electrode assembly.

Alternatively or additionally to any of the examples above, in a thirty first example, the coil electrode may extend over a length in the range of 60 to 100 millimeters.

Alternatively or additionally to any of the examples above, in a thirty second example, the coil electrode may extend over a length in the range of 70 to 90 millimeters.

Alternatively or additionally to any of the examples above, in a thirty third example, the coil electrode may have a width in the range of 10 to 30 millimeters.

Alternatively or additionally to any of the examples above, in a thirty fourth example, the coil electrode may have a width in the range of 15 to 25 millimeters.

In a thirty fifth example, an implantable defibrillator may comprise a canister housing a source of electrical energy, a capacitor, and operational circuitry that senses heart rhythms and an electrode and lead assembly. The electrode and lead assembly may comprise a lead, at least one sensing electrode, and a shocking electrode. The shocking electrode may comprise a first electrode and a second electrode each having a proximal end and a distal end, wherein the first electrode and the second electrode are each coupled to the lead at their proximal and distal ends.

Alternatively or additionally to any of the examples above, in a thirty sixth example, the implantable defibrillator may further comprise an actuation mechanism.

Alternatively or additionally to any of the examples above, in a thirty seventh example, the actuation mechanism may be a push-pull member.

Alternatively or additionally to any of the examples above, in a thirty eighth example, the shocking electrode may be configured to be actuated between a delivery configuration and an implanted configuration.

Alternatively or additionally to any of the examples above, in a thirty ninth example, the implanted configuration may have a larger width than a width of the delivery configuration.

Alternatively or additionally to any of the examples above, in a fortieth example, at least one of the first and second electrodes may comprise an electrically conductive strut.

Alternatively or additionally to any of the examples above, in a forty first example, at least one of the first and second electrodes may comprise a helically wound coil electrode.

Alternatively or additionally to any of the examples above, in a forty second example, the first and second electrodes may be axially spaced from a longitudinal axis of the lead.

Alternatively or additionally to any of the examples above, in a forty third example, the at least one sensing electrode may comprise a proximal sensing electrode positioned proximal to the shocking electrode and a distal sensing electrode positioned distal to the shocking electrode.

Alternatively or additionally to any of the examples above, in a forty fourth example, one of the at least one sensing electrode and the shocking electrode may further comprise a high capacitive coating.

Alternatively or additionally to any of the examples above, in a forty fifth example, the implantable defibrillator may further comprise a membrane disposed over at least a portion of the lead and electrode assembly.

Alternatively or additionally to any of the examples above, in a forty sixth example, when in the implanted configuration, the shocking electrode may extend over a length in the range of 50 to 110 millimeters.

Alternatively or additionally to any of the examples above, in a forty seventh example, when in the implanted configuration, the shocking electrode may extend over a length in the range of 60 to 100 millimeters.

Alternatively or additionally to any of the examples above, in a forty eighth example, when in the implanted configuration, the shocking electrode may extend over a length in the range of 70 to 90 millimeters.

Alternatively or additionally to any of the examples above, in a forty ninth example, when in the implanted configuration, the shocking electrode may have a width in the range of 1 to 40 millimeters.

Alternatively or additionally to any of the examples above, in a fiftieth example, when in the implanted configuration, the shocking electrode may have a width in the range of 10 to 30 millimeters.

Alternatively or additionally to any of the examples above, in a fifty first example, when in the implanted configuration, the shocking electrode may have a width in the range of 15 to 25 millimeters.

In a fifty second example, an implantable defibrillator may comprise a canister housing a source of electrical energy, a capacitor, and operational circuitry that senses heart rhythms and an electrode and lead assembly. The electrode and lead assembly may comprise a lead having a longitudinal axis, at least one sensing electrode, and a shocking electrode. The shocking electrode may comprise a first coil electrode having a curved configuration including a first curved region that may extend axially away from the longitudinal axis of the lead in a first direction and a second curved region that may extend axially away from the longitudinal axis of the lead in a second direction opposite from the first. The shocking electrode may extend over a length in the range of 50 to 110 millimeters and a width in the range of 1 to 40 millimeters.

Alternatively or additionally to any of the examples above, in a fifty third example, the first curved region and the second curved region of the first coil electrode form at least a partial oscillation about the longitudinal axis of the lead.

Alternatively or additionally to any of the examples above, in a fifty fourth example, the first coil electrode may further comprise additional curved regions to form one or more oscillations about the longitudinal axis of the lead.

Alternatively or additionally to any of the examples above, in a fifty fifth example, the shocking electrode may further comprise a second coil electrode, the second coil electrode having a having a curved configuration including a first curved region that may extend axially away from the longitudinal axis of the lead in the second direction and a second curved region that may extend axially away from the longitudinal axis of the lead in the first direction opposite.

Alternatively or additionally to any of the examples above, in a fifty sixth example, the first coil electrode and the second coil electrode may cross at one or more cross points.

Alternatively or additionally to any of the examples above, in a fifty seventh example, the first coil electrode may be configured to be straightened into a straightened configuration for delivery.

Alternatively or additionally to any of the examples above, in a fifty eighth example, the second coil electrode may be configured to be straightened into a straightened configuration for delivery.

Alternatively or additionally to any of the examples above, in a fifty ninth example, when in the straightened configuration, the first coil electrode may have a reduced profile relative to the curved configuration.

Alternatively or additionally to any of the examples above, in a sixtieth example, when in the straightened configuration, the second coil electrode may have a reduced profile relative to the curved configuration.

Alternatively or additionally to any of the examples above, in a sixty first example, the at least one sensing electrode may comprise a proximal sensing electrode positioned proximal to the shocking electrode and a distal sensing electrode positioned distal to the shocking electrode.

Alternatively or additionally to any of the examples above, in a sixty second example, at least a portion of the lead and electrode assembly may further comprise a high capacitive coating.

Alternatively or additionally to any of the examples above, in a sixty third example, the implantable defibrillator may further comprise a membrane disposed over at least a portion of the lead and electrode assembly.

Alternatively or additionally to any of the examples above, in a sixty fourth example, the shocking electrode may extend over a length in the range of 60 to 100 millimeters.

Alternatively or additionally to any of the examples above, in a sixty fifth example, the shocking electrode may extend over a length in the range of 70 to 90 millimeters.

Alternatively or additionally to any of the examples above, in a sixty sixth example, the shocking electrode may have a width in the range of 10 to 30 millimeters.

Alternatively or additionally to any of the examples above, in a sixty seventh example, the shocking electrode may have a width in the range of 15 to 25 millimeters.

In a sixty eighth example an implantable defibrillator may comprise a canister housing a source of electrical energy, a capacitor, and operational circuitry that senses heart rhythms and an electrode and lead assembly. The electrode and lead assembly may comprise a lead having a longitudinal axis, at least one sensing electrode, and a shocking electrode. The shocking electrode may comprise a first coil electrode may comprise a helically wound element, the first coil electrode wound into a first helical configuration about the longitudinal axis of the lead. The shocking electrode may extend over a length in the range of 50 to 110 millimeters and a width in the range of 1 to 40 millimeters.

Alternatively or additionally to any of the examples above, in a sixty ninth example, the shocking electrode may further comprise a second coil electrode may comprise a helically wound element, the second coil electrode wound into a second helical configuration about the longitudinal axis of the lead, the second helical configuration extending in a rotational direction opposite the first helical configuration.

Alternatively or additionally to any of the examples above, in a seventieth example, the first coil electrode and the second coil electrode may cross at one or more cross points.

Alternatively or additionally to any of the examples above, in a seventy first example, the first coil electrode may be configured to be straightened into a straightened configuration for delivery.

Alternatively or additionally to any of the examples above, in a seventy second example, the second coil electrode may be configured to be straightened into a straightened configuration for delivery.

Alternatively or additionally to any of the examples above, in a seventy third example, when in the straightened configuration, the first coil electrode may have a reduced profile relative to the curved configuration.

Alternatively or additionally to any of the examples above, in a seventy fourth example, when in the straightened configuration, the second coil electrode may have a reduced profile relative to the curved configuration.

Alternatively or additionally to any of the examples above, in a seventy fifth example, the at least one sensing electrode may comprise a proximal sensing electrode positioned proximal to the shocking electrode and a distal sensing electrode positioned distal to the shocking electrode.

Alternatively or additionally to any of the examples above, in a seventy sixth example, at least a portion of the lead and electrode assembly may further comprise a high capacitive coating.

Alternatively or additionally to any of the examples above, in a seventy seventh example, the implantable defibrillator may further comprise a membrane disposed over at least a portion of the lead and electrode assembly.

Alternatively or additionally to any of the examples above, in a seventy eighth example, the shocking electrode may extend over a length in the range of 60 to 100 millimeters.

Alternatively or additionally to any of the examples above, in a seventy ninth example, the shocking electrode may extend over a length in the range of 70 to 90 millimeters.

Alternatively or additionally to any of the examples above, in an eightieth example, the shocking electrode may have a width in the range of 10 to 30 millimeters.

Alternatively or additionally to any of the examples above, in an eighty first example, the shocking electrode may have a width in the range of 15 to 25 millimeters.

In an eighty second example, an implantable defibrillator may comprise a canister housing a source of electrical energy, a capacitor, and operational circuitry that senses heart rhythms and an electrode and lead assembly. The electrode and lead assembly may comprise a lead having a longitudinal axis, at least one sensing electrode, and a shocking electrode. The shocking electrode may comprise an electrically conductive material embedded in a silicone carrier. The shocking electrode may extend over a length in the range of 50 to 110 millimeters and a width in the range of 1 to 40 millimeters.

Alternatively or additionally to any of the examples above, in an eighty third example, the electrically conductive material may comprise one or more woven filaments.

Alternatively or additionally to any of the examples above, in an eighty forth example, the electrically conductive material may comprise one or more braided filaments.

Alternatively or additionally to any of the examples above, in an eighty fifth example, the electrically conductive material may comprise a laser cut pattern.

In an eighty sixth example, an implantable defibrillator may comprise a canister housing a source of electrical energy, a capacitor, and operational circuitry that senses heart rhythms and an electrode and lead assembly. The electrode and lead assembly may comprise a lead having a longitudinal axis, at least one sensing electrode, and a shocking electrode. The shocking electrode may comprise a printed circuit disposed on a liquid crystal polymer. The shocking electrode may extend over a length in the range of 50 to 110 millimeters and a width in the range of 1 to 40 millimeters.

Alternatively or additionally to any of the examples above, in an eighty seventh example, the printed circuit may comprise one or more traces.

Alternatively or additionally to any of the examples above, in an eighty eighth example, the one or more traces may be positioned in a winding configuration on the liquid crystal polymer.

Alternatively or additionally to any of the examples above, in an eighty ninth example, the one or more traces may fan out from a central region.

Alternatively or additionally to any of the examples above, in a ninetieth example, the printed circuit may comprise one or more electrode pads.

Alternatively or additionally to any of the examples above, in a ninety first example, the shocking electrode may have a generally oval shaped outer perimeter.

Alternatively or additionally to any of the examples above, in a ninety second example, the shocking electrode may have a generally rectangular shaped outer perimeter.

Alternatively or additionally to any of the examples above, in a ninety third example, the shocking electrode may be configured to be rolled for delivery.

Alternatively or additionally to any of the examples above, in a ninety fourth example, the at least one sensing electrode may comprise a proximal sensing electrode positioned proximal to the shocking electrode and a distal sensing electrode positioned distal to the shocking electrode.

Alternatively or additionally to any of the examples above, in a ninety fifth example, at least a portion of the lead and electrode assembly may further comprise a high capacitive coating.

Alternatively or additionally to any of the examples above, in a ninety sixth example, the implantable defibrillator may further comprise a membrane disposed over at least a portion of the lead and electrode assembly.

Alternatively or additionally to any of the examples above, in a ninety seventh example, the shocking electrode may extend over a length in the range of 60 to 100 millimeters.

Alternatively or additionally to any of the examples above, in a ninety eighth example, the shocking electrode may extend over a length in the range of 70 to 90 millimeters.

Alternatively or additionally to any of the examples above, in a ninety ninth example, the shocking electrode may have a width in the range of 10 to 30 millimeters.

Alternatively or additionally to any of the examples above, in a one hundredth example, the shocking electrode may have a width in the range of 15 to 25 millimeters.

Alternatively or additionally to any of the examples above, in a one hundred and first example, the lead may be configured for subcutaneous implantation and the canister houses operational circuitry configured for use as a subcutaneous-only defibrillator.

In a one hundred and second example, a method for implanting a defibrillator as in any of examples twenty four through one hundred and one may comprise implanting the canister in the left axillary region of a patient, implanting the lead subcutaneously over the ribcage of the patient and beneath the skin, and coupling the lead to the canister.

Alternatively or additionally to any of the examples above, in a one hundred and third example, the lead may be configured for implantation beneath the sternum of a patient and the canister houses operational circuitry configured for use as a substernal defibrillator.

In a one hundred and fourth example, a method for implanting a defibrillator as in any of examples twenty four through one hundred and one or one hundred and three may comprise implanting the canister in the left axillary region of a patient, implanting the lead substernally behind the sternum of the patient and outside of the heart and pericardium, and coupling the lead to the canister.

Each of these non-limiting examples can stand on its own, or can be combined in various permutations or combinations with one or more of the other examples.

The materials that can be used for the various components of the lead and electrode assembly, delivery tools, and/or other devices disclosed herein may include those commonly associated with medical devices. For simplicity purposes, the following discussion makes reference to accessory devices and their related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the accessory devices and their related components may be doped with, made of, or include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable defibrillator comprising:
    a canister housing a source of electrical energy, a capacitor, and operational circuitry that senses heart rhythms; and
    an electrode and lead assembly, the electrode and lead assembly comprising:
        a lead body having a longitudinal axis, including a proximal end, an intermediate region, and a distal end;
        at least one sensing electrode, wherein the at least one sensing electrode is positioned at the distal end of the lead body;
        a shocking electrode, the shocking electrode comprising at least two coil electrodes, wherein a first coil electrode of the at least two coil electrodes and a second coil electrode of the at least two coil electrodes each have a proximal end and a distal end, wherein the first coil electrode and the second coil electrode are each coupled to the lead at their proximal and distal ends such that the proximal ends of the first and second coil electrodes are at the same location on the lead, and the distal ends of the first and second coil electrodes are at the same location on the lead;
        a push-pull member configured to actuate the shocking electrode between a delivery configuration and an implanted configuration, wherein the actuation of the shocking electrode moves the first and second coil electrodes in an outward direction away from the longitudinal axis of the lead body to expand the shocking electrode profile, such that the implanted configuration has a larger width than a width of the delivery configuration.

2. The implantable defibrillator of claim 1, wherein the shocking electrode is biased to an expanded configuration in which the first and second electrodes are spaced from one another in at least a portion thereof to define a first width, and the shocking electrode is collapsible into a delivery configuration by constraint within a sheath to a second width less than the first width.

3. The implantable defibrillator of claim 1, wherein at least one of the first and second coil electrodes comprises a helically wound coil electrode.

4. The implantable defibrillator of claim 1, wherein the first and second coil electrodes are axially spaced from a longitudinal axis of the lead body.

5. The implantable defibrillator of claim 1, wherein the at least one sensing electrode comprises a proximal sensing electrode positioned proximal to the shocking electrode and a distal sensing electrode positioned distal to the shocking electrode.

6. The implantable defibrillator of claim 1, further comprising a membrane disposed over at least a portion of the electrode and lead assembly.

7. The implantable defibrillator of claim 1 wherein the shocking electrode extends over a length in the range of 50 to 110 millimeters.

8. The implantable defibrillator of claim 1 wherein the shocking electrode extends over a length in the range of 70 to 90 millimeters.

9. The implantable defibrillator of claim 1 wherein the shocking electrode has a width in the range of 10 to 30 millimeters.

10. The implantable defibrillator of claim 1 wherein the shocking electrode has a width in the range of 15 to 25 millimeters.

11. The implantable defibrillator of claim 1, wherein the shocking electrode includes a first length while in the delivery configuration and a second length that is less than the first length while in the implanted configuration, such that when the push-pull member actuates the shocking electrode from the delivery configuration to the implanted configuration, the shocking electrode shortens in length relative to the lead body.

12. An implantable defibrillator comprising:
a canister housing a source of electrical energy, a capacitor, and operational circuitry that senses heart rhythms; and
an electrode and lead assembly, the electrode and lead assembly comprising:
a lead body having a longitudinal axis, including a proximal end, an intermediate region, and a distal end;
at least one sensing electrode, wherein the at least one sensing electrode is positioned at the distal end of the lead body; and
a shocking electrode comprising a first coil electrode comprising a helically wound element, the first coil electrode in a relaxed state being wound into a first helical configuration about the longitudinal axis of the lead body;
wherein the first coil electrode is configured to be straightened into a straightened configuration for delivery such that when the first coil electrode is in the straightened configuration, the first coil electrode has a greater length relative to the lead body;
wherein the shocking electrode extends over a length in the range of 50 to 110 millimeters and a width in the range of 1 to 40 millimeters.

13. The implantable defibrillator of claim 12, wherein the shocking electrode further comprises a second coil electrode comprising a helically wound element, the second coil electrode in a relaxed state being wound into a second helical configuration about the longitudinal axis of the lead body, the second helical configuration extending in a rotational direction opposite the first helical configuration.

14. The implantable defibrillator of claim 12, wherein when in the straightened configuration, the first coil electrode has a reduced profile relative to the first helical configuration.

15. The implantable defibrillator of claim 12, wherein the at least one sensing electrode comprises a proximal sensing electrode positioned proximal to the shocking electrode and a distal sensing electrode positioned distal to the shocking electrode.

16. The implantable defibrillator of claim 12, further comprising a membrane disposed over at least a portion of the electrode and lead assembly.

17. The implantable defibrillator of claim 12, wherein the shocking electrode extends over a length in the range of 60 to 100 millimeters.

18. The implantable defibrillator of claim 12, wherein the shocking electrode has a width in the range of 10 to 30 millimeters.

* * * * *